United States Patent [19]

Kaneko et al.

[11] Patent Number: 4,634,706

[45] Date of Patent: Jan. 6, 1987

[54] GRISEOLIC ACID DERIVATIVES, AND THEIR USE AS ENZYME INHIBITORS

[75] Inventors: Masakatsu Kaneko; Misako Kimura; Yoshinobu Murofushi; Mitsuo Yamazaki; Nobuyoshi Iwata; Fumio Nakagawa, all of Tokyo, Japan

[73] Assignee: Sankyo Company Limited, Tokyo, Japan

[21] Appl. No.: 664,866

[22] Filed: Oct. 25, 1984

[30] Foreign Application Priority Data

Oct. 28, 1983 [JP] Japan .................. 58-202362

[51] Int. Cl.$^4$ .................. A61K 31/52; C07D 473/00; C07D 473/30; C07D 473/34; C07D 473/38; C07D 473/40
[52] U.S. Cl. .................. 514/262; 514/266; 544/264; 544/265; 544/276; 544/277
[58] Field of Search .............. 544/265, 277, 264, 276; 514/266, 262

[56] References Cited

U.S. PATENT DOCUMENTS

| | | | |
|---|---|---|---|
| 3,862,189 | 1/1975 | Schwender | 544/265 |
| 4,138,562 | 2/1979 | Vince | 544/277 |
| 4,360,522 | 11/1982 | Schaeffer | 544/265 |
| 4,460,765 | 7/1984 | Naito et al. | 544/277 |
| 4,479,951 | 10/1984 | Klessing et al. | 544/277 |

FOREIGN PATENT DOCUMENTS 0029329  5/1981  European Pat. Off. ............ 544/277

*Primary Examiner*—Donald G. Daus
*Assistant Examiner*—Stephen M. Kapner
*Attorney, Agent, or Firm*—Frishauf, Holtz, Goodman & Woodward

[57] ABSTRACT

Griseolic acid derivatives of formula (I):

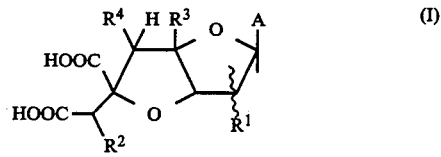

wherein A represents:

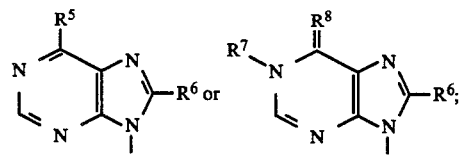

have enzyme-inhibitory activity, especially against cAMP PDE and cGMP PDE. When formulated as compositions with appropriate carriers or diluents, they may be used for the treatment of a variety of organic disorders and show toxicities less than griseolic acid itself.

38 Claims, No Drawings

GRISEOLIC ACID DERIVATIVES, AND THEIR USE AS ENZYME INHIBITORS

BACKGROUND TO THE INVENTION

The present invention relates to a series of novel griseolic derivatives and provides methods of using them and compositions containing them.

Griseolic acid is a nucleoside-type compound having an adenine base and two carboxylic acid groups. It was first disclosed in, inter alia, European patent specification No. 29,329A, but its structure was not, at that stage, known. Its structure was first disclosed in U.S. Pat. No. 4,460,765 (assigned to the present assignees) and published after the priority hereof.

The structure of griseolic acid may be represented by the formula:

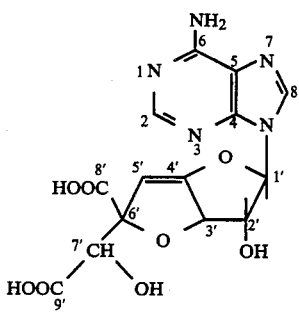

It should be noted that natural griseolic acid, being a product of natural biosynthesis, is synthesized stereospecifically. In fact, at both the 2' and the 7' positions, it is in the R-configuration.

In accordance with the recommendations of the International Union of Pure and Applied Chemistry (I.U.P.A.C.), the compounds of the present invention are named as derivatives of griseolic acid, taking griseolic acid as the parent structure. The numbering system employed herein is that shown on the above formula of griseolic acid.

In naming specific compounds of the present invention in accordance with this convention, substituents at the 2' and 7' positions are assumed to be in the R-configuration (like natural griseolic acid) unless the contrary is stated.

Griseolic acid, as well as the derivatives of the present invention, has the ability to inhibit the activity of cyclic adenosine monophosphate (cAMP) phosphodiesterase (PDE) and can thus increase the level of cAMP in the cells of a patient treated with it.

It is well-known that cAMP, which is very widely distributed in animal tissues, functions as a second messenger for and mediates the effect of a large number of hormones; as a result, cAMP has a variety of very important physiological and biochemical roles. Additionally, it is known to have an effect on or participate in: division, growth and differentiation of cells; systole; haemapoiesis; various activities of the central nervous system; immune reactions; and liberation of insulin and histamine. Its concentration in tissues, and hence its effect on these various functions, depends upon the balance between the enzyme which synthesizes cAMP (adenylate cyclase) and the enzyme which decomposes cAMP PDE. An inhibitor against cAMP PDE would increase the level of cAMP in the cells and would thus be a value as an angiocardiokinetic agent, an antiasthmatic agent, a smooth muscle relaxant, a psychotropic or neurotropic agent, an anti-inflammatory agent, an anti-cancer agent and a treatment for diabetes.

Griseolic acid has been demonstrated to have the range of biochemical activities described in the preceding paragraph and we have now discovered a series of novel derivatives of griseolic acid which likewise have these activities but which have a surprisingly low toxicity. In particular, the compounds of the invention have been found to improve brain metabolism substantially, to potentiate the effect of known anti-cancer agents and to potentiate the effect of insulin. Moreover, the compounds of the invention have been found to improve blood viscosity.

BRIEF SUMMARY OF INVENTION

It is, therefore, an object of the invention to provide, as a new composition of matter, a series of compounds having an inhibitory effect against cAMP PDE and a low toxicity.

It is a further object of the invention to provide a pharmaceutical composition for the amelioration of organic disorders arising from an inadequate level of cAMP in the tissues.

The new compounds of the invention can be characterized by the chemical structure (I):

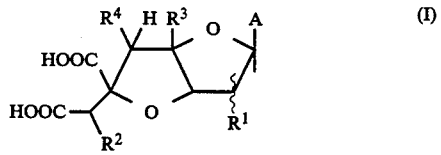

wherein:

A represents a group of formula:

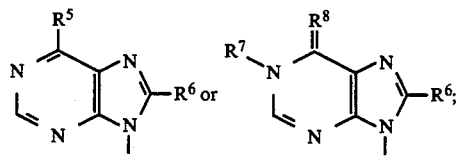

$R^1$, $R^2$, $R^5$ and $R^6$ are the same or different and each represents a hydrogen or halogen atom, the azido group, or a group of formula $-OR^9$, $-NR^{10}R^{11}$ or $-SR^9$;

$R^3$ represents a hydrogen or halogen atom or an acyloxy or $C_1-C_6$ alkoxy group;

$R^4$ represents a hydrogen or halogen atom; or $R^3$ and $R^4$ together represent an extra carbon-carbon bond between the carbon atoms to which they are attached; or $R^3$ and $R^2$ together represent an oxygen atom bridging the carbon atoms to which they are attached;

$R^7$ represents an optionally substituted $C_1-C_6$ alkyl, $C_1-C_6$ alkenyl or aralkyl group (wherein the alkyl moiety has from 1 to 6 carbon atoms), the substituents being selected from halogen atoms, $C_1-C_4$ alkoxy groups, ($C_1-C_4$ alkoxy)carbonyl groups and (where $R^7$ is substituted aralkyl) $C_1-C_4$ alkyl groups;

$R^8$ represents an oxygen or sulfur atom or the imino group;

$R^9$ represents hydrogen, a $C_1-C_6$ alkyl group, a heterocyclic group (having 5 or 6 ring atoms, of which from 1 to 3 are oxygen, nitrogen or sulfur, and being unsubstituted or having from 1 to 3 $C_1-C_4$ alkyl or alkoxy substituents), a tri($C_1-C_4$ alkyl)silyl group, an alkylsulfonyl group, a haloalkylsulfonyl group, an arylsulfonyl group, a $C_1-C_{20}$ aliphatic acyl group or an aromatic acyl group;

$R^{10}$ and $R^{11}$ are the same or different and each represents hydrogen, hydroxy, a $C_1-C_6$ alkyl group, a $C_1-C_6$ hydroxyalkyl group, a $C_1-C_6$ aminoalkyl group, an aralkyl group, an aryl group, a $C_1-C_6$ alkoxy group, the amino group, a $C_1-C_{20}$ aliphatic acyl group or an aromatic acyl group; or $R^{10}$ and $R^{11}$, together with the nitrogen atom to which they are attached, represent a 5- or 6-membered heterocyclic group optionally having at least one other hetero-atom selected from oxygen, nitrogen and sulfur atoms and optionally having from 1 to 3 $C_1-C_4$ alkyl or alkoxy substituents;

and pharmaceutically acceptable salts and esters thereof; but excluding 7'(R)-griseolic acid itself and salts thereof.

The invention also provides a pharmaceutical composition comprising at least one of the compounds of the invention in admixture with a pharmaceutically acceptable carrier or diluent.

DETAILED DESCRIPTION OF INVENTION

In the compounds of the invention, where $R^3$ and $R^4$ together represent an extra bond, this forms a carbon-carbon double bond between the carbon atoms at the 4' and 5' positions (as in griseolic acid itself) and the resulting compounds may be represented by the formula (Ia):

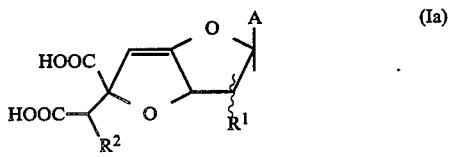

(in which $R^1$, $R^2$, A, and $R^5-R^8$ are as defined above).

Where $R^2$ and $R^3$ together represent a bridging (ether-type) oxygen atom, the compounds may be represented by the formula (Ib):

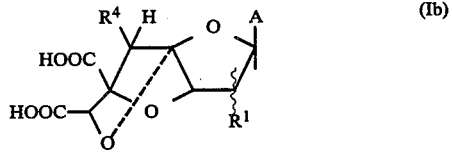

(in which $R^1$, $R^4$, A, and $R^5-R^8$ are as defined above). Compounds of formula (Ib) are named by the substractive "anhydro" system of nomenclature prescribed by Rule C-44.1 of the I.U.P.A.C. Rules on Nomenclature of Organic Chemistry. They are thus regarded as compounds having a hydroxy group at the 4'α-position ($R^3$=hydroxy) and having one molecule of water removed between the 4'α and 7' positions. They are accordingly named as 4',7'-anhydro-4'α-hydroxygriseolic acid derivatives.

In the compounds of the invention, where $R^1$, $R^2$, $R^3$, $R^4$, $R^5$, $R^6$ or the substituent on a group represented by $R^7$ is a halogen atom, this is suitably a fluorine, chlorine, bromine or iodine atom.

Where $R^1$, $R^2$, $R^5$ or $R^6$ represents a group of formula $-OR^9$, it is a hydroxy, $C_1-C_6$ alkoxy, heterocyclic-oxy, trialkylsilyloxy, alkylsulfonyloxy, haloalkylsulfonyloxy, arylsulfonyloxy, $C_1-C_{20}$ aliphatic acyloxy or aromatic acyloxy group. The alkoxy group may be a straight or branched chain group and examples include the methoxy, ethoxy, propoxy, isopropoxy, butoxy, isobutoxy, sec-butoxy, t-butoxy, pentyloxy and hexyloxy groups. The heterocyclic-oxy group is preferably such a group in which an oxygen atom is the only hetero-atom and is more preferably a pyranyl or di- or tetra-hydropyranyl group; examples of such groups represented by $-OR^9$ are the tetrahydropyran-2-yloxy and 4-methoxytetrahydropyran-4-yloxy groups. In the trialkylsilyloxy groups, the three alkyl groups may be the same or different and may be straight or branched chain groups; preferred such trialkylsilyloxy groups are the dimethylisopropylsilyloxy and t-butyldimethylsilyloxy groups. Preferred alkylsulfonyloxy groups are the methanesulfonyloxy, ethanesulfonyloxy and 1-propanesulfonyloxy groups. In the haloalkylsulfonyloxy groups, the halogen atom is preferably at least one fluorine atom, the perfluoroalkylsulfonyloxy groups being more preferred; preferred such groups are the trifluoromethanesulfonyloxy and pentafluoroethanesulfonyloxy groups. Preferred arylsulfonyloxy groups include the benzenesulfonyloxy and p-toluenesulfonyloxy groups. The aliphatic acyloxy groups which may be represented by $-OR^9$ may be straight or branched chain groups, which may be saturated or unsaturated and which may be short or long chain groups; examples of such acyloxy groups include the acetoxy, propionyloxy, butyryloxy, isobutyryloxy, valeryloxy, isovaleryloxy, octanoyloxy, lauroyloxy, palmitoyloxy and stearoyloxy groups. Examples of aromatic acyloxy groups include the benzoyloxy, p-toluoyloxy, p-anisoyloxy, p-chlorobenzoyloxy and p-nitrobenzoyloxy groups.

The optionally substituted mercapto groups of formula $-SR^9$, which may be represented by $R^1$, $R^2$, $R^5$ or $R^6$, may be the thio-analogs of the substituted hydroxy groups of formula $-OR^9$ mentioned above. However preferred such groups include: the mercapto group; $C_1-C_6$ alkylthio groups, particularly the methylthio, ethylthio, propylthio, isopropylthio, butylthio, isobutylthio, sec-butylthio, t-butylthio, pentylthio and hexylthio groups; aliphatic acylthio groups, such as the acetylthio, propionylthio, butyrylthio and isobutyrylthio groups; and aromatic acylthio groups, such as the benzoylthio, p-toluoylthio, p-anisoylthio and p-chlorobenzoylthio groups.

Where $R^1$, $R^2$, $R^5$ or $R^6$ represents an amino or substituted amino group of formula $-NR^{10}R^{11}$, $R^{10}$ and $R^{11}$ may be the same or different and each represents a hydrogen atom, a hydroxy group, a $C_1-C_6$ *alkyl group*, a $C_1-C_6$ hydroxyalkyl group, a $C_1-C_6$ aminoalkyl group, an aralkyl group, an aryl group, a $C_1-C_6$ alkoxy group, an amino group, a $C_1-C_{20}$ aliphatic acyl group or an aromatic acyl group; or $R^{10}$ and $R^{11}$ together may form a cyclic amino group. Except where hereafter otherwise specified, it is preferred that $R^{11}$ represents hydrogen and $R^{10}$ represents hydrogen or one of the above identified groups.

Where $R^{10}$ and/or $R^{11}$ represents an alkyl group, the group represented by $-NR^{10}R^{11}$ may be a mono- or di-alkylamino group, particularly the methylamino, dimethylamino, ethylamino, diethylamino, propylamino, dipropylamino, butylamino, isobutylamino, sec-butylamino, t-butylamino, pentylamino and hexylamino groups. Where $R^{10}$ represents a hydroxyalkyl group, preferred examples of groups represented by —$NR^{10}R^{11}$ are the 2-hydroxyethylamino and 3-hydroxypropylamino groups. Where $R^{10}$ represents an aminoalkyl group, preferred examples of the groups represented by —$NR^{10}R^{11}$ are the 2-aminoethylamino and 3-aminopropylamino groups. Where $R^{10}$ represents an aralkyl group, preferred examples of groups represented by —$NR^{10}R^{11}$ are the benzylamino, p-methylbenzylamino, p-methoxybenzylamino, p-chlorobenzylamino, phenethylamino, α-naphthylmethylamino and β-naphthylmethylamino groups. Where $R^{10}$ represents an aryl group, preferred examples of groups represented by —$NR^{10}R^{11}$ are the anilino, p-toluidino, p-anisidino, p-chloroanilino, α-naphthylamino and β-naphthylamino groups. Where $R^{10}$ represents a hydroxy group, the group —$NR^{10}R^{11}$ is preferably the hydroxyamino group. Where $R^{10}$ represents an alkoxy group, preferred examples of groups represented by —$NR^{10}R^{11}$ are the methoxyamino, ethoxyamino and propoxyamino groups. Where $R^{10}$ represents an amino group, the group represented by —$NR^{10}R^{11}$ is preferably the hydrazino group. Where $R^{10}$ and/or $R^{11}$ represents an aliphatic acyl group, preferred examples of groups represented by —$NR^{10}R^{11}$ are the acetamido, propionylamido, dipropionylamido, butyrylamido, dibutyrylamido, isobutyrylamido, valerylamido, isovalerylamido, octanoylamido, lauroylamido, palmitoylamido and stearoylamido groups. Where $R^{10}$ and/or $R^{11}$ represents an aromatic acyl group, preferred examples of groups represented by —$NR^{10}R^{11}$ are the benzamido, dibenzamido, p-toluoylamido, di-p-toluoylamido, p-anisoylamido, di-p-anisoylamido, p-chlorobenzamido, di-p-chlorobenzamido and p-nitrobenzamido groups. Where $R^{10}$ and $R^{11}$, together with the nitrogen atom to which they are attached, represent a cyclic amino group, this may optionally contain at least one other hetero-atom selected from oxygen, nitrogen and sulfur atoms and preferably contains either no other hetero-atom or one other hetero-atom selected from oxygen and nitrogen atoms. Preferred such cyclic amino groups which may be represented by —$NR^{10}R^{11}$ are the 1-pyrrolidinyl, 1-piperazinyl, morpholino and 4-methyl-1-piperazinyl groups.

Where $R^3$ represents an acyloxy group or a $C_1$–$C_6$ alkoxy groups, examples of such groups are given in relation to the group —$OR^9$ represented by $R^1$, $R^2$, $R^5$ or $R^6$.

Where $R^7$ represents an optionally substituted alkyl group, this is preferably a methyl, ethyl, propyl, isopropyl, butyl, isobutyl, sec-butyl, t-butyl, methoxycarbonylmethyl, ethoxycarbonylmethyl, propoxycarbonylmethyl, 2-methoxycarbonylethyl or 2-ethoxycarbonylethyl group.

Where $R^7$ represents an optionally substituted alkenyl group, it is preferably unsubstituted and preferred groups include the allyl and 2-butenyl groups.

Where $R^7$ represents an optionally substituted aralkyl group, this is preferably a benzyl, p-methylbenzyl, p-methoxybenzyl, p-chlorobenzyl, p-nitrobenzyl, 2,4,6-trimethylbenzyl, phenethyl, p-methylphenethyl, p-methoxyphenethyl or p-chlorophenethyl group.

Preferred classes of compounds of the present invention may be defined as follows:

(A) Compounds of formula (I), their salts and esters in which:
$R^1$ represents a hydrogen or halogen atom, the azido group or said group of formula —$OR^9$;
$R^2$ represents hydrogen or said group of formula —$OR^9$;
$R^3$ and $R^4$ together represent said extra bond;
$R^5$ represents a hydroxy, amino, $C_1$–$C_6$ alkylamino, acylamino or mercapto group; and
$R^6$ represents the hydrogen atom.

(B) Compounds of formula (I), their salts and esters in which:
$R^1$ represents a hydrogen or halogen atom or said group of formula —$OR^9$;
$R^2$ represents the hydrogen atom or said group of formula —$OR^9$;
$R^3$ and $R^4$ together represent said extra bond;
$R^5$ represents the amino group; and
$R^6$ represents a halogen atom, a mercapto or $C_1$–$C_6$ alkoxy group or said group of formula —$NR^{10}R^{11}$.

(C) Compounds of formula (I), their salts and esters in which:
$R^1$ represents the hydroxy group;
$R^4$ represents a halogen atom;
$R^3$ and $R^2$ together represent said oxygen atom;
$R^5$ represents the amino group; and
$R^6$ represents the hydrogen atom.

(D) The esters defined in (C) above.

(E) Compounds as defined in (A)–(D) above in which:
$R^7$ represents said optionally substituted aralkyl group; and
$R^8$ represents the imino group.

The compounds of formula (I) contain two carboxy groups and can thus form mono- or di-salts and mono- or di-esters. In the case of the di-salts and di-esters, the cationic moieties of the salts or the alcoholic moieties of the esters can be the same or different. In practice, however, it is most easy to prepare di-salts or di-esters, particularly those in which the two cationic moieties or the two alcoholic moieties are the same.

There is no particular limitation upon the nature of the alcoholic moiety of the ester, provided that it does not, or does not to an unacceptable extent, reduce the activity of the compound or increase its toxicity and all esters conventionally formed for compounds of this type may be formed with the compounds of the invention. Examples of esters include: $C_1$–$C_6$ alkyl esters, particularly the methyl, ethyl, propyl and butyl esters; aralkyl esters, particularly the benzyl and benzhydryl esters; aliphatic acyloxyalkyl esters (particularly the acyloxymethyl and acyloxyethyl esters), such as the acetoxymethyl, propionyloxymethyl, butyryloxymethyl, pivaloyloxymethyl, 1-acetoxyethyl, 1-propionyloxyethyl, 1-butyryloxyethyl and 1-pivaloyloxyethyl esters; ($C_1$–$C_4$ alkyl)oxycarbonyloxyethyl esters, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl and 1-isobutoxycarbonyloxyethyl esters; heterocyclic esters, such as the phthalidyl esters; and heterocyclylmethyl esters (in which the heterocyclic group is preferably as defined for $R^9$) for example the 5-methyl-2-oxo-1,3-dioxolen-4-ylmethyl esters.

There is no particular limitation on the nature of the cations employed to form salts of the compounds of the invention, provided that they do not, or do not to an unacceptable extent, reduce the activity or increase the toxicity of the compounds. Preferred salts include salts with alkali metals (such as sodium or potassium) or with alkaline earth metals (such as calcium).

Where any one or more of $R^1$, $R^2$, $R^5$ and $R^6$ represents an amino group, the compounds of the invention will also form acid addition salts. The nature of the acid employed to form such salts is not critical, provided that it does not, or does not to an unacceptable extent, reduce the activity or increase the toxicity of the compounds. Examples of such acids include: inorganic acids, such as hydrochloric acid, sulfuric acid and phosphoric acid; organic carboxylic acids, such as acetic acid, oxalic acid, maleic acid, succinic acid, citric acid, tartaric acid, fumaric acid, lauric acid, stearic acid and palmitic acid; and such organic sulfonic acids as methanesulfonic acid, benzenesulfonic acid and p-toluenesulfonic acid.

The compounds of the present invention have a number of asymmetric carbon atoms in their molecules and can, therefore, exist in the form of various stereoisomers. The present invention includes both the individual, isolated isomers as well as mixtures of these isomers. Griseolic acid, being a natural product, is a single isomer, in which both the 2' and 7' carbon atoms are in the R configuration; compounds prepared from griseolic acid may retain the same configuration or may have the inverted configuration at one or more of the asymmetric carbon atoms. For example, when $R^1$ represents a group or atom other than hydrogen, the configuration of the compounds at 2'-position may be α or β. When $R^2$ represents a group or atom other than hydrogen, the configuration at 7'-position may be RS, R or S.

Examples of compounds of the present invention are given in the following list; the compounds are hereafter, where appropriate, identified by the numbers assigned to them in this list.

1. dibenzhydryl $N^6,N^6,O^{2'},O^{7'}$-tetrabenzoylgriseolate
2. dibenzhydryl $N^6,N^6,O^{2'},O^{7'}$-tetra-p-toluoylgriseolate
3. dibenzhydryl $N^6,N^6,O^{2'},O^{7'}$-tetra-p-chlorobenzoylgriseolate
4. dibenzhydryl $N^6,N^6,O^{2'},O^{7'}$-tetra-p-nitrobenzoylgriseolate
5. dibenzhydryl $N^6,N^6,O^{2'},O^{7'}$-tetra-p-anisoylgriseolate
6. dibenzhydryl $O^{2'}$-benzoyl-$N^6,N^6,O^{7'}$-tri-p-toluoylgriseolate
7. dibenzhydryl $N^6,N^6,O^{7'}$-tri-p-anisoyl-$O^{2'}$-benzoylgriseolate
8. dibenzhydryl $N^6,N^6,O^{2'},O^{7'}$-tetrapropionylgriseolate
9. dibenzhydryl $N^6,N^6,O^{2'},O^{7'}$-tetrabutyrylgriseolate
10. dibenzhydryl $N^6,O^{2'},O^{7'}$-tripropionylgriseolate
11. dibenzhydryl $N^6,O^{2'},O^{7'}$-tributyrylgriseolate
12. dibenzhydryl $N^6,O^{2'},O^{7'}$-tribenzoylgriseolate
13. dibenzhydryl $N^6,O^{2'},O^{7'}$-triacetylgriseolate
14. dibenzhydryl $N^6,O^{7'}$-diacetyl-$O^{2'}$-benzoylgriseolate
15. dibenzhydryl $O^{2'},O^{7'}$-dibenzoylgriseolate
16. dibenzhydryl $O^{2'},O^{7'}$-dipropionylgriseolate
17. dibenzhydryl $O^{2'},O^{7'}$-dibutyrylgriseolate
18. dibenzhydryl $O^{2'},O^{7'}$-diacetylgriseolate
19. dibenzhydryl $O^{2'}$-benzoylgriseolate
20. dibenzhydryl griseolate
21. dimethyl griseolate
22. dimethyl $O^{2'},O^{7'}$-diacetylgriseolate
23. dimethyl $N^6,O^{2'},O^{7'}$-tribenzoylgriseolate
24. dimethyl $N^6,O^{2'},O^{7'}$-tri-p-chlorobenzoylgriseolate
25. dimethyl 4',7'-anhydro-5'α-bromo-4'α-hydroxygriseolate
26. disodium $N^6,O^{2'},O^{7'}$-tribenzoylgriseolate
27. disodium $N^6,O^{2'},O^{7'}$-tri-p-toluoylgriseolate
28. disodium $N^6,O^{2'},O^{7'}$-tri-p-chlorobenzoylgriseolate
29. disodium $N^6,O^{2'},O^{7'}$-tri-p-nitrobenzoylgriseolate
30. disodium $N^6,O^{2'},O^{7'}$-tri-p-anisoylgriseolate
31. disodium $O^{2'}$-benzoyl-$N^6,O^{7'}$-di-p-toluoylgriseolate
32. disodium $N^6,O^{7'}$-di-p-anisoyl-$O^{2'}$-benzoylgriseolate
33. $N^6,O^{7'}$-diacetyl-$O^{2'}$-benzoylgriseolic acid
34. $N^6,O^{2'},O^{7'}$-tributyrylgriseolic acid
35. $N^6$-benzoylgriseolic acid
36. $O^{2'}$-benzoylgriseolic acid
37. $O^{7'}$-benzoylgriseolic acid
38. $N^6,O^{2'}$-dibenzoylgriseolic acid
39. $N^6,O^{7'}$-dibenzoylgriseolic acid
40. $O^{2'},O^{7'}$-dibenzoylgriseolic acid
41. $O^{2'},O^{7'}$-diacetylgriseolic acid
42. $N^1$-methylgriseolic acid
43. $O^{7'}$-acetyl-$N^1$-methylgriseolic acid
44. $N^1$-butylgriseolic acid
45. $N^1$-benzylgriseolic acid
46. $O^{7'}$-acetyl-$N^1$-benzylgriseolic acid
47. dibenzhydryl $N^1$-benzylgriseolate
48. $N^1$-allylgriseolic acid
49. $N^1$-methoxycarbonylmethylgriseolic acid
50. $N^1$-phenethylgriseolic acid
51. 6-desamino-6-hydroxygriseolic acid
52. 6-chloro-6-desaminogriseolic acid
53. 6-desamino-6-hydrogriseolic acid
54. 6-desamino-6-mercaptogriseolic acid
55. 6-desamino-6-methylmercaptogriseolic acid
56. 6-azido-6-desaminogriseolic acid
57. $N^6$-methoxygriseolic acid
58. $N^6$-methylgriseolic acid
59. $N^6$-dimethylgriseolic acid
60. 6-desamino-6-hydrazinogriseolic acid
61. $N^6$-(2-hydroxyethyl)griseolic acid
62. $N^6$-(2-aminoethyl)griseolic acid
63. $N^6$-benzylgriseolic acid
64. $N^6$-phenethylgriseolic acid
65. $N^6$-α-naphthylmethylgriseolic acid
66. 6-desamino-6-piperidinogriseolic acid
67. 6-desamino-6-morpholinogriseolic acid
68. dibenzhydryl 6-desamino-6-hydroxygriseolate
69. $O^{2'},O^{7'}$-diacetyl-6-desamino-6-hydroxygriseolic acid
70. $O^{2'},O^{7'}$-dibenzoyl-6-desamino-6-hydroxygriseolic acid
71. dibenzhydryl $O^{2'},O^{7'}$-diacetyl-6-desamino-6-hydroxygriseolate
72. $O^{2'},O^{7'}$-diacetyl-6-chloro-6-desaminogriseolic acid
73. dimethyl $O^{2'},O^{7'}$-diacetyl-6-chloro-6-desaminogriseolate
74. dibenzhydryl 6-chloro-6-desaminogriseolate
75. dibenzhydryl $O^{2'},O^{7'}$-diacetyl-6-chloro-6-desaminogriseolate
76. dimethyl $O^{2'}$-benzoylgriseolate
77. dibenzhydryl $O^{2'}$-benzoyl-$O^{7'}$-mesylgriseolate
78. dimethyl $O^{2'}$-benzoyl-$O^{7'}$-mesylgriseolate
79. dibenzhydryl $O^{2'}$-benzoyl-$O^{7'}$-trifluoromethanesulfonylgriseolate
80. dimethyl $O^{2'}$-benzoyl-$O^{7'}$-trifluoromethanesulfonylgriseolate 81. 7'-azido-7'-deoxygriseolic acid
82. 7'-amino-7'-deoxygriseolic acid
83. 7'-deoxy-7'-mercaptogriseolic acid
84. 7'-deoxy-7'-methylthiogriseolic acid
85. 7'-deoxy-7'-methylaminogriseolic acid
86. 7'-deoxy-7'-dimethylaminogriseolic acid
87. 7'-benzylamino-7'-deoxygriseolic acid
88. 7'-chloro-7'-deoxygriseolic acid
89. 7'-bromo-7'-deoxygriseolic acid
90. 7'-deoxy-7'-iodogriseolic acid
91. 7'-deoxy-7'-fluorogriseolic acid
92. 7'-deoxy-7'-methylaminogriseolic acid
93. 7'-acetamido-7'-deoxygriseolic acid
94. 7'-benzamido-7'-deoxygriseolic acid
95. $O^{7'}$-methylgriseolic acid
96. $O^{7'}$-ethylgriseolic acid
97. $O^{7'}$-propylgriseolic acid
98. $O^{7'}$-butylgriseolic acid
99. $O^{7'}$-benzylgriseolic acid
100. $O^{7'}$-(tetrahydropyran-2-yl)griseolic acid
101. dimethyl $O^{7'}$-(tetrahydropyran-2-yl)griseolate
102. dibenzhydryl $O^{7'}$-(tetrahydropyran-2-yl)griseolate
103. dimethyl $O^{2'}$-mesyl-$O^{7'}$-(tetrahydropyran-2-yl)griseolate
104. dibenzhydryl $O^{2'}$-mesyl-$O^{7'}$-(tetrahydropyran-2-yl)griseolate
105. dimethyl $O^{7'}$-(tetrahydropyran-2-yl)-$O^{2'}$-trifluoromethanesulfonylgriseolate
106. dibenzhydryl $O^{7'}$-(tetrahydropyran-2-yl)-$O^{2'}$-trifluoromethanesulfonylgriseolate
107. 2'-azido-2'-deoxygriseolic acid
108. 2'-amino-2'-deoxygriseolic acid
109. 2'-chloro-2'-deoxygriseolic acid
110. 2'-bromo-2'-deoxygriseolic acid
111. 2'-deoxy-2'-iodogriseolic acid
112. 2'-deoxy-2'-fluorogriseolic acid
113. 2'-deoxy-2'-methylaminogriseolic acid
114. 2'-deoxy-2'-dimethylaminogriseolic acid
115. 2'-benzylamino-2'-deoxygriseolic acid
116. 2'-acetamido-2'-deoxygriseolic acid
117. 2'-benzamido-2'-deoxygriseolic acid
118. $O^{2'}$-methylgriseolic acid
119. $O^{2'}$-ethylgriseolic acid
120. $O^{2'}$-propylgriseolic acid
121. $O^{2'}$-butylgriseolic acid
122. 2'-deoxy-2'(S)-mercaptogriseolic acid
123. 2'-deoxy-2'(S)-methylmercaptogriseolic acid
124. 6-desamino-6-methoxygriseolic acid
125. $N^{6}$-phenylgriseolic acid
126. $O^{2'}$-benzoyl-6-desamino-6-hydroxygriseolic acid
127. 6-desamino-6-hydroxy-$N^{1}$-(2,4,6-trimethylbenzyl)griseolic acid
128. dibenzhydryl $O^{2'},O^{7'}$-diacetyl-6-desamino-6-hydroxy-$N^{1}$-(2,4,6-trimethylbenzyl)griseolate
129. dimethyl $O^{2'},O^{7'}$-diacetyl-6-desamino-6-hydroxygriseolate
130. dibenzhydryl 7'-azido-$O^{2'}$-benzoyl-7'-deoxygriseolate
131. $N^{6},O^{2'},O^{7'}$-tribenzoylgriseolic acid
132. dibenzhydryl $O^{2'},O^{7'}$-dibenzoyl-6-desamino-6-hydroxygriseolate
133. 7'-deoxygriseolic acid
134. dibenzhydryl 7'(S)-amino-$O^{2'}$-benzoyl-7'-deoxygriseolate
135. 7'(S)-amino-7'-deoxygriseolic acid
136. dibenzhydryl $O^{2'}$-benzoyl-7'(S)-bromo-7'-deoxygriseolate
137. 7'(S)-bromo-7'-deoxygriseolic acid
138. 6-desamino-7'-deoxy-6-hydroxygriseolic acid
139. dibenzhydryl 7'(S)-acetoxy-$O^{2'}$-benzoyl-7'-deoxygriseolate
140. 7'-deoxy-7'(S)-hydroxygriseolic acid
141. 7'(S)-acetoxy-7'-deoxygriseolic acid
142. 2'(S)-chloro-2'-deoxygriseolic acid
143. 2'(S)-bromo-2'-deoxygriseolic acid
144. 2'-deoxygriseolic acid
145. bis(1-acetoxyethyl)griseolate
146. bis(1-propionyloxyethyl)griseolate
147. bis(1-butyryloxyethyl)griseolate
148. bis(1-pivaloyloxyethyl)griseolate
149. bis(1-methoxycarbonyloxyethyl)griseolate
150. bis(1-ethoxycarbonyloxyethyl)griseolate
151. bis(1-propoxycarbonyloxyethyl)griseolate
152. bis(1-isopropoxycarbonyloxyethyl)griseolate
153. bis(1-butoxycarbonyloxyethyl)griseolate
154. bis(1-isobutoxycarbonyloxyethyl)griseolate
155. diphthalidyl griseolate
156. bis(5-methyl-2-oxo-1,3-dioxolen-4-ylmethyl)griseolate
157. bis(1-acetoxyethyl) 6-desamino-6-hydroxygriseolate
158. bis(1-propionyloxyethyl) 6-desamino-6-hydroxygriseolate
159. bis(1-butyryloxyethyl) 6-desamino-6-hydroxygriseolate
160. bis(1-pivaloyloxyethyl) 6-desamino-6-hydroxygriseolate
161. bis(1-methoxycarbonyloxyethyl) 6-desamino-6-hydroxygriseolate
162. bis(1-ethoxycarbonyloxyethyl) 6-desamino-6-hydroxygriseolate
163. bis(1-propoxycarbonyloxyethyl) 6-desamino-6-hydroxygriseolate
164. bis(1-isopropoxycarbonyloxyethyl) 6-desamino-6-hydroxygriseolate
165. bis(1-butoxycarbonyloxyethyl) 6-desamino-6-hydroxygriseolate
166. bis(1-isobutoxycarbonyloxyethyl) 6-desamino-6-hydroxygriseolate
167. diphthalidyl 6-desamino-6-hydroxygriseolate
168. bis(5-methyl-2-oxo-1,3-dioxolen-4-ylmethyl) 6-desamino-6-hydroxygriseolate
169. 7'(S)-griseolic acid
170. dimethyl 4'β-acetoxy-$O^{2},O^{7'}$-diacetyl-5'-hydrogriseolate
171. dimethyl $O^{2'},O^{7'}$-diacetyl-4'β-bromo-5'-hydrogriseolate
172. dimethyl $O^{2'},O^{7'}$-diacetyl-4'β,5'-dihydrogriseolate
173. 4'β,5'-dihydrogriseolic acid
174. dimethyl 4'β-acetoxy-$O^{2'},O^{7'}$-diacetyl-6-desamino-5'-hydro-6-hydroxygriseolate
175. dimethyl 4'α-acetoxy-$O^{2'},O^{7'}$-diacetyl-6-desamino-5'-hydro-6-hydroxygriseolate
176. dimethyl $O^{2'},O^{7'}$-diacetyl-4'β-chloro-6-desamino-5'-hydro-6-hydroxygriseolate
177. dimethyl $O^{2'},O^{7'}$-diacetyl-4'β-bromo-6-desamino-5'-hydro-6-hydroxygriseolate
178. dimethyl $O^{2'},O^{7'}$-diacetyl-6-desamino-4'β,5'-dihydro-6-hydroxygriseolate
179. 6-desamino-4'β,5'-dihydro-6-hydroxygriseolic acid
180. dimethyl $O^{2'},O^{7'}$-diacetyl-5'α-chloro-6-desamino-6-hydroxy-4'β-methoxygriseolate 181. dimethyl $O^{2'},O^{7'}$-diacetyl-5'α-bromo-6-desamino-6-hydroxy-4'β-methoxygriseolate
182. 4',7'-anhydro-5'α-bromo-6-desamino-4'α,6-dihydroxgriseolic acid
183. 4',7'-anhydro-5'α-chloro-4'α-hydroxygriseolic acid
184. 4',7'-anhydro-5'α-bromo-4'α-hydroxygriseolic acid
185. 4',7'-anhydro-4'α-hydroxy-5'α-iodogriseolic acid
186. 4',7'-anhydro-8-bromo-5'α-chloro-4'α-hydroxygriseolic acid
187. 4',7'-anhydro-5',α,8-dibromo-4'α-hydroxygriseolic acid
188. 4',7'-anhydro-8-bromo-4'α-hydroxy-5'α-iodogriseolic acid
189. dibenzhydryl 4',7'-anhydro-5'α,8-dibromo-4'α-hydroxygriseolate
190. dibenzhydryl 4',7'-anhydro-5'α-bromo-4'α-hydroxy-8-mercaptogriseolate
191. dibenzhydryl 8-mercaptogriseolate
192. 8-mercaptogriseolic acid
193. dibenzhydryl 4',7'-anhydro-5'α-bromo-4'α-hydroxy-8-methoxygriseolate
194. dibenzhydryl 8-methoxygriseolate
195. 8-methoxygriseolic acid
196. 8-bromogriseolic acid
197. 8-bromo-6-desamino-6-hydroxygriseolic acid
198. dibenzhydryl 8-bromogriseolate
199. dibenzhydryl 8-azidogriseolate
200. dibenzhydryl 8-aminogriseolate
201. 8-aminogriseolic acid
202. dibenzhydryl 4',7'-anhydro-5'α-bromo-4'α-hydroxygriseolate
203. dimethyl 4',7'-anhydro-4'α-hydroxy-5'α-iodogriseolate
204. dibenzhydryl 4',7'-anhydro-4'α-hydroxy-5'α-iodogriseolate
205. dibenzhydryl 4',7'-anhydro-5'α-bromo-6-desamino-4'α,6-dihydroxygriseolate
206. dimethyl 4',7'-anhydro-5'α-bromo-6-desamino-4'α,6-dihydroxygriseolate
207. dimethyl 4',7'-anhydro-$N^6,N^6$, $O^{2'}$-tribenzoyl-5'α-bromo-4'α-hydroxygriseolate
208. dimethyl 4',7'-anhydro-$N^6,N^6,O^{2'}$-tribenzoyl-4'α-hydroxy-5'α-iodogriseolate
209. dimethyl $O^{2'},O^{7'}$-diacetyl-4'β-chloro-5'-hydrogriseolate
210. dimethyl $O^{2'},O^{7'}$-diacetyl-5'-hydro-4'β-iodogriseolate
211. dimethyl $O^{2'},O^{7'}$-diacetyl-6-desamino-5'-hydro-6-hydroxy-4'β-iodogriseolate
212. 4',7'-anhydro-5'α-chloro-6-desamino-4'α,6-dihydroxygriseolic acid
213. 4',7'-anhydro-6-desamino-4'α,6-dihydroxy-5'α-iodogriseolic acid
214. 4',7'-anhydro-5'α-bromo-8-chloro-4'α-hydroxygriseolic acid
215. 4',7'-anhydro-8-chloro-4'α-hydroxy-5'α-iodogriseolic acid
216. 8-methylthiogriseolic acid
217. 8-benzylthiogriseolic acid
218. 8-phenylthiogriseolic acid
219. 8-hydroxygriseolic acid
220. 8-benzyloxygriseolic acid
221. 8-phenoxygriseolic acid
222. 8-methylaminogriseolic acid
223. 8-benzylaminogriseolic acid
224. 8-phenylaminogriseolic acid
225. 8-chloro-6-desamino-6-hydroxygriseolic acid
226. 8-chlorogriseolic acid
227. dipivaloyloxymethyl 8-bromogriseolate
228. diphthalidyl 8-bromogriseolate
229. bis(1-methoxycarbonyloxyethyl) 8-bromogriseolate
230. dipivaloyloxymethyl 8-bromo-6-desamino-6-hydroxygriseolate
231. diphthalidyl 8-bromo-6-desamino-6-hydroxygriseolate
232. bis(1-methoxycarbonyloxyethyl) 8-bromo-6-desamino-6-hydroxygriseolate
233. dipivaloyloxymethyl 8-mercaptogriseolate
234. dipivaloyloxymethyl 8-methoxygriseolate
235. dipivaloyloxymethyl 8-aminogriseolate
236. dipivaloyloxymethyl 4',7'-anhydro-5'α-bromo-4'α-hydroxygriseolate
237. diphthalidyl 4',7'-anhydro-5'α-bromo-4'α-hydroxygriseolate
238. bis(1-methoxycarbonyloxyethyl) 4',7'-anhydro-5'α-bromo-4'α-hydroxygriseolate
239. diphthalidyl 4',7'-anhydro-4'α-hydroxy-5'α-iodogriseolate
240. dipivaloyloxymethyl 4',7'-anhydro-4'α-hydroxy-5'α-iodogriseolate
241. bis(1-methoxycarbonyloxyethyl) 4',7'-anhydro-4'α-hydroxy-5'α-iodogriseolate
242. bis(5-methyl-2-oxo-1,3-dioxolen-4-ylmethyl) 4',7'-anhydro-4'α-hydroxy-5'α-iodogriseolate
243. bis(5-methyl-2-oxo-1,3-dioxolen-4-ylmethyl) 4',7'-anhydro-8-bromo-4'α-hydroxygriseolate
244. bis(5-methyl-2-oxo-1,3-dioxolen-4-ylmethyl) 8-bromo-6-desamino-6-hydroxygriseolate
245. bis(5-methyl-2-oxo-1,3-dioxolen-4-ylmethyl) 8-bromogriseolate
246. dimethyl $O^{2'}$-benzoyl-$O^{7'}$-(tetrahydropyran-2-yl)griseolate
247. 2'(S)-azido-2'-deoxygriseolic acid
248. 2'(S)-amino-2'-deoxygriseolic acid
249. 2'-deoxy-2'(S)-iodogriseolic acid Preferred compounds of the invention are Compounds No. 1, 2, 5, 10, 12, 15, 20, 21, 24, 26, 29, 35, 36, 37, 40, 41, 45, 47, 51, 54, 58, 62, 63, 65, 81, 82, 88, 89, 109, 110, 125, 131, 133, 138, 141, 142, 143, 144, 145, 146, 147, 148, 149, 150, 155, 156, 157, 160, 161, 162, 167, 168, 169, 171, 173, 176, 177, 179, 183, 184, 185, 186, 187, 188, 192, 195, 196, 198, 201, 202, 203, 204, 205, 206, 217, 226, 227, 230, 231, 237, 241, 242 and 247. Of these, the most preferred are Compounds No. 10, 26, 35, 36, 37, 51, 54, 58, 131, 133, 138, 141, 142, 143, 144, 148, 156, 160, 168, 169, 192, 195, 196, 201, 202 and 247.

The compounds of the invention may be prepared by any of the processes illustrated in the following reaction schemes:

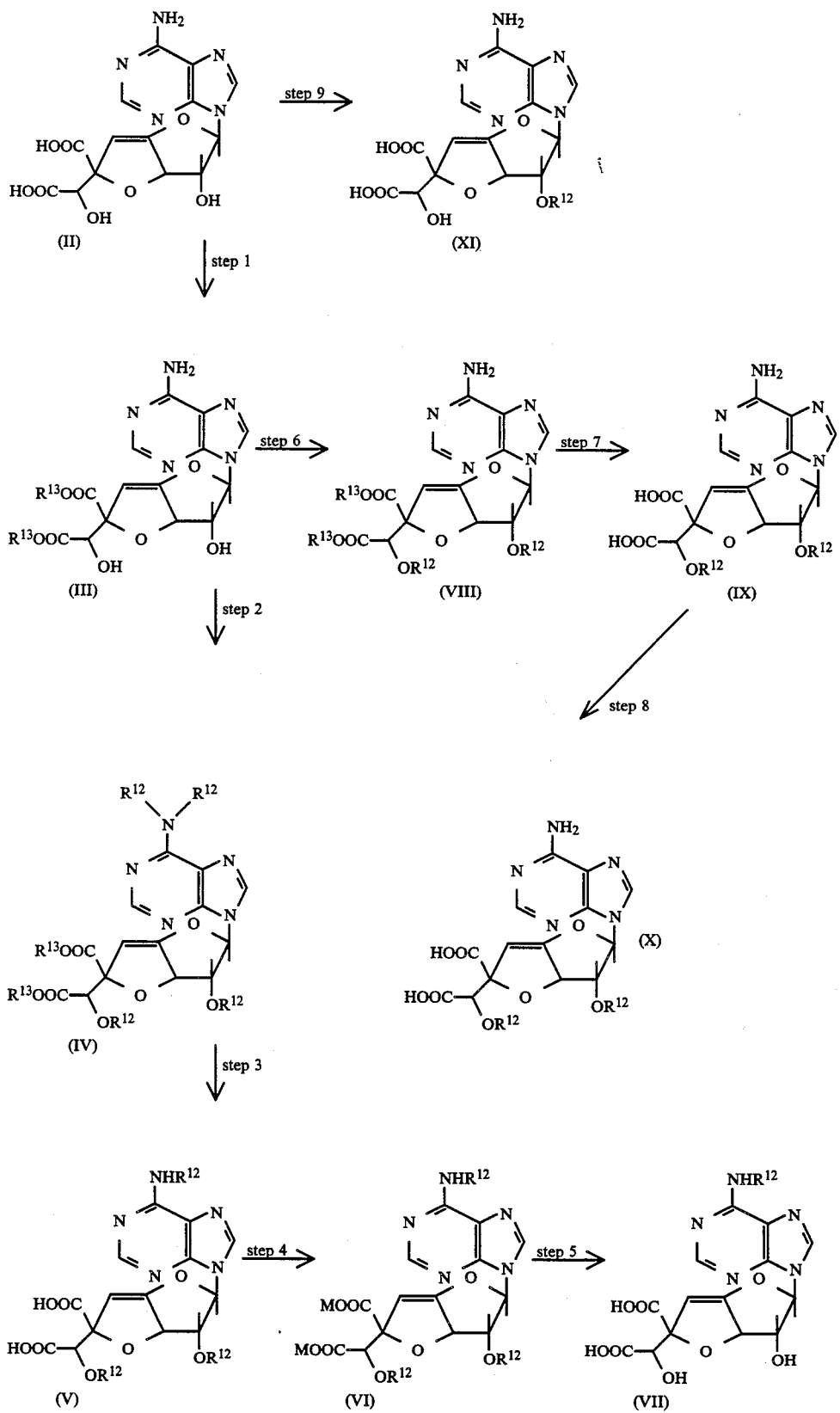

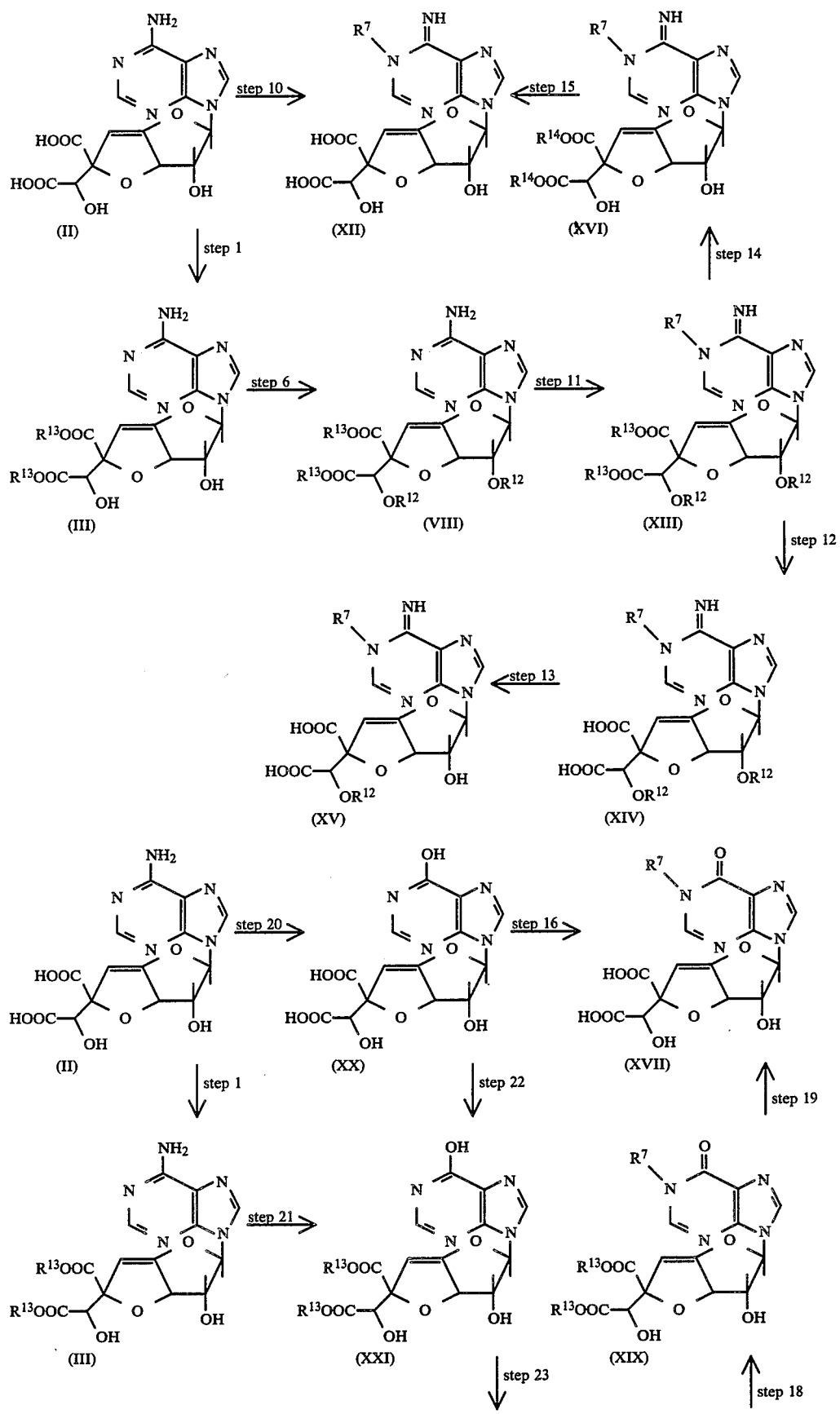

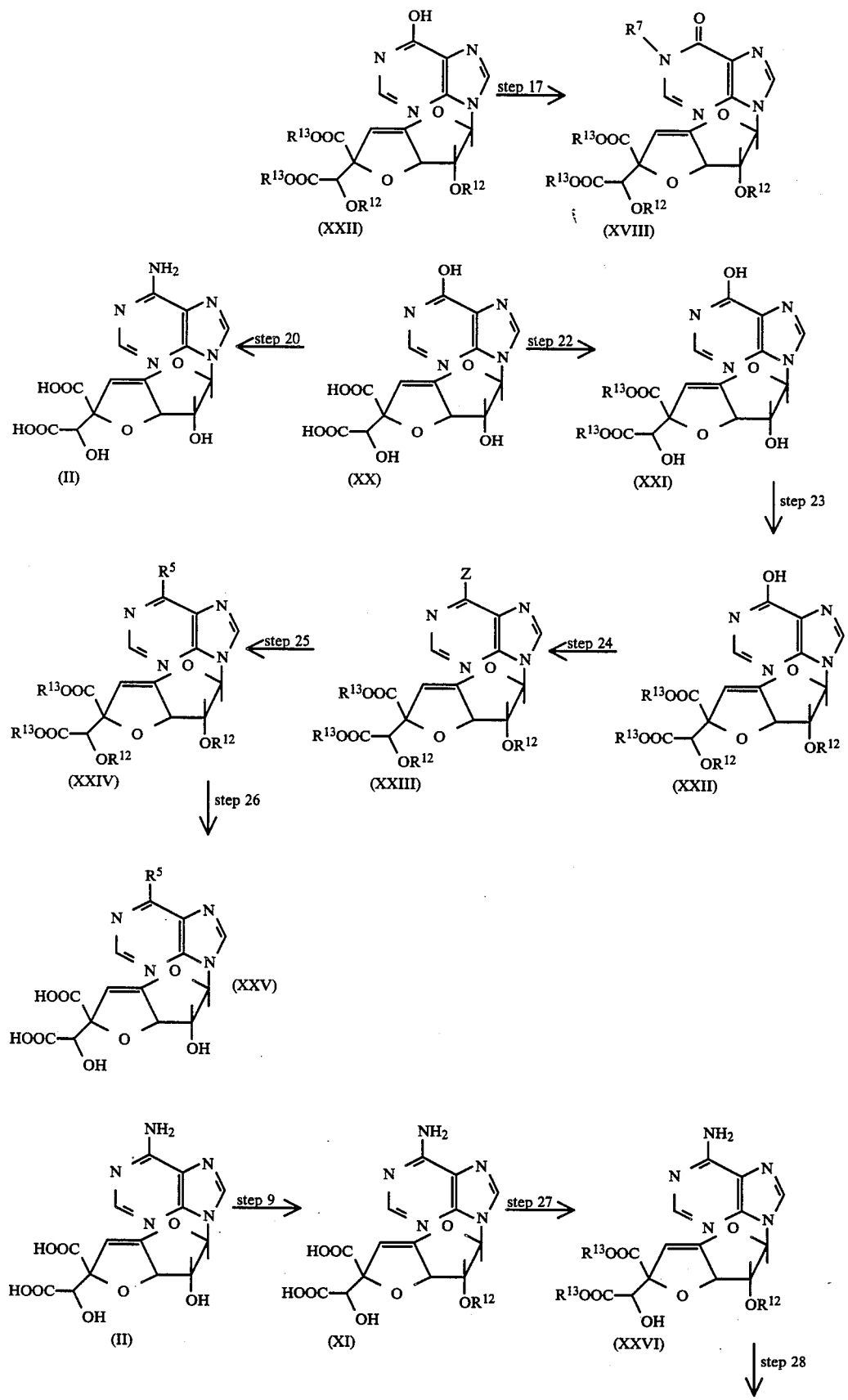

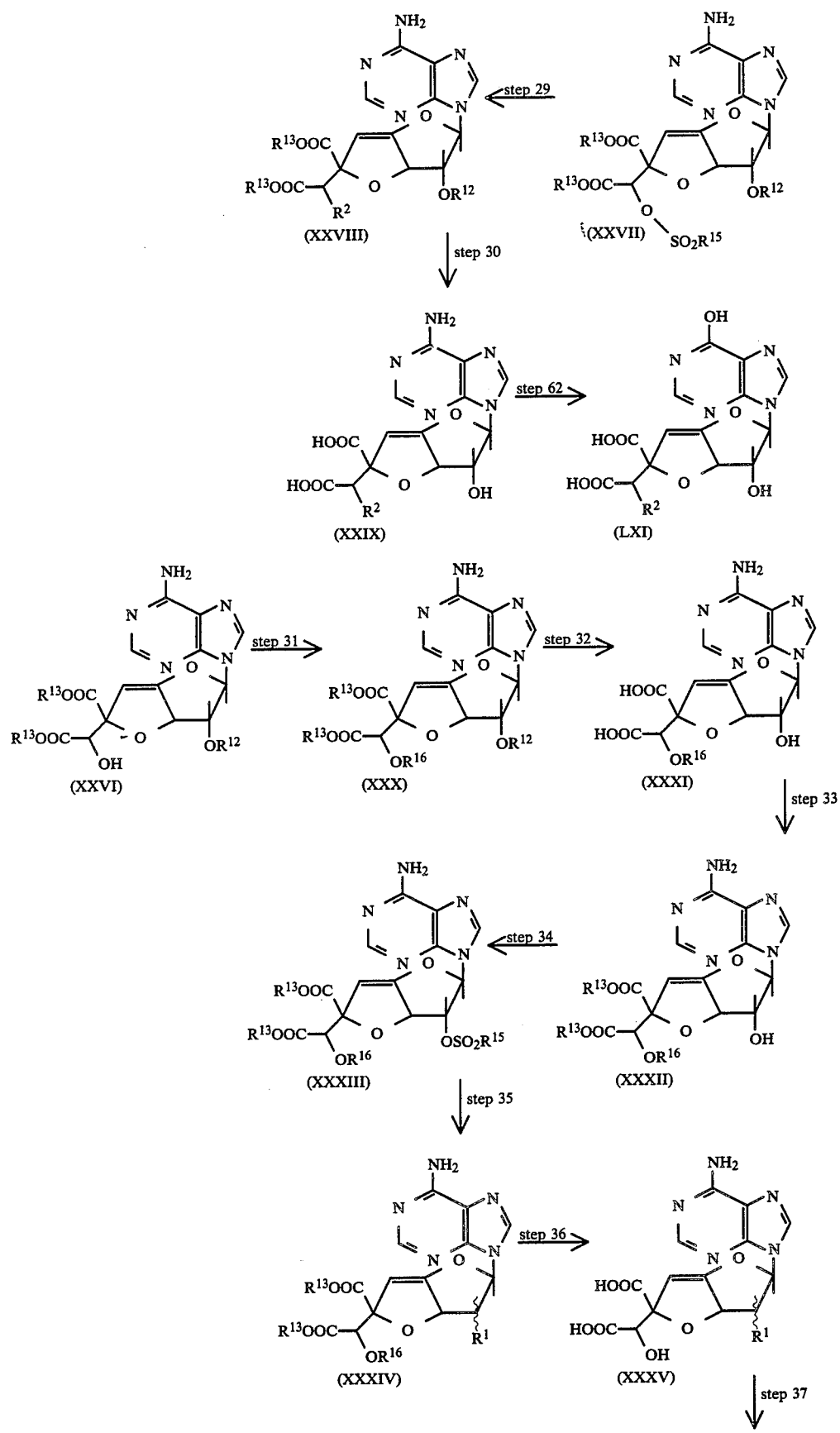

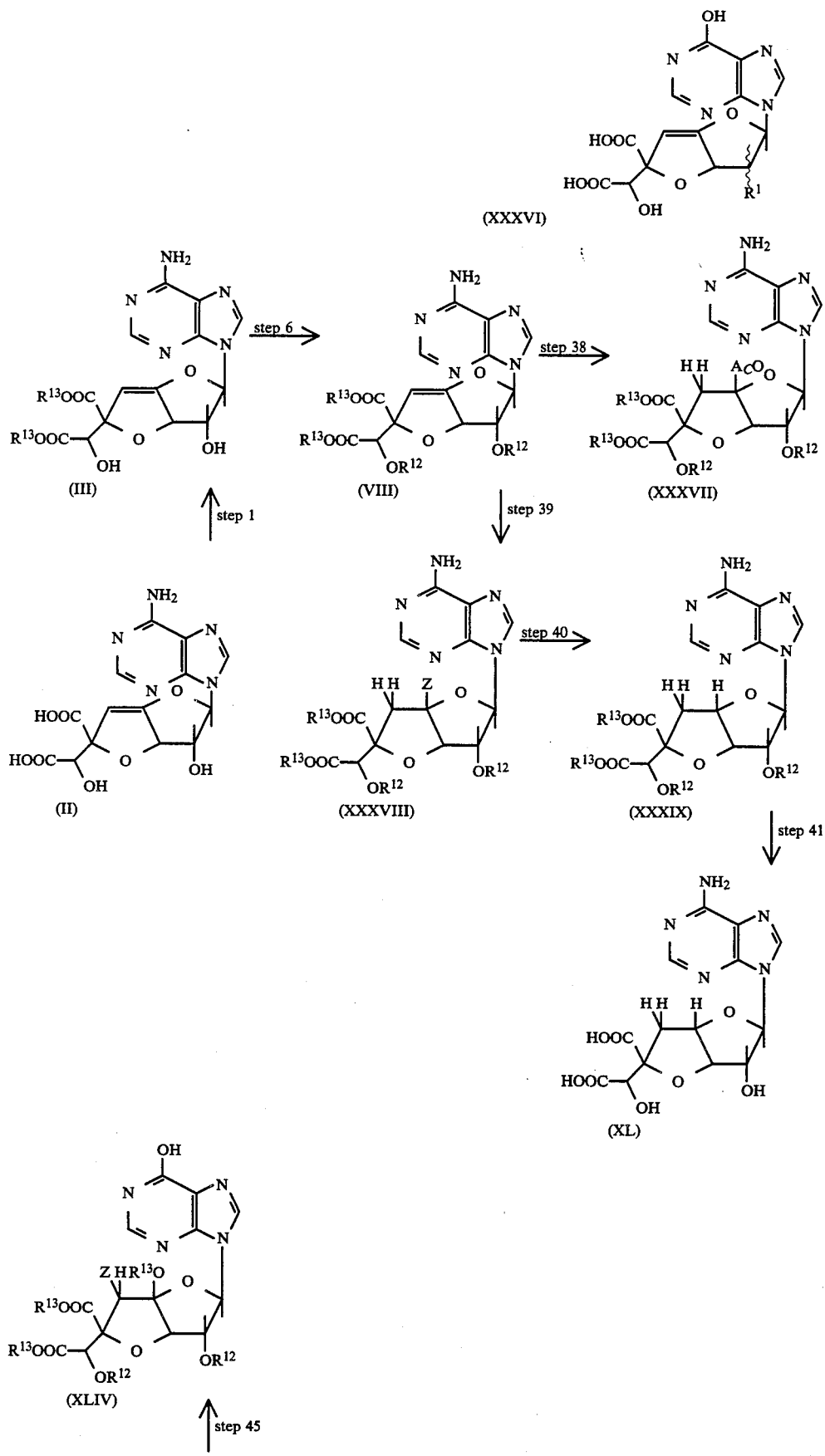

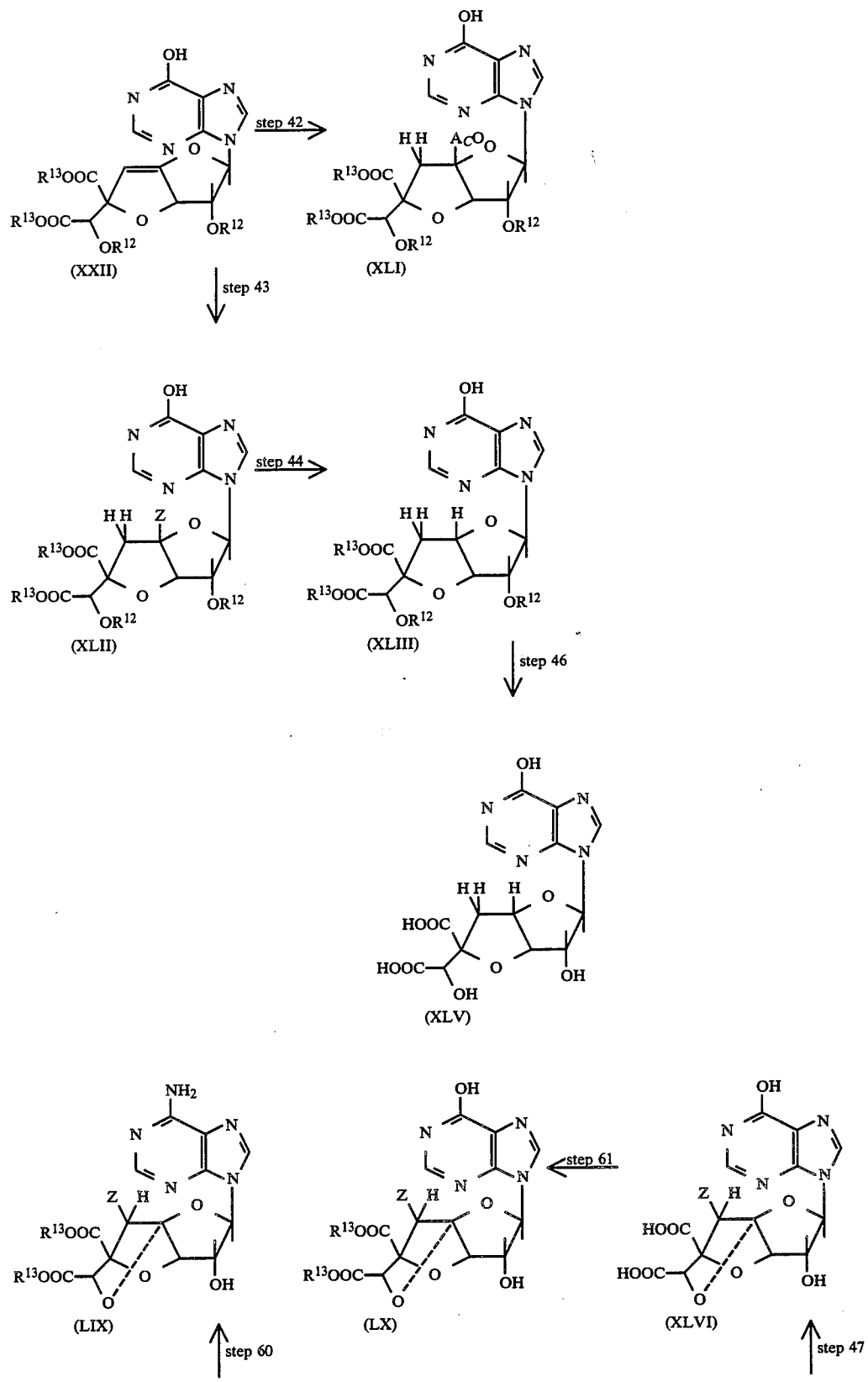

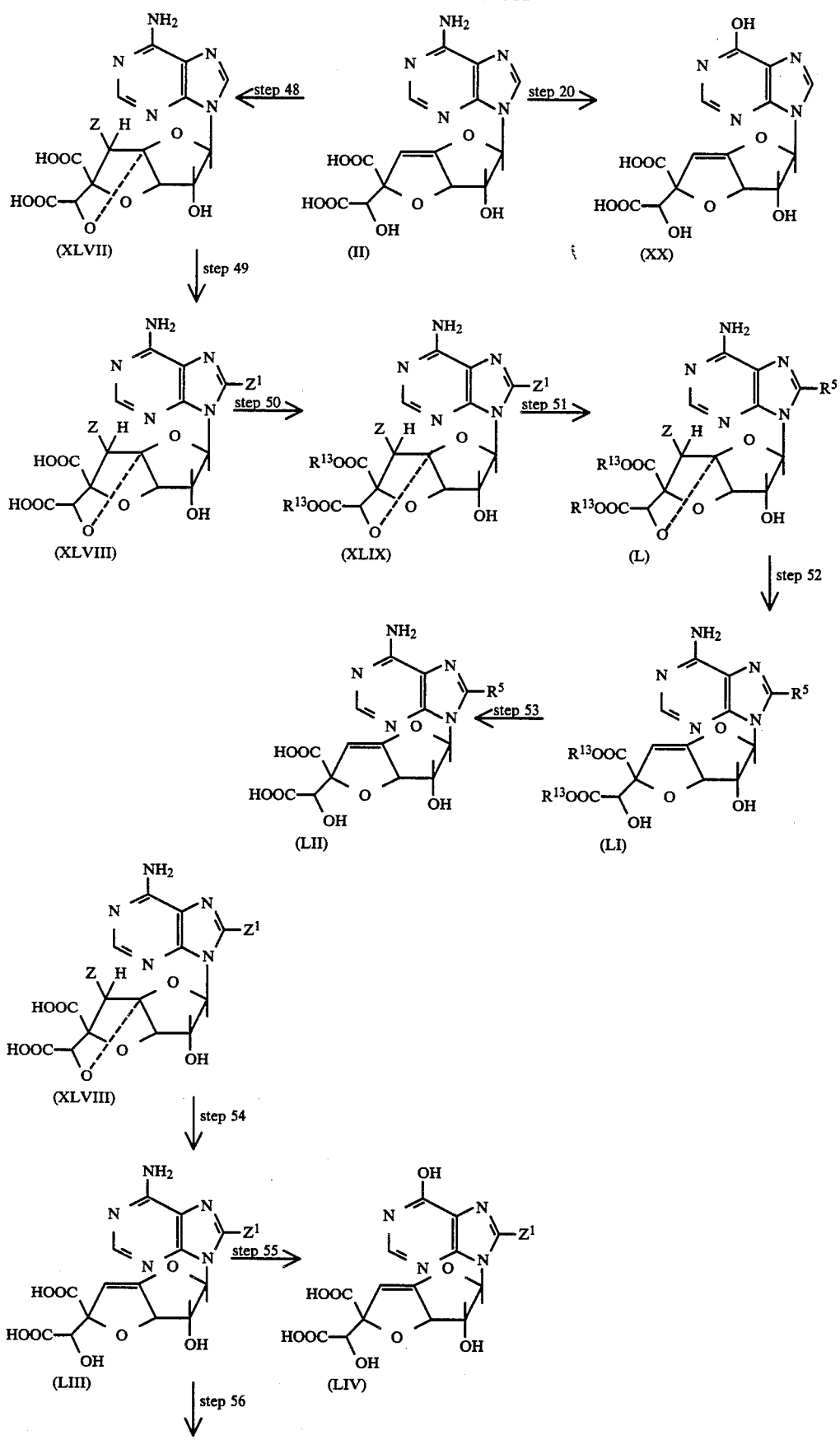

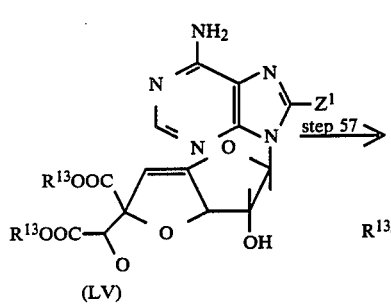 (LV)

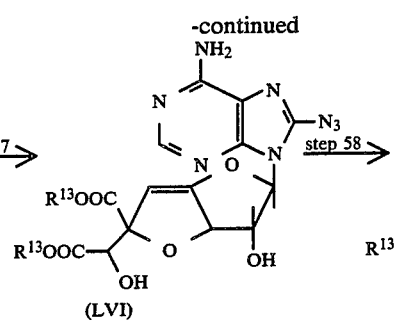 (LVI)

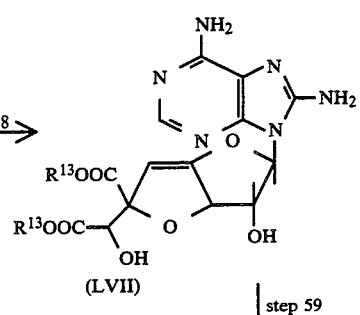 (LVII)

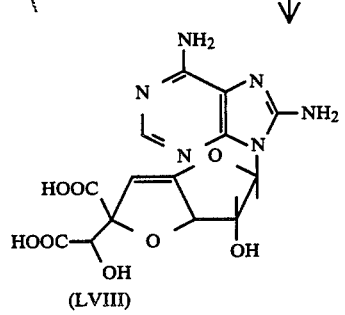 (LVIII)

In the above formulae, $R^1$–$R^8$ are as defined above. $R^{12}$ represents an acyl group, which may be any one of those acyl groups defined for $R^9$ above. $R^{13}$ represents a carboxy-protecting group and may be any one of the ester-forming groups referred to above. Where two or more groups represented by $R^{12}$ and $R^{13}$ are present in any compound, these may be the same or different, but are conveniently the same. $R^{14}$ represents a hydrogen atom or an aralkyl group (for example the benzhydryl group). $R^{15}SO_2$— represents a sulfonyl group, which may be any one of those sulfonyl groups heretofore defined for $R^9$. $R^{16}$ represents a tetrahydropyranyl group or a tri($C_1$–$C_4$alkyl)silyl group, which may be any one of those groups heretofore defined for $R^9$. $R^{17}$ represents an alkyl group and may be any one of those groups defined for $R^3$ above. Ac represents an acyl group, and may be any one of those groups defined for $R^3$ above. M represents an alkali metal atom (for example a sodium or potassium atom). Z and Z' may be the same or different and each represents a halogen atom, for example a chlorine, bromine or iodine atom.

The steps employed in the processes of the invention may be summarized as follows:

(1) Esterification of a carboxylic acid (steps 1, 22, 27, 33, 50, 56, 60 and 61)

(a) To form a benzhydryl ester

The starting material in each of these steps, which is a compound containing free carboxylic acid groups, is reacted with diphenyldiazomethane. The reaction is preferably effected in the presence of a solvent, the nature of which is not critical, provided that it has no adverse effect upon the reaction. The preferred solvent is aqueous acetone.

The reaction temperature is not particularly critical and we therefore normally carry out the reaction at a temperature within the range from 0° to 100° C., preferably, for convenience, at ambient temperature. The time required for the reaction will vary, depending upon the nature of the reagents and upon the reaction temperature; however, a period of from 15 to 24 hours will normally suffice.

(b) Esterification to a methyl ester

In this process, the carboxylic acid group or groups of the starting material are converted to corresponding methyl ester groups by reacting the carboxylic acid with diazomethane, trimethylsilyldiazomethane or 1-methyl-3-p-tolyltriazene. The reaction is preferably effected in the presence of a solvent, the nature of which is not critical, provided that it has no adverse effect upon the reaction and that it dissolves the starting material, at least to some degree. Aqueous acetone or aqueous dimethylformamide is preferred.

The reaction temperature is not particularly critical and a temperature of from 0° C. to ambient temperature is preferred. The time required for the reaction will vary, depending upon the nature of the reagents, and upon the reaction temperature. However, a period of from 1 to 10 hours will normally suffice.

(c) Esterification of a lower alkyl ester

In this process, the carboxylic acid starting material is converted to a corresponding lower alkyl ester by treatment with a mixed acid anhydride.

The mixed acid anhydride will normally be prepared by reacting a lower alcohol (such as methanol, ethanol or propanol, or other alcohol whose ester it is desired to prepare) with a conventional reagent, such as benzoyl chloride or chloroethyl carbonate.

The reaction is preferably effected in the presence of a solvent, the nature of which is not critical, provided that it has no adverse effect upon the reaction. In general, we prefer to employ as the solvent the alcohol whose ester is to be prepared.

The reaction temperature is not particularly critical and may suitably be in the range of from −20° C. to +100° C.; but, in order to avoid side reactions, a temperature of from −10° C. to ambient temperature is preferred. The time required for the reaction will vary, depending upon the nature of the reagents and on the reaction temperature. For example, where the reaction is carried out at ambient temperature, it will normally require about 15 hours.

(2) Acylation process

(a) Complete acylation (steps 2 and 23)

In this process, all positions where acylation is possible are acylated. The starting material is reacted with a conventional acylating agent, for example an acid halide (such as acetyl chloride, butyryl chloride, palmitoyl chloride or benzoyl chloride) or an acid anhydride (such as acetic anhydride or benzoic anhydride). The reaction is preferably effected in the presence of an acid-binding agent, such as triethylamine or pyridine.

The reaction is preferably effected in the presence of a solvent, the nature of which is not critical, provided that it has no adverse effect upon the reaction. Where pyridine is employed as the acid-binding agent, it is preferably used in sufficient excess to serve also as the reaction solvent.

The reaction temperature is not particularly critical and we prefer to carry out the reaction at a temperature within the range from 0° C. to ambient temperature. The time required for the reaction will vary depending upon the reaction temperature and the nature of the reagents, but a period of from 1 to 15 hours will normally suffice.

(b) Partial acylation (step 6)

In this process, the hydroxy groups, but preferably not the group at the $N^6$-position, are acylated by reacting the starting material with a suitable acylating agent. The acylating agent is preferably an acid anhydride, the nature of which will depend upon the acyl group which it is desired to introduce, and the reaction is effected in the presence of an inorganic carbonate (such as potassium carbonate) as the acid-binding agent.

The reaction is preferably effected in the presence of a solvent, the nature of which is not critical, provided that it has no adverse effect upon the reaction. A lower ketone, such as acetone, is preferred.

The reaction temperature is not particularly critical, although a temperature of from 0° C. to 100° C. is preferred. The reaction is normally carried out at around the boiling point of the solvent. The time required for the reaction will vary, depending upon the reagents, the reaction temperature and the solvent. For example, where acetone is employed as the solvent and the reaction is carried out under reflux, the reaction time will normally be from 5 to 20 hours.

(c) Partial acylation (step 9)

In this process, only the hydroxy group at the 2'-position is acylated. This is achieved by slowly adding a base (such as sodium hydroxide) to the reaction solution until the pH reaches a value within the range from 10–13. Subsequently, the acylating agent (which may be any one of those described above) is added. Alternatively, the starting material is dissolved in a buffer solution of pH 10–13 and then the acylating agent is added.

The reaction is preferably effected in the presence of a solvent, the nature of which is not critical, provided that it has no adverse effect upon the reaction. For some purposes, a solvent immiscible with water may be preferred. We normally prefer to employ a mixture of ethyl acetate and water.

The reaction temperature is not particularly critical, but we normally prefer to carry out the reaction at a temperature from −20° C. to +50° C. The temperature achieved by ice-cooling is particularly preferred. The time required for the reaction will vary, depending upon the nature of the reagents and the reaction temperature. For example, at temperatures between that of ice-cooling and ambient, a period of from 1 to 10 hours will normally suffice.

(3) Ester hydrolysis

(a) Hydrolysis of the benzhydryl ester (steps 3, 7, 12, 15, 19, 30, 36, 41, 46, 53 and 59)

In this process, benzhydryl groups, which serve as carboxy-protecting groups, are removed by acidification. The acid employed is preferably trifluoroacetic acid. The reaction is preferably effected in the presence of a solvent, the nature of which is not critical, provided that it has no adverse effect upon the reaction. Aromatic hydrocarbon solvents (such as anisole) are preferred, since these allow the reaction to proceed smoothly, without side reactions.

The reaction temperature is not particularly critical, although a temperature within the range from −20° C. to +50° C. is preferred, most preferably a temperature from 0° C. to ambient. The time required for the reaction will vary, depending upon the reagents and upon the reaction temperature but, for example, at room temperature a period of from 1 to 20 hours will normally suffice.

(b) Hydrolysis of alkyl esters (steps 14+15, 18+19, 26, 30, 36, 41, 46, 53 and 59)

In this process, the lower alkyl ester, of which the lower alkyl group acts as a carboxy-protecting group, is hydrolysed under basic conditions. Where the starting material also contains an acyloxy group, this may similarly be hydrolysed to a free hydroxy group. The reaction is preferably effected in an aqueous medium, preferably employing an aqueous solution of an alkali, for example aqueous sodium hydroxide, suitably at a 1N concentration.

The reaction temperature is not particularly critical and we generally prefer to carry out the reaction at about ambient temperature, at which it requires from 1 to 15 hours.

(4) Deacylation

(a) Complete deacylation (steps 14, 18, 30 and 36)

In this process, acyloxy groups are converted to hydroxy groups. If the carboxylic acid groups of the starting material are unprotected or have been converted to alkyl ester groups, the reaction temperature and reaction time are not particularly critical. If an aqueous alkali (such as 1N aqueous sodium hydroxide) is employed, the acyl groups are removed and the esters are hydrolysed simultaneously, as in process (3). However, where the carboxylic acid groups of the starting material are protected with benzhydryl groups, we prefer to carry out the reaction using a methanolic solution of ammonia (preferably about 20% w/v) under ice-cooling for a period of from 10–100 minutes; this will remove acyl groups from acyloxy groups, but will keep the benzhydryl groups intact.

(b) Partial deacylation (steps 8 and 13)

In this process, an acyloxy group at the 2'-position of the starting material is removed, but other acyl groups are left intact. The reagent employed is methanolic ammonia, suitably at a concentration of about 20% w/v and this will conveniently serve as the reaction solvent. The temperature is not particularly critical, but is preferably within the range from −30° C. to +50° C. A temperature of from 0° C. to ambient temperature is generally preferred. The time required for the reaction will vary, depending upon the reagents and the reaction temperature, but a period of from 10 to 200 minutes will normally suffice.

(c) Partial deacylation (step 5)

In this process, the starting material has acyl groups at the $N^6$-position, as well as at the 2'- and 7'-positions. The acyl groups at the 2'- and 7'-positions are to be removed, but that at the $N^6$-position is to be left intact. In this case, the reagent employed is preferably an alkaline solution having insufficient basicity to liberate an amino group from the amido group at the $N^6$-position, and 1N aqueous sodium hydroxide is preferably employed. The reaction temperature is not particularly critical and the reaction is preferably effected at ambient temperature, at which a period of from 10 to 20 hours will normally be required.

(5) Alkylation (steps 10, 11, 16 and 17)

In this process, the $N^1$-position of the starting material is alkylated or aralkylated, whilst the carboxylic acid groups and the hydroxy groups are protected or unprotected. The reagent employed is preferably an alkyl halide (such as methyl iodide or ethyl bromide) or an aralkyl halide (such as benzyl bromide or phenacyl bromide). In some cases, it may be desirable to employ a carbonate (for example potassium carbonate) as an acid-binding agent.

The reaction is preferably carried out in the presence of a solvent, the nature of which is not critical, provided that it has no adverse effect upon the reaction. A polar solvent, such as dimethylformamide, is preferred.

The reaction temperature will vary depending upon the nature of the reagents. When a compound having unprotected carboxylic acid and hydroxy groups is employed, the reaction is preferably effected at ambient temperature. On the other hand, where these groups are protected, the reaction temperature is normally about 70° C. The time required for the reaction will, of course, likewise vary depending upon the reagents, and will also depend upon the reaction temperature. At ambient temperature, the reaction will normally require from 1 to 7 days, whilst the reaction at 70° C. will normally require from 1 to 20 hours.

(6) Deamination (steps 20, 21, 37, 55 and 62)

In this process, the amino group at the 6-position of the starting material is converted to a hydroxy group. The reagent employed is preferably a nitrite (such as sodium nitrite) and it is preferably employed under acidic conditions. The acidity is preferably supplied by acetic acid and the reaction solvent is then preferably aqueous acetic acid. If the starting material is soluble only with difficulty, an acetic acid buffer solution of pH 4 may be more preferred. The reaction temperature is preferably within the range from 0° C. to ambient temperature and the time required for the reaction will normally vary from 10 to 50 hours.

(7) Halogenation at the 6-position (step 24)

In this process, the hydroxy group at the 6-position of the starting material is halogenated, whilst the remaining hydroxy groups and the carboxy groups are suitably protected.

The halogenating agent is not particularly critical and any such agent commonly used for the halogenation of hydroxy groups in a heterocyclic compound may be employed in this process. We prefer to employ phosphorus oxychloride or phosphorus oxybromide. The presence of an acid-binding agent may have a catalytic effect, suitable such agents being aromatic tertiary amines (such as diethylaniline or dimethylaniline) or aliphatic tertiary amines (such as triethylamine).

The reaction is preferably effected in the presence of a solvent, the nature of which is not critical, provided that it does not adversely affect the reaction. In general, the halogenating agent itself may serve as the reaction solvent, as may the acid-binding agent. In some cases, however, an ester (such as ethyl acetate) may be employed as solvent, together with an excess of the halogenating agent. The reaction is preferably effected at the boiling point of the solvent. The time required for the reaction will vary, depending upon the reagents and reaction time. For example, with phosphorus oxychloride as the halogenating agent, a period of from 10 minutes to 5 hours will normally suffice.

(8) Substitution at the 6- or 8-position (steps 25, 51 and 57)

In this process, a griseolic acid derivative having a desired substituent at the 6- or 8-position is prepared by reacting a corresponding derivative (in which the amino group at the 6-position has been replaced by a halogen atom or having a halogen atom at the 8-position) with one of various types of nucleophilic agent. Suitable such agents include sodium methoxide, sodium hydrosulfide, sodium azide, hydrazine, methylamine, dimethylamine, $\beta$-hydroxyethylamine, benzylamine, naphthylamine, piperidine or morpholine. When an amine is employed as the nucleophilic agent, the reaction will proceed smoothly using an excess of the amine, and an acid-binding agent is not necessary. However, any nucleophilic agent other than an amine will normally require the presence of an acid-binding agent (such as those exemplified in previous processes) provided that it does not itself act as a nucleophilic agent.

The reaction is preferably effected in the presence of a solvent, the nature of which is not critical, provided that it has no adverse effect upon the reaction. A lower alcohol, such as methanol or ethanol, and dimethylformamide are preferred.

The reaction temperature is not particularly critical and a temperature from ambient to the boiling point of the solvent is preferably employed. The time required will vary depending upon the nucleophilic agent and the reaction temperature; for example, reaction at ambient temperature will normally require about 20 hours, whilst reaction at the boiling point of the solvent will normally require about 6 hours.

(9) Pyranylation (step 31)

In this process, a pyranyl group is introduced onto the hydroxy group of the starting material. The preferred agent is 3,4-dihydropyran and the reaction is preferably effected in the presence of an acid catalyst, such as hydrochloric acid. The reaction is preferably also effected in the presence of a solvent, the nature of which is not critical, provided that it does not have any adverse effect upon the reaction. Suitable solvents include chloroform, ethyl acetate, dioxane and dimethylformamide. The reaction temperature is not particularly critical and ambient temperature is preferred. The reaction will normally require from 1 to 20 hours.

(10) Silylation (step 31)

In this process, a trialkylsilyl group (e.g. the t-butyldimethylsilyl group) is introduced onto the hydroxy group at the $O^{7'}$-position. The silylating agent is preferably a trialkylsilyl halide (e.g. t-butyl-dimethylsilyl chloride) and the reaction is preferably effected in the presence of a catalyst, such as imidazole. The reaction solvent is preferably a polar solvent, such as dimethylformamide. The reaction is preferably effected at ambient temperature, at which a period of from 2 to 30 hours will normally be required.

(11) Hydrolysis of esters (step 32)

In this process, all ester groups are completely hydrolysed, except the protecting group at the 7'-position, which is stable under basic conditions. The hydrolysis is preferably achieved using a 1N aqueous sodium hydroxide solution, at ambient temperature for 1-15 hours.

(12) Sulfonylation (steps 28 and 34)

In this process, the hydroxy groups at the 2'- and 7'-positions of the starting material are sulfonylated selectively or simultaneously. The reaction is preferably effected using a sulfonyl halide, such as methanesulfonyl chloride, p-toluenesulfonyl chloride or trifluoromethanesulfonyl chloride as the sulfonylating agent. The reaction is preferably effected in the presence of an acid-binding agent (such as pyridine or dimethylaminopyridine) and in the presence of a solvent. The solvent is not particularly critical, provided that it does not interfere with the reaction; methylene chloride or chloroform is preferred.

The reaction temperature is not particularly critical, a temperature from $-10°$ C. to ambient being preferred. The time required for the reaction will vary, depending upon the reagents and the reaction temperature, but a period of from 1 to 20 hours will normally suffice.

(13) Substitution at the 2'- or 7'-position (steps 29 and 35)

In this process, the sulfonyl group at the 2'- or 7'-position is replaced by an appropriate nucleophilic agent, as mentioned in process (8) above. Where an amine is employed as the nucleophilic agent, it is preferably employed in excess. Where the nucleophilic agent is not an amine, the presence of a suitable acid-binding agent (such as pyridine, triethylamine, potassium carbonate or sodium carbonate) is preferred.

The reaction is preferably effected in the presence of a solvent, the nature of which is not critical, provided that it does not adversely affect the reaction. A polar solvent, such as dimethylformamide, dimethyl sulfoxide, hexamethylphosphoric triamide or triethyl phosphate, is most preferred.

The reaction temperature will vary, depending upon the reagents and solvents employed, but it is not particularly critical and a temperature within the range from 0° C. to 150° C. is preferred. Where a trifluoromethanesulfonyl derivative is the starting material and hexamethylphosphoric triamide is the solvent, ambient temperature is preferred. The time required for the reaction will vary, depending upon the reagents and reaction temperature. However, the reaction in hexamethylphosphoric triamide mentioned above would generally require from 1 to 100 hours at ambient temperature. Compounds which have an azido group, chlorine atom or bromine atom at the 2'- or 7'-position can be reduced to the corresponding compounds having an amino group or hydrogen atom at the said position.

(14) Salt-forming process (step 4)

In this process, an alkali metal salt is prepared by conventional means. The carboxylic acid starting material is dissolved in an aqueous organic solvent (such as a mixture of water and ethyl acetate). To this is added a solution of an alkali metal carbonate or bicarbonate (such as an aqueous solution of sodium bicarbonate or of potassium carbonate). This is preferably effected at a temperature of from 0° C. to ambient. On adjusting the pH to a value of approximate neutrality (pH 7), a precipitate of the desired salt appears and this may be filtered off.

(15) Addition of a carboxylic acid across the double bond (steps 38 and 42)

In this process, a carboxylic acid, the nature of which will depend upon the nature of the group which it is desired to introduce, is added across the double bond between the 4'- and 5'-positions of griseolic acid. The reaction is preferably effected in the presence of a solvent, whose nature is not critical, provided that it is capable of dissolving, at least to some extent, both reagents and provided that it does not interfere with the reaction. Where a carboxylic acid such as acetic acid is employed as the reagent, this can usefully serve as the reaction solvent.

In order to promote the reaction, a strong acid (such as anhydrous hydrochloric acid, hydrobromic acid, hydroiodic acid, sulfuric acid or trifluoromethanesulfonic acid) or a catalyst (such as platinum oxide) may be added to the reaction mixture, together with the carboxylic acid (for example acetic acid or propionic acid).

The reaction temperature is not particularly critical, a temperature within the range from 0° C. to 100° C. being preferred. The time required for the reaction will vary, depending upon the reaction temperature and the reagents; a period of from 1 hours to 3 days will normally suffice.

(16) Addition of a hydrohalic acid to the double bond (steps 39 and 43)

In this process, a hydrohalic acid is added across the double bond of griseolic acid. The hydrohalic acid will normally be hydrochloric acid, hydrobromic acid or hydroiodic acid, depending upon the halogen atom which it is desired to introduce. The reaction is preferably effected in the presence of a solvent, the nature of which is not critical, provided that it has no adverse effect upon the reaction. An organic acid, such as acetic acid, is preferred. The reaction temperature is not critical and is preferably from 0° C. to ambient temperature, although heating to 80°-100° C. may be desirable in some circumstances. The time required for the reaction will vary, depending upon the reagents, reaction solvent and reaction temperature, but a period of from 1 to 72 hours will normally suffice.

(17) Addition of a halogen atom and an alkoxy group across the double bond (step 45)

In this process, an alkoxy group and a halogen atom are added across the double bond of griseolic acid. In general, the reaction is effected by dissolving the starting material in an alcohol (such as methanol or ethanol), which serves as both reagent and reaction solvent, and adding a halogenating agent, such as fluorine, chlorine, bromine, iodine, N-chlorosuccinimide, N-bromosuccinimide or N-iodosuccinimide. The reaction temperature is not particularly critical and a temperature of from 0° C. to about ambient is preferred. The time required for the reaction will vary, depending upon the reaction temperature and the reagents, but a period of from 1 to 30 minutes will normally suffice.

(18) Reduction of halogen derivatives (steps 40 and 44)

In this process, the halogen group at the 4'-position of a griseolic acid derivative is reduced. The reagent employed may be any reagent commonly used for the reduction of halogen atoms, tributyltin hydride or zinc powder being preferred.

The reaction is normally effected in the presence of a solvent, which is not particularly critical, provided that it does not interfere with the reaction. Where tributyltin hydride is used as the reagent, the solvent is preferably an aromatic hydrocarbon, such as benzene, toluene or xylene. Where zinc powder is used as the reagent, a lower aliphatic carboxylic acid, such as aqueous acetic acid, or an alcohol, such as methanol or ethanol, is preferred.

Where tributyltin hydride is employed, the reaction is preferably effected at about the boiling point of the reaction solvent. Where zinc powder is employed, the reaction may be carried out at a temperature from ambient to 100° C. The time required for the reaction similarly varies: where tributyltin hydride is used, a period of from 2 to 10 hours is required; where zinc powder is used, a period of from 2 to 20 hours is required.

(19) Synthesis of 4',7'-anhydro compound (steps 47 and 48)

In this process, a compound having a halogen atom at the 5'-position and having an anhydro (ether) bond between the 4'- and 7'-positions is prepared from a griseolic acid derivative having a 4',5'-double bond. The reaction is effected by contacting the starting material with a halogen (such as fluorine, chlorine, bromine or iodine) in an aqueous alkaline solution of pH greater than 12. A suitable alkali is an alkali metal hydroxide (such as sodium hydroxide or potassium hydroxide).

The reaction is preferably effected in the presence of a solvent, normally water. However, where a water-insoluble reagent, such as iodine, is used, a mixture of an alcohol (e.g. methanol) with water may be employed. The reaction is preferably effected at a temperature from 0° C. to ambient and the time required for the reaction, which will vary depending upon the reagents an the reaction temperature, is usually from 30 minutes to 6 hours.

(20) Halogenation at the 8 position (step 49)

In this process, a griseolic acid derivative having a halogen atom at the 8-position is prepared. The reagent employed may be any halogenating agent capable of halogenating the 8-position of an adenine derivative. We prefer bromine water in a pH 4 buffer solution, such as a 1M acetate buffer. The reaction solvent is preferably an aqueous solution of pH 4 and the reaction is preferably effected at a temperature of from 0° C. to about ambient, at which the time required is normally from 1 to 10 hours.

(21) Reinstatement of double bond (steps 52 and 54)

In this process, a double bond is produced between the 4'- and 5'-positions by reacting a 4'α-hydroxy-4',7'-anhydrogriseolic acid derivative having a halogen atom at the 5'-position either under acidic conditions or with zinc powder.

Where the halogen atom at the 5'-position is chlorine or bromine, the starting material is heated under reflux with zinc powder in an aqueous solvent, such as aqueous methanol or aqueous ethanol. Alternatively, it is reacted with zinc powder at a temperature from ambient temperature to 80° C. in an aqueous organic acid, such as aqueous acetic acid.

Where the halogen atom at the 5'-position is iodine, the double bond may be introduced by the same process as described in the preceding paragraph for the case where the halogen atom is chlorine or bromine. Alternatively, an aqueous solution of the starting material may be acidified to a pH value of from 0 to 3 and then allowed to stand at 0° C. to 60° C. in the presence or absence of an inorganic salt, such as potassium iodide or sodium hydrogen sulfite.

(22) Conversion of an azido group to an amino group (step 58)

In this process, the azido group at the 8-position of a griseolic acid derivative is converted to an amino group. The reaction may be carried out by treating the starting material in a medium comprising an alcohol (such as methanol or ethanol) with hydrogen in the presence of a catalyst, such as palladium-on-carbon. Alternatively, the starting material may be allowed to stand at room temperature in an organic base (such as pyridine) containing hydrogen sulfide for a period of from 10 to 30 hours.

After completion of any of the above reactions, the desired compound can be separated from the reaction mixture by conventional means. For example, one suitable recovery procedure comprises: if necessary, washing the reaction mixture with water; distilling off the solvent under reduced pressure; and then purifying the product by various conventional means, such as recrystallization, column chromatography or preparative thin layer chromatography.

7'-Deoxygriseolic acid may also be prepared by cultivating a 7'-deoxygriseolic acid-producing microorganism of the genus Streptomyces, especially *S. griseoaurantiacus* No. 43894 (FERM P-5223), in a nutrient medium therefor and then recovering 7'-deoxygriseolic acid from the culture broth.

*S. griseoaurantiacus* No. 43894 is the strain of microorganism identified in European patent specification No. 29,329 and U.S. Pat. No. 4,460,765 as SANK 63479 and was deposited on Oct. 9, 1979 at the Fermentation Research Institute, Agency of Industrial Science and Technology, Japan, whence it is available under the Accession No. FERM P-5223.

As is well-known, the properties of Actinomycetes including Streptomyces, strains are not fixed and they readily undergo mutation both through natural causes and as a result of artificial mutation. Although there is described the production of 7'-deoxygriseolic acid especially by the cultivation of the above identified *Streptomyces griseoaurantiacus* strain, the use of mutants of this organism and generally of any Streptomyces strain which is capable of producing 7'-deoxygriseolic acid is also possible.

The cultivation of the 7'-deoxygriseolic acid-producing microorganism, in accordance with this process of the invention, can be performed under the conditions conventionally employed for the cultivation of Actinomycetes strains, e.g. as described generally in U.S. Pat. No. 4,460,765. Shaken culture in a liquid medium or a solid cultivation method are preferred. However, detailed variations within the conditions broadly described below are possible in order to favor the production of one of griseolic acid and 7'-deoxygriseolic acid over the other.

The nutrient medium used for the cultivation can be a composition such as is conventionally used for the cultivation of Actinomycetes. Thus, it would contain an assimilable carbon source and an assimilable nitrogen source. Suitable assimilable carbon sources include: a concentrated solution of a sugar (e.g. of sucrose and/or invert sugar or of a mixture of sucrose with another sugar, such as glucose or corn syrup), starch, dextrose, mannitol, fructose, galactose or rhamnose or any combination of two or more thereof. The nitrogen source may be: an organic or inorganic compound, e.g. ammonium chloride, ammonium sulfate, urea, ammonium nitrate or sodium nitrate, or natural products, such as peptone, meat extract, yeast extract, dried yeast, live yeast, corn steep liquor, soybean meal, soybean flour, casamino acid or soluble vegetable proteins. A single such nitrogen source or a combination of any two or more may be employed. In addition, the nutrient medium may also contain inorganic salts (such as potassium chloride, calcium carbonate or phosphoric acid salts), optionally together with other organic or inorganic substances to promote the growth of the microorganism or its production of 7'-deoxygriseolic acid.

The method of cultivation may be a liquid cultivation method, with reciprocal or rotatory shaking, or a solid cultivation method, a deep-stirring cultivation method being particularly preferred. Although the microorganism will grow over a wide range of temperatures, it is particularly preferred to effect the cultivation at a temperature of from 20° to 35° C. and at a substantially neutral pH value. When a liquid cultivation method is employed, the cultivation is normally effected for a period of from 48 hours to 120 hours, during which time 7'-deoxygriseolic acid is formed and accumulates in the culture broth. The progress of the cultivation may be monitored and the content of 7'-deoxygriseolic acid in the broth estimated by determining the enzyme inhibitory activity of the broth. After completion of deep liquid cultivation, the culture broth will generally show an inhibitory activity of from 70 to 85%.

BIOLOGICAL ACTIVITY

The compounds of the invention have various valuable pharmacological activities. Thus, they show a marked ability to inhibit the activity of PDE, both cAMP PDE and cGMP (cyclic guanosine monophosphate) PDE; the ability to promote the recovery of cerebral function after anoxia-induced brain injury; they improve the sugar metabolism and high energy phosphate metabolism in the brain of rats with cerebral ischaemia; they restore the flexibility of erythrocytes which has been decreased by acidosis; they increase the cerebral blood flow in rabbits; they promote recovery of brain function in rats with cerebral ischaemia; and when combined with anti-cancer agents or insulin, they potentiate their effects. These activities are illustrated below.

The compounds of the invention are identified by the numbers assigned to them in the foregoing list.

Toxicity

The compounds under test were griseolic acid and Compounds No. 26 and 51 from the list of compounds of the invention set out hereinabove. The test animals were male rats of the Fisher strain. The rats were employed in groups of five for each test.

The compounds under test were administered at single daily doses of 50 mg/kg or 100 mg/kg throughout the four days of the test.

At a dose of 50 mg/kg, all three test compounds showed a mortality of 0/5 at the end of the test (i.e. of the 5 rats in each test group, none died). At a dose of 100 mg/kg, the mortality exhibited by griseolic acid was 3/5 (0/5 for the first two days and 3/5 after day 3). The mortalities for the two compounds of the invention at 100 mg/kg were 0/5 by the end of the test, that is no mortality.

These results suggest that the compounds of the invention are probably less toxic than griseolic acid.

Phosphodiesterase (PDE) inhibitory activity

Thirty-four of the compounds of the invention were tested, identified by the numbers from the list hereinabove, together with theophylline as a comparison.

The test was carried out following essentially the method of A. L. Pichard and Y. U. Chung [Journal of Biological Chemistry, 251, 5726–5737 (1976)]. A crude enzymatic solution derived from rat brains was used as the source of cAMP PDE.

$^{14}$C-labeled cAMP was used as the substrate. It was employed in a 0.2M Tris-hydrochloric acid buffer solution (pH 8.0) in an amount sufficient to provide a final concentration of 0.14 $\mu$M. "Tris" is tris(hydroxymethyl)aminomethane. The substrate solution was mixed with an appropriate amount of the compound under test dissolved in 2–5 $\mu$l of dimethyl sulfoxide and with 20 $\mu$l of a snake venom solution and 40 $\mu$l of the crude enzyme solution. Sufficient Tris-hydrochloric acid buffer was added to make a total volume of 100 $\mu$l. The mixture was allowed to react at 30° C. for 20 minutes. At the end of this time, the reaction mixture was treated with an Amberlite (trade mark) IRP-58 resin and the level of residual adenosine radioactivity in the product was determined. The experiment was carried out at a number of concentration levels of each active compound and from this was calculated the 50% inhibition values ($I_{50}$).

The experiment was repeated, except that cyclic guanosine monophosphate (cGMP) was employed as the substrate instead of cAMP. The $I_{50}$ value against cGMP PDE was also calculated.

The results are shown in Table 1, where the $I_{50}$ values are given in $\mu$moles.

TABLE 1

| Compound No. | $I_{50}$($\mu$moles) | |
|---|---|---|
| | cAMP PDE | cGMP PDE |
| 36 | 6.8 | 48 |
| 37 | 0.31 | 2.9 |
| 39 | 33 | 111 |
| 40 | 3.2 | 90 |
| 41 | 9.3 | 243 |
| 45 | 0.6 | 1.2 |
| 46 | 1.8 | 0.9 |
| 51 | 0.32 | 0.13 |
| 53 | 14 | 1.2 |
| 54 | 19 | 9.1 |
| 58 | 2.0 | 14 |
| 59 | 31 | 39 |

TABLE 1-continued

| Compound No. | I₅₀(μmoles) cAMP PDE | cGMP PDE |
|---|---|---|
| 60 | 5.4 | 4.8 |
| 63 | 7.4 | 9.7 |
| 81 | 4.4 | 13 |
| 88 | 1.5 | 14.8 |
| 124 | 10 | 4.9 |
| 133 | 0.14 | 1.1 |
| 135 | 2.0 | 4.2 |
| 137 | 3.4 | 19.0 |
| 138 | 0.14 | 0.05 |
| 140 | 0.76 | 2.8 |
| 141 | 0.22 | 1.05 |
| 142 | 0.15 | 2.5 |
| 143 | 0.09 | 4.1 |
| 144 | 0.19 | 1.1 |
| 187 | 35.0 | 32 |
| 192 | 30.4 | 49.8 |
| 195 | 3.9 | 3.2 |
| 196 | 2.5 | 1.7 |
| 197 | 25.0 | 13.1 |
| 247 | 0.45 | 6.4 |
| 248 | 3.2 | 12.7 |
| 249 | 0.44 | 2.8 |
| theophylline | 360.0 | 196.0 |

The known compound used for comparison is theophylline, which is known to inhibit both cAMP PDE and cGMP PDE and is employed therapeutically for this purpose. The least effective of those compounds of the invention tested has an $I_{50}$ value which is about an order of magnitude smaller than the corresponding value for theophylline, whilst the most effective of those compounds of the invention tested has an $I_{50}$ value some 3–4 orders of magnitude lower, indicating that the activities of the compounds of the invention as PDE inhibitors are extraordinarily strong.

Promotion of recovery from anoxia-induced cerebral dysfunction

In this experiment, the breathing of a rat was terminated for sufficient time for its EEG (electroencephalograph) trace to become flat and the time required for the EEG to show further activity after breathing had restarted was determined.

Under anaesthesia, a canula was inserted into the trachea of a rat which already had an electrode implanted in its skull. The rat was immobilized by the administration of pancuronium bromide, and its spontaneous EEG was recorded. After the rat had been roused from anaesthesia, the compound under test suspended in an aqueous solution of carboxymethylcellulose was administered intraperitoneally to the rat. Throughout the experiment, the rat was caused to breathe artificially; 30 minutes after administration of the test compound, artificial breathing was terminated for 120 seconds. After breathing again commenced, the time required for the EEG to recover (the recovery time) was determined.

A control experiment was carried out in which a carboxymethylcellulose suspension alone was administered with no active compound.

The results are summarized in Table 2, from which it can be seen that the compound of the invention substantially improves the time taken for recovery.

The recovery time is reported in the Table in seconds as the mean of the recovery times of all of the animals in the relevant test group plus or minus the statistical error.

TABLE 2

| Active compound | Dose (mg/kg) | No. of animals | Recovery time (secs) |
|---|---|---|---|
| Control (None) | — | 8 | 20.8 ± 2.5 |
| Compound No. 131 | 10 | 8 | 14.5 ± 1.2 |
| | 30 | 8 | 13.8 ± 1.3 (P < 0.05) |

Effect on sugar and high energy phosphate metabolism in the brain of rats with cerebral ischaemia Cerebral ischaemia was induced in rats and the sugar and high energy phosphate metabolism in the brain was investigated.

Both carotid arteries of the test rats were ligated and, at the same time, the compound under test was administered by intraperitoneal injection. The amounts of sugars and metabolic products thereof (glucose and lactic acid) and high energy phosphate (ATP-adenosine triphosphate) in the brain were determined by the method of Lowry and Passonneau (A flexible system of enzymatic analysis, Academic Press, New York, 1972). When Compound No. 131 was administered at levels of 1 mg/kg or 10 mg/kg, there was observed an increase in glucose levels, a decrease in lactic acid levels and an increase in ATP levels in the rats with cerebral ischaemia. This suggests that the sugar and high energy phosphate metabolism of the rats had been restored either partly or completely.

Effect on recovery of erythrocyte flexibility reduced by acidosis

Mature male rats were employed in this experiment in groups of five for each test. The compound under test was suspended in an aqueous solution of carboxymethylcellulose and administered orally. Two hours after administration, the rats were anaesthetized with pentobarbital and a 5 ml blood sample was taken from the heart. Its pH was adjusted to 5.1 and the sample was allowed to stand. The fluidity of the erythrocytes was tested by a slightly modified version of the method reported in the Journal of Clinical Pathology, 29, 855-858 (1976). Control animals were treated similarly, except that the carboxymethylcellulose solution contained no active compound. The results are shown in Table 3. The results are reported as the mean values for each group plus or minus the statistical error and the statistical significance was calculated by comparison with the control group.

TABLE 3

| Active Compound | Dose (mg/kg) | Blood pH | Total number of passing erythrocytes × 10⁹ |
|---|---|---|---|
| None: | | | |
| (a) Normal blood | — | 7.2 | 4.00 ± 0.06 |
| (b) Control | — | 5.1 | 2.40 ± 0.13 |
| Compound No. 71 | 50 mg/kg | 5.1 | 3.00 ± 0.16 (P < 0.05) |
| Compound No. 131 | 50 mg/kg | 5.1 | 3.30 ± 0.28 (P < 0.05) |

As can clearly be seen from this Table, the compounds of the invention significantly improve the fluidity of erythrocytes in the acidified blood.

Improving cerebral blood flow

The test animals were mature rabbits and cerebral blood flow was tested by means of a thermoelectric couple according to the method of Hagiwara et al. [Folia Pharmacol. Japon., 71, 709–725 (1975)]. The results are shown in Table 4. The "increase in cerebral blood flow (Vp)" is expressed as a ratio with the blood flow achieved by the administration of papaverine administered at a dose of 1 mg/kg. The "duration (T½)" is the time in minutes required for the increase in cerebral blood flow to reduce by one half.

TABLE 4

| Active Compound | Dose (mg/kg) | Increase in cerebral blood flow (Vp) | Duration (T ½) (mins) | Change in blood pressure mm Hg (pascals) |
|---|---|---|---|---|
| Papaverine | 1 | 1.0 | 2.4 | −7.8 (−1040) |
| Vincamine | 1 | 1.7 | 3.2 | −2 (−270) |
|  | 2.5 | 3.2 | 2.1 | −22 (−2930) |
| Nicardipine | 0.01 | 3.2 | 14 | −12 (−1600) |
| Compound |  |  |  |  |
| No. 71 | 10 | 3.0 | >60 | no change |
| No. 133 | 10 | 10 | >60 | no change |
| No. 138 | 10 | 5.5 | >60 | no change |
| No. 141 | 10 | 9.2 | >60 | no change |

The results clearly show that the compounds of the invention increased cerebral blood flow. This increase was of long duration and it is significant that the drug has no effect on blood pressure, unlike the control drugs known to be used for this purpose.

Improvement in blood viscosity

The test animals were male Wistar rats; they were employed in groups of five for each test. The rats were anaesthetized with pentobarbital and simultaneously the test compound was administered orally at the dose specified in Table 5 in a carboxymethyl cellulose suspension. Promptly, an incision was made in the neck and a 0.5 ml blood sample was collected from the jugular vein. The viscosity of this sample was determined by means of a rotational viscometer.

Thirty minutes after oral administration, the common carotid artery was ligated bilaterally. One hour thereafter (i.e. 90 minutes after oral administration), a further 0.5 ml blood sample was collected from the jugular vein and its viscosity was determined in the same manner.

The mean blood viscosity of each test animal and its standard deviation were calculated for each of the four shear rates (37.5, 75, 150 and 375 s$^{-1}$) of the rotational viscometer. The pre-ligation and post-ligation values of each group (i.e. the change over a period of 60 minutes) were analysed by the statistical t-test. The results are reported in Table 5 as follows: for each shear rate where no significant rise in blood pressure was noted (P<0.05) between the pre-ligation and post-ligation values there is printed a single plus sign (+). Thus, for example, if there was no significant difference in viscosity between the pre-ligation and post-ligation values at any of the four shear rates, the results will be ++++. In parallel with these experiments, an identical experiment was carried out, except that the test animals were given a carboxymethylcellulose solution alone with no active compound; the results for this test group showed a significant increase in blood viscosity at each of the four shear rates.

As can be seen from Table 5, a significant improvement (i.e. stabilisation) in blood viscosity was achieved with Compound No. 202 at all dose levels, with Compound No. 131 at a dose not less than 30 mg/kg, and with Compounds No. 10 and 54 at doses not less than 50 mg/kg.

TABLE 5

| Compound No | Dose (mg/kg) | | | |
|---|---|---|---|---|
|  | 10 | 30 | 50 | 100 |
| 10 | — | ++++ | ++++ | N.T.* |
| 54 | N.T. | ++ | +++ | N.T. |
| 131 | N.T. | + | +++ | ++++ |
| 202 | + | +++ | +++ | +++ |

*N.T. = Not tested

Brain concussive test

The test compound, suspended in an aqueous solution of carboxymethylcellulose, was administered intraperitoneally to mice. After 30 minutes, a 16 g weight was dropped from a height of 50 cm onto the head of each mouse, and the time was measured for each mouse to recover its righting reflex and spontaneous locomotive activity.

A similar experiment was carried out as a control, using the carboxymethylcellulose solution without any active compound.

The results are reported in Table 6 as the mean time (in seconds) plus or minus the statistical error. There were 20 mice in the control group and 17 mice in the group to which the test compound was administered.

TABLE 6

| Compound No. | Dose (mg/kg) | Recovery time (secs.) | |
|---|---|---|---|
|  |  | Righting reflex | Spontaneous locomotive activity |
| None (control) | — | 71.4 ± 29.3 | 185.9 ± 51.1 |
| 202 | 10 | 20.9 ± 2.9 | 72.8 ± 15.7 (P < 0.05) |

The compounds of the invention may accordingly be used as therapeutic agents for various cerebral circulatory disorders, such as cerebral apoplexy sequelae and cerebral infarction sequelae, and as brain metabolism activators, for example for the therapy of senile dementia or traumatic brain infarction. The compounds of the invention may be administered orally or non-orally (for example by subcutaneous or intramuscular injection).

The compounds of the invention may be administered orally in the form of solid preparations which may, if necessary, contain various conventional additives. Such additives include: diluents, such as sugars and cellulose preparations; binders, such as starch, gums and methylcellulose; and disintegrating agents. The dosage will vary depending upon the symptoms, age and body weight of the patient. For example, in the case of an adult human patient, a suitable daily dose would be from 0.1 to 100 mg of the active compound, which may be administered in a single dose or in divided doses.

The preparation of various compounds of the present invention is illustrated in the following Examples.

EXAMPLE 1

Dibenzhydryl griseolate (Compound No. 20)

10 g of griseolic acid were suspended in a mixture of 400 ml of acetone and 50 ml of water. To this was added a solution of 15.4 g of diphenyldiazomethane in 100 ml of acetone, and the mixture was stirred for 16 hours at room temperature. The reaction product was then added dropwise to 2 liters of hexane. The resulting powdery substance was collected by filtration, and then washed with 500 ml of hexane and dried at 55°–65° C. for 10 hours under a pressure of 1–2 mmHg (100–250 Pa) to yield 17.95 g (yield 95.6%) of the title compound as a white powder.

Ultraviolet Absorption Spectrum (methanol) $\lambda_{max}$ nm ($\epsilon$):
258 (11200).

Nuclear Magnetic Resonance Spectrum (hexadeuterated dimethyl sulfoxide) $\delta$ ppm:
4.68 (1H, doublet, J=6.0 Hz);
4.93 (1H, singlet);
5.27 (1H, doublet, J=3.0 Hz);
6.35 (1H, doublet of doublets, J=3.0 & 6.0 Hz);
6.58 (1H, singlet);
8.18 (1H, singlet);
8.37 (1H, singlet).

EXAMPLE 2

Dimethyl griseolate (Compound No. 21)

(a) Using diazomethane 700 mg of griseolic acid were dissolved in 100 ml of ice-cooled dimethylformaldehyde. A solution of 1.0–1.2 mmole of diazomethane in 1 ml of diethyl ether was then added to the resulting solution, with stirring, until the mixture acquired a yellowish color. The mixture was then left to react for 10 minutes. After completion of the reaction, acetic acid was added to the reaction product until the reaction product lost its color. The mixture was then evaporated to dryness under reduced pressure. The dried product was dissolved in methanol and the resulting solution was filtered. The filtrate was evaporated to dryness under reduced pressure. The dried product was recrystallized from water to yield 540 mg of the title compound.

(b) Via mixed acid anhydrides 1.14 g of griseolic acid was suspended in 20 ml of methanol. 1.39 ml of benzoyl chloride was added, with ice cooling, to the solution, which was left standing at room temperature for 16 hours. The solvent was then evaporated off under reduced pressure, and the resulting residue was treated with diethyl ether, to give a white solid material which was collected by filtration and dissolved in a small quantity of water; the pH of this mixture was adjusted to a value of 7. The resulting mixture was kept in a refrigerator overnight. The precipitated crystals were collected by filtration to yield 1.08 g of the desired compound.

Ultraviolet Absorption Spectrum (methanol) $\lambda_{max}$ nm ($\epsilon$):
258 (15600).

Nuclear Magnetic Resonance Spectrum (hexadeuterated dimethyl sulfoxide) $\delta$ ppm:
4.60 (1H, doublet, J=6.0 Hz);
4.66 (1H, singlet);
5.12 (1H, doublet, J=3.0 Hz);
6.06 (1H, doublet of doublets, J=3.0 & 6.0 Hz);
6.53 (1H, singlet);
8.33 (1H, singlet);
8.37 (1H, singlet).

EXAMPLE 3

Dibenzhydryl $N^6,O^{2'},O^{7'}$-triacetylgriseolate (Compound No. 13)

1.06 g of dibenzhydryl griseolate (prepared as described in the Example 1) was dissolved in 10 ml of anhydrous pyridine. To this was added, with ice-cooling, 1.13 ml of acetic anhydride. The mixture was then stirred for 30 minutes whilst ice-cooling and then left standing at 50° C. for 16 hours. After this, 20 ml of methanol were added, with ice-cooling, to the mixture, which was then stirred for 30 minutes. At the end of this time, the solvent was distilled off under reduced pressure. Ethanol and water were added to the residue and then distilled off. This process was repeated 4 times until the smell of pyridine could no longer be perceived. Subsequently, the resulting product was dissolved in 15 ml of benzene, and the resulting solution was lyophilized to yield 1.21 g of the title compound as a crude product. This yellowish powder can be used as such for subsequent reactions, but a sample for analysis was obtained by silica gel column chromatography using as eluent methylene chloride containing 1% v/v methanol.

Ultraviolet Absorption Spectrum (methanol) $\lambda_{max}$ nm ($\epsilon$):
262 (15400), 280 shoulder (7900).

Nuclear Magnetic Resonance Spectrum (hexadeuterated dimethyl sulfoxide) $\delta$ ppm:
5.35 (1H, doublet, J=3.0 Hz);
5.75 (1H, doublet, J=6.0 Hz);
5.99 (1H, singlet);
6.49 (1H, doublet of doublets, J=3.0 & 6.0 Hz);
7.00 (1H, singlet);
8.59 (1H, singlet);
8.65 (1H, singlet).

EXAMPLE 4

Dibenzhydryl $N^6,O^{2'},O^{7'}$-tripropionylgriseolate (Compound No. 10)

The procedure described in Example 3 was repeated, except that anhydrous propionic acid was used instead of acetic anhydride and the reaction was carried out at room temperature, to yield the desired compound.

Ultraviolet Absorption Spectrum (50% v/v aqueous methanol) $\lambda_{max}$ nm ($\epsilon$):
270 (17700).

Nuclear Magnetic Resonance Spectrum (hexadeuterated dimethyl sulfoxide) $\delta$ ppm:
5.34 (1H, doublet, J=3.0 Hz);
5.80 (1H, doublet, J=6.6 Hz);
6.01 (1H, singlet);
6.52 (1H, doublet of doublets, J=3.0 & 6.6 Hz)
7.00 (1H, singlet);
8.60 (1H, singlet);
8.69 (1H, singlet).

EXAMPLE 5

Dibenzhydryl $N^6,O^{2'},O^{7'}$-tributyrylgriseolate (Compound No. 11)

The procedure described in Example 3 was repeated, except that anhydrous butyric acid was used instead of acetic anhydride and the reaction was carried out at room temperature, to yield the desired compound.

Ultraviolet Absorption Spectrum (50% v/v aqueous methanol) $\lambda_{max}$ nm ($\epsilon$):
271.5 (17400).

Nuclear Magnetic Resonance Spectrum (hexadeuterated dimethyl sulfoxide) $\delta$ ppm:
5.33 (1H, doublet, J=3.0 Hz);
5.83 (1H, doublet, J=6.6 Hz);
6.02 (1H, singlet);
6.58 (1H, doublet of doublets, J=3.0 & 6.6 Hz);
7.00 (1H, singlet);
8.61 (1H, singlet);
8.71 (1H, singlet).

EXAMPLE 6

Dibenzhydryl $N^6,N^6,O^{2'},O^{7'}$-tetrabenzoylgriseolate (Compound No. 1)

17.8 g of dibenzhydryl griseolate (prepared as described in Example 1) were dissolved in anhydrous pyridine. To this solution were added 18.5 ml of benzoyl chloride, with ice cooling, and the mixture was kept standing at room temperature for 16 hours, protecting it from moisture. The reaction product was then ice-cooled, and 10 ml of water were added. The mixture was stirred at room temperature for 1 hour. The solvent was then distilled off under reduced pressure. The residue was dissolved in a mixture of 100 ml of ethyl acetate and 50 ml of water, and then the ethyl acetate layer was separated. This separated layer was washed with dilute hydrochloric acid, water, an aqueous solution of sodium bicarbonate and a saturated aqueous solution of sodium chloride, in that order. The organic solution was separated and dried over anhydrous magnesium sulfate. The solvent was distilled off under reduced pressure to yield a pale yellowish residue. This residue was dissolved in a small quantity of methylene chloride, to which ethanol was then added. The solvent was then slowly distilled off under reduced pressure with an aspirator, leaving a yellowish powdery substance. This substance was collected by filtration, washed with ethanol was then dried to yield 9.1 g of the title compound in the form of yellowish powder and in a yield of 92.5%. A sample for analysis was obtained by lyophilizing with benzene the product purified by silica gel column chromatography, eluted with a 10% v/v solution of acetone in benzene.

Ultraviolet Absorption Spectrum (methanol) $\lambda_{max}$ nm ($\epsilon$):
273 (22000).

Nuclear Magnetic Resonance Spectrum (hexadeuterated dimethyl sulfoxide) $\delta$ ppm:
5.63 (1H, doublet, J=3.3 Hz);
6.04 (1H, doublet, J=6.6 Hz);
6.13 (1H, singlet);
6.63 (1H, doublet of doublets, J=3.0 & 6.6 Hz);
8.63 (1H, singlet);
8.89 (1H, singlet).

The compounds listed in Examples 7 through 13 were obtained in the same manner as described in Example 6, except that the corresponding compound from Example 1 or 2 was selected as the starting material and that the corresponding acid chloride or acid anhydride was selected instead of benzoyl chloride.

EXAMPLE 7

Dibenzhydryl $N^6,N^6,O^{2'},O^{7'}$-tetra-p-toluoylgriseolate (Compound No. 2)

Ultraviolet Absorption Spectrum (methanol) $\lambda_{max}$ nm ($\epsilon$):
247 (49700), 275 shoulder (32900).

Nuclear Magnetic Resonance Spectrum (hexadeuterated dimethyl sulfoxide) $\delta$ ppm:
5.63 (1H, doublet, J=3.0 Hz);
6.00 (1H, doublet, J=6.0 Hz);
6.13 (1H, singlet);
6.62 (1H, doublet of doublets, J=3.0 & 6.0 Hz);
8.63 (1H, singlet);
8.88 (1H, singlet).

EXAMPLE 8

Dibenzhydryl $N^6,N^6,O^{2'},O^{7'}$-tetra-p-chlorobenzoylgriseolate (Compound No. 3)

Ultraviolet Absorption Spectrum (methanol) $\lambda_{max}$ nm ($\epsilon$):
248 (56400), 275 shoulder (31700).

Nuclear Magnetic Resonance Spectrum (hexadeuterated dimethyl sulfoxide) $\delta$ ppm:
5.70 (1H, doublet, J=3.0 Hz);
6.00 (1H, doublet, J=6.0 Hz);
6.11 (1H, singlet);
6.62 (1H, doublet of doublets, J=3.0 & 6.0 Hz);
7.05 (1H, singlet);
8.68 (1H, singlet);
8.89 (1H, singlet).

EXAMPLE 9

Dibenzhydryl $N^6,N^6,O^{2'},O^{7'}$-tetra-p-nitrobenzoylgriseolate (Compound No. 4)

Ultraviolet Absorption Spectrum (methanol) $\lambda_{max}$ nm ($\epsilon$):
261 (57400).

Nuclear Magnetic Resonance Spectrum (hexadeuterated dimethyl sulfoxide) $\delta$ ppm:
5.78 (1H, doublet, J=3.0 Hz);
6.07 (1H, doublet, J=6.0 Hz);
6.16 (1H, singlet);
6.62 (1H, doublet of doublets, J=3.0 & 6.0 Hz);
8.75 (1H, singlet);
8.97 (1H, singlet).

EXAMPLE 10

Dibenzhydryl $N^6,N^6,O^{2'},O^{7'}$-tetra-p-anisoylgriseolate (Compound No. 5)

Ultraviolet Absorption Spectrum (methanol) $\lambda_{max}$ nm ($\epsilon$):
264 (53100), 273 (52400), 275 shoulder (35000).

Nuclear Magnetic Resonance Spectrum (hexadeuterated dimethyl sulfoxide) $\delta$ ppm:
5.64 (1H, doublet, J=3.0 Hz);
5.98 (1H, doublet, J=6.0 Hz);
6.11 (1H, singlet);
6.62 (1H, broad multiplet);
8.65 (1H, singlet);
8.85 (1H, singlet).

EXAMPLE 11

Dimethyl O$^{2'}$,O$^{7'}$-diacetylgriseolate (Compound No. 22)

Ultraviolet Absorption Spectrum (methanol) λ$_{max}$ nm (ε):
257 (17100).
Nuclear Magnetic Resonance Spectrum (hexadeuterated dimethyl sulfoxide) δ ppm:
5.17 (1H, doublet, J=3.0 Hz);
5.66 (1H, doublet, J=6.0 Hz);
5.73 (1H, singlet);
6.31 (1H, doublet of doublets, J=3.0 & 6.0 Hz);
6.89 (1H, singlet);
8.23 (1H, singlet);
8.36 (1H, singlet).

EXAMPLE 12

Dimethyl N$^6$,O$^{2'}$,O$^{7'}$-tribenzoylgriseolate (Compound No. 23)

Ultraviolet Absorption Spectrum (50% v/v aqueous methanol) λ$_{max}$ nm (ε):
230 (48100), 279 (26800).
Nuclear Magnetic Resonance Spectrum (hexadeuterated dimethyl sulfoxide) δ ppm:
5.50 (1H, doublet, J=3.0 Hz);
5.82 (1H, singlet);
5.93 (1H, doublet, J=6.6 Hz);
6.51 (1H, doublet of doublets, J=3.0 & 6.6 Hz);
7.10–8.30 (16H, multiplet);
8.76 (1H, singlet);
8.88 (1H, singlet).

EXAMPLE 13

Dimethyl N$^6$,O$^{2'}$,O$^{7'}$-tri-p-chlorobenzoylgriseolate (Compound No. 24)

Ulraviolet Absorption Spectrum (50% v/v aqueous methanol) λ$_{max}$ nm (ε):
246 (48100), 279 (29200).
Nuclear Magnetic Resonance Spectrum (hexadeuterated dimethyl sulfoxide) δ ppm:
5.52 (1H, doublet, J=3.0 Hz);
5.76 (1H, singlet);
5.89 (1H, doublet, J=6.6 Hz);
6.47 (1H, doublet of doublets, J=3.0 & 6.6 Hz);
7.14–8.20 (9H, multiplet);
8.74 (1H, singlet);
8.88 (1H, singlet).

EXAMPLE 14

O$^{2'}$-Benzoylgriseolic acid (Compound No. 36)

6.81 g of griseolic acid were dissolved in 120 ml of a 0.5M aqueous solution of trisodium phosphate. 120 ml of ethyl acetate were then added. The mixture was stirred and ice-cooled whilst 18 ml of benzoyl chloride were added, and the mixture was then stirred for a further 3 hours. The reaction product was transferred into a separating funnel, and the aqueous layer was separated, while the organic layer was washed with 20 ml of water. The aqueous layer and the washings were combined and washed with 50 ml of ethyl acetate. A further 100 ml of ethyl acetate were added to the aqueous layer, whose pH was then adjusted to a value of 2.0 by adding concentrated hydrochloric acid, whilst ice-cooling. A solid substance formed, but the mixture was left standing overnight in a refrigerator. The solid substance was then collected by filtration and washed with a small quantity of water and then dried, to yield 7.60 g of the title compound.

Ultraviolet Absorption Spectrum (methanol) λ$_{max}$ nm (ε):
230 (17600), 257 (16000).
Nuclear Magnetic Resonance Spectrum (hexadeuterated dimethyl sulfoxide) δ ppm:
4.55 (1H, singlet);
5.28 (1H, doublet, J=3.0 Hz);
5.90 (1H, doublet, J=6.0 Hz);
6.41 (1H, doublet of doublets, J=3.0 & 6.0 Hz);
7.27 (1H, singlet);
8.33 (1H, singlet);
8.43 (1H, singlet).

EXAMPLE 15

Dibenzhydryl O$^{2'}$-benzoylgriseolate (Compound No. 19)

The procedure described in Example 1 was repeated, except that O$^{2'}$-benzoylgriseolic acid (prepared as described in Example 14) was used instead of griseolic acid as the starting material, to give the title compound.

Ultraviolet Absorption Spectrum (methanol) λ$_{max}$ nm (ε):
257 (19000).
Nuclear Magnetic Resonance Spectrum (hexadeuterated dimethyl sulfoxide) δ ppm:
4.98 (1H, singlet);
5.25 (1H, doublet, J=3.0 Hz);
5.93 (1H, doublet, J=6.0 Hz);
6.73 (1H, doublet of doublets, J=3.0 & 6.0 Hz);
7.04 (1H, singlet);
8.18 (1H, singlet);
8.40 (1H, singlet).

The compounds listed in Examples 16 through 18 were obtained in the same manner as described in Example 6 except that the compound described in Example 14 was selected as the starting material instead of the compound of Example 1 and that the corresponding acid chloride or acid anhydride was used instead of benzoyl chloride.

EXAMPLE 16

Dibenzhydryl N$^6$,O$^{7'}$-diacetyl-O$^{2'}$-benzoylgriseolate (Compound No. 14)

Ultraviolet Absorption Spectrum (methanol) λ$_{max}$ nm (ε):
265 (14100).
Nuclear Magnetic Resonance Spectrum (hexadeuterated dimethyl sulfoxide) δ ppm:
5.43 (1H, doublet, J=3.0 Hz);
5.97 (1H, singlet);
6.02 (1H, doublet, J=6.0 Hz);
6.59 (1H, doublet of doublets, J=3.0 & 6.0 Hz);
8.91 (2H, singlet).

EXAMPLE 17

Dibenzhydryl O$^{2'}$-benzoyl-N$^6$,N$^6$,O$^{7'}$-tri-p-toluoylgriseolate (Compound No. 6)

Ultraviolet Absorption Spectrum (methanol) λ$_{max}$ nm (ε):
250 shoulder (41700), 270 shoulder (35300).
Nuclear Magnetic Resonance Spectrum (hexadeuterated dimethyl sulfoxide) δ ppm:
5.61 (1H, doublet, J=3.0 Hz);

6.03 (1H, doublet, J=6.0 Hz);
6.11 (1H, singlet);
6.62 (1H, doublet of doublets, J=3.0 & 6.0 Hz);
8.63 (1H, singlet);
8.87 (1H, singlet).

EXAMPLE 18

Dibenzhydryl $N^6,N^6,O^{7'}$-tri-p-anisoyl-$O^{2'}$-benzoylgriseolate (Compound No. 7)

Ultraviolet Absorption Spectrum (methanol) $\lambda_{max}$ nm ($\epsilon$):
260 shoulder (41400), 273 (45200), 290 (38900).

Nuclear Magnetic Resonance Spectrum (hexadeuterated dimethyl sulfoxide) $\delta$ ppm:
5.60 (1H, doublet, J=3.0 Hz);
6.03 (1H, doublet, J=6.0 Hz);
6.11 (1H, singlet);
6.64 (1H, doublet of doublets, J=3.0 & 6.0 Hz);
8.65 (1H, singlet);
8.86 (1H, singlet).

EXAMPLE 19

Dibenzhydryl $O^{2'},O^{7'}$-dibenzoylgriseolate (Compound No. 15)

7.11 g of dibenzhydryl griseolate (prepared as described in Example 1) were dissolved in 200 ml of acetone. 22.6 g of anhydrous benzoic acid and 27.6 g of anhydrous sodium carbonate were then added, and the mixture was refluxed for 7 hours. Insoluble inorganic substances were filtered off, and the solvent was distilled from the filtrate under reduced pressure, to yield a pale yellow caramel-like residue. This residue was purified by column chromatography, using methylene chloride containing 1% v/v methanol as the eluent and a prepacked silica gel column (Merck). The purified product was lyophilized to yield 4.3 g of the title compound.

Ultraviolet Absorption Spectrum (methanol) $\lambda_{max}$ nm ($\epsilon$):
257 (19500), 280 shoulder (5500).

Nuclear Magnetic Resonance Spectrum (hexadeuterated dimethyl sulfoxide) $\delta$ ppm:
5.57 (1H, doublet, J=3.0 Hz);
5.93 (1H, doublet, J=6.0 Hz);
6.16 (1H, singlet);
6.85 (1H, doublet of doublets, J=3.0 & 6.0 Hz);
8.17 (1H, singlet);
8.43 (1H, singlet).

EXAMPLE 20

Dibenzhydryl $O^{2'},O^{7'}$-diacetylgriseolate (Compound No. 18)

1.37 g of dibenzhydryl griseolate (prepared as described in Example 1) was suspended in 20 ml of pyridine. 0.94 ml of acetic anhydride was added, with ice cooling, and the mixture was stirred whilst protecting it from moisture. Ethanol was added to the reaction product, whilst ice-cooling, and the mixture was stirred for 30 minutes. The residue obtained by distilling the solvent from the reaction product under reduced pressure was dissolved in 30 ml of chloroform, and the solution was washed with water. The organic layer was separated, and the solvent was distilled off under reduced pressure. The resulting residue was then purified by preparative thin layer chromatography using benzene containing 10% v/v methanol as the developing solvent and then lyophilized from benzene to yield 936 mg of the title compound in the form of a white solid.

Ultraviolet Absorption Spectrum (methanol) $\lambda_{max}$ nm ($\epsilon$):
257 (15400).

Nuclear Magnetic Resonance Spectrum (hexadeuterated dimethyl sulfoxide) $\delta$ppm:
5.28 (1H, doublet, J=3.0 Hz);
5.70 (1H, doublet, J=6.0 Hz);
5.98 (1H, singlet);
6.60 (1H, doublet of doublets, J=3.0 & 6.0 Hz);
6.92 (1H, singlet);
8.13 (1H, singlet);
8.35 (1H, singlet).

EXAMPLE 21

Disodium $N^6,O^{2'},O^{7'}$-tribenzoylgriseolate (Compound No. 26)

26.2 g of dibenzhydryl $N^6,N^6,O^{2'},O^{7'}$-tetrabenzoylgriseolate (prepared as described in Example 6) were dissolved in 52 ml of anisole. 52 ml of trifluoroacetic acid were then added, with ice-cooling, and the mixture was stirred for 4 hours at room temperature. The solvent was distilled off under reduced pressure, and the residue was dissolved in acetone. Toluene was added to the acetone solution and distilled off; this process was repeated 3 times. The residue was dissolved in 150 ml of acetone and the solution was slowly poured, with stirring, into 2.5 liters of hexane. The resulting precipitate was collected by filtration, washed with hexane and dried, to yield 17 g of a white powder, which was dissolved in a mixture of 350 ml of ethyl acetate and 60 ml of water, and treated with activated carbon. 8 equivalents of sodium bicarbonate dissolved in 90 ml of water were added, with stirring, to this solution, and the mixture was stirred for 2 hours. The resulting solid was collected by filtration, to yield 17.7 g of the title substance in an impure form. This was then recrystallized from a 1:8 by volume mixture of water and acetone, using activated carbon, to yield 15.7 g of the title compound.

Ultraviolet Absorption Spectrum (methanol) $\lambda_{max}$ nm ($\epsilon$):
228 (39800), 277 (24900).

Nuclear Magnetic Resonance Spectrum (hexadeuterated dimethyl sulfoxide) $\delta$ppm:
5.25 (1H, doublet, J=3.0 Hz);
5.74 (1H, broad doublet, J=6.0 Hz);
6.47 (1H, singlet);
6.48 (1H, doublet of doublets, J=3.0 & 6.0 Hz);
6.98 (1H, singlet);
8.85 (2H, singlet).

The compounds listed in Examples 22 through 29 were obtained in the same manner as described in Example 21, except that the compounds listed respectively in Examples 7, 8, 9, 10, 17, 18, 16 and 5 were employed instead of the compound listed in Example 6 as the starting material.

EXAMPLE 22

Disodium $N^6,O^{2'},O^{7'}$-tri-p-toluoylgriseolate (Compound No. 27)

Ultraviolet Absorption Spectrum (methanol) $\lambda_{max}$ nm ($\epsilon$):
241 (39100), 279 (27200).

Nuclear Magnetic Resonance Spectrum (hexadeuterated dimethyl sulfoxide) $\delta$ppm:

5.22 (1H, broad singlet);
5.62 (1H, broad doublet, J=6.6 Hz);
6.04 (1H, singlet);
6.46 (1H, broad multiplet);
6.91 (1H, singlet);
8.76 (2H, singlet).

EXAMPLE 23

Disodium $N^6,O^{2'},O^{7'}$-tri-p-chlorobenzoylgriseolate (Compound No. 28)

Ultraviolet Absorption Spectrum (methanol) $\lambda_{max}$ nm ($\epsilon$):
241 (43000), 278 (21400).
Nuclear Magnetic Resonance Spectrum (hexadeuterated dimethyl sulfoxide) $\delta$ppm:
5.30 (1H, broad singlet);
5.71 (1H, broad doublet);
5.96 (1H, singlet);
6.45 (1H, broad doublet);
8.82 (1H, singlet);
8.87 (1H, singlet).

EXAMPLE 24

Disodium $N^6,O^{2'},O^{7'}$-tri-p-nitrobenzoylgriseolate (Compound No. 29)

Ultraviolet Absorption Spectrum (tetrahydrofuran) $\lambda_{max}$ nm ($\epsilon$):
262 (35000).
Nuclear Magnetic Resonance Spectrum (hexadeuterated dimethyl sulfoxide) $\delta$ppm:
5.32 (1H, broad singlet);
5.77 (1H, broad multiplet);
6.02 (1H, singlet);
6.48 (1H, broad multiplet);
7.19 (1H, singlet);
8.72 (2H, singlet).

EXAMPLE 25

Disodium $N^6,O^{2'},O^{7'}$-tri-p-anisoylgriseolate (Compound No. 30)

Ultraviolet Absorption Spectrum (methanol) $\lambda_{max}$ nm ($\epsilon$):
259 (43800), 273 (39800), 290 shoulder (32700).
Nuclear Magnetic Resonance Spectrum (hexadeuterated dimethyl sulfoxide) $\delta$ppm:
5.23 (1H, broad singlet);
5.70 (1H, broad doublet);
6.06 (1H, singlet);
6.48 (1H, broad multiplet);
8.74 (2H, singlet).

EXAMPLE 26

Disodium $O^{2'}$-benzoyl-$N^6,O^{7'}$-di-p-toluoylgriseolate (Compound No. 31)

Ultraviolet Absorption Spectrum (methanol) $\lambda_{max}$ nm ($\epsilon$):
234 (39900), 280 (30900).
Nuclear Magnetic Resonance Spectrum (hexadeuterated dimethyl sulfoxide) $\delta$ppm:
5.22 (1H, broad singlet);
5.73 (1H, broad doublet);
6.02 (1H, singlet);
6.44 (1H, broad multiplet);
8.82 (2H, singlet).

EXAMPLE 27

Disodium $N^6,O^{7'}$-di-p-anisoyl-$O^{2'}$-benzoylgriseolate (Compound No. 32)

Ultraviolet Absorption Spectrum (methanol) $\lambda_{max}$ nm ($\epsilon$):
259 (34100), 284 (36400).
Nuclear Magnetic Resonance Spectrum (hexadeuterated dimethyl sulfoxide) $\delta$ppm
5.23 (1H, broad singlet);
5.72 (1H, broad doublet);
6.06 (1H, singlet);
6.46 (1H, broad multiplet);
8.79 (2H, singlet).

EXAMPLE 28

$N^6,O^{7'}$-Diacetyl-$O^{2'}$-benzoylgriseolic acid (Compound No. 33)

Ultraviolet Absorption Spectrum (methanol) $\lambda_{max}$ nm ($\epsilon$):
210 (31800), 269 (18900), 228 shoulder (20400).
Nuclear Magnetic Resonance Spectrum (hexadeuterated dimethyl sulfoxide) $\delta$ppm:
5.20 (1H, doublet, J=3.0 Hz);
5.56 (1H, singlet);
5.85 (1H, doublet, J=6.0 Hz);
6.37 (1H, doublet of doublets, J=3.0 & 6.0 Hz);
7.16 (1H, singlet);
8.70 (1H, singlet);
8.78 (1H, singlet).

EXAMPLE 29

$N^6,O^{2'},O^{7'}$-Tributyrylgriseolic acid (Compound No. 34)

Ultraviolet Absorption Spectrum (50% v/v aqueous methanol) $\lambda_{max}$ nm ($\epsilon$):
272 (17400).
Nuclear Magnetic Resonance Spectrum (hexadeuterated dimethyl sulfoxide) $\delta$ppm:
5.20 (1H, doublet, J=3.0 Hz);
5.72 (1H, singlet);
5.77 (1H, doublet, J=6.6 Hz);
6.26 (1H, doublet of doublets, J=3.0 & 6.6 Hz);
6.94 (1H, singlet);
8.71 (1H, singlet);
8.76 (1H, singlet).

EXAMPLE 30

$N^6,O^{2'},O^{7'}$-Tribenzoylgriseolic acid (Compound No. 131)

5.2 g of disodium $N^6,O^{2'},O^{7'}$-tribenzoylgriseolate (prepared as described in Example 21) were suspended in a mixture of 300 ml of ethyl acetate and 180 ml of water, and the suspension was stirred until there was hardly any insoluble material left in it. The pH of the suspension was then adjusted to a value of 1.3 with 3N hydrochloric acid, whilst ice-cooling. The organic layer was separated, washed with a saturated aqueous solution of sodium chloride and dried over anhydrous magnesium sulfate. The solvent was then distilled off until the organic layer was condensed to 270 ml. 270 ml of hexane were added to the condensate, and the resulting white powdery substance was collected by filtration, washed with hexane and dried to yield 4.37 g of the title compound.

Ultraviolet Absorption Spectrum (50% v/v aqueous methanol) $\lambda_{max}$ nm ($\epsilon$):

232 (41400), 278 (27700).

Nuclear Magnetic Resonance Spectrum (hexadeuterated dimethyl sulfoxide) δppm:
5.43 (1H, doublet, J=3.0 Hz);
5.79 (1H, singlet);
5.92 (1H, doublet, J=6.0 Hz);
6.47 (1H, doublet of doublets, J=3.0 & 6.0 Hz);
7.10-8.20 (16H, multiplet);
8.77 (1H, singlet);
8.88 (1H, singlet).

EXAMPLE 31

$O^{2'},O^{7'}$-Dibenzoylgriseolic acid (Compound No. 40)

2.80 g of dibenzhydryl $O^{2'},O^{7'}$-dibenzoylgriseolate (prepared as described in Example 19) were dissolved in 10 ml of anisole. 10 ml of trifluoroacetic acid were then added, whilst ice-cooling, and the mixture was left standing at room temperature for one hour. The residue obtained by distilling off the solvent under reduced pressure was dissolved in acetone, toluene was added, and then the solvent was distilled off; this process was repeated 3 times. The resulting yellowish caramel-like substance was dissolved in 20 ml of acetone, and this solution was slowly poured into 200 ml of hexane, with stirring. The mixture was then stirred for 30 minutes, and the precipitate was collected by filtration. The precipitate was suspended in 20 ml of a 5% w/v aqueous solution of sodium bicarbonate and 20 ml of water. 50 ml of ethyl acetate were added and the pH of the mixture was adjusted to a value of 0.5-1 by the addition of concentrated hydrochloric acid so as to completely dissolve the precipitate. The pH of this solution was then adjusted to a value of 2.0 with sodium bicarbonate, and the resulting white crystalline substance was collected by filtration and washed with 100 ml of water and 100 ml of hexane, and then dried, to yield 2.27 g of the title compound in the form of a white powder.

Ultraviolet Absorption Spectrum (methanol) $\lambda_{max}$ nm ($\epsilon$):
230 (28000), 256 (17700).

Nuclear Magnetic Resonance Spectrum (hexadeuterated dimethyl sulfoxide) δppm
5.40 (1H, doublet, J=3.0 Hz);
5.80 (1H, singlet);
5.87 (1H, doublet, J=6.0 Hz);
6.51 (1H, doublet of doublets, J=3.0 & 6.0 Hz);
7.15 (1H, singlet);
8.32 (1H, singlet);
8.48 (1H, singlet).

EXAMPLE 32

$O^{2'},O^{7'}$-Diacetylgriseolic acid (Compound No. 41)

1.0 g of dibenzhydryl $O^{2'},O^{7'}$-diacetylgriseolate (prepared as described in Example 20) was dissolved in 10 ml of anisole. 10 ml of trifluoroacetic acid were then added, whilst ice-cooling, and the mixture was left standing for 30 minutes at room temperature. The solvent was distilled from the product under reduced pressure. The resulting residue was dissolved in acetone. Toluene was added to the solution for extraction, and then distilled off under reduced pressure; this process was repeated 3 times to yield a pale yellowish residue. The residue was dissolved in 10 ml of acetone and the solution was poured slowly into 250 ml of hexane, with stirring. The resulting white precipitate was collected by filtration, washed with hexane and dried. The precipitate was dissolved in 10 ml of a saturated aqueous solution of sodium bicarbonate, whilst ice-cooling. The mixture was acidified with 6N hydrochloric acid, and a white precipitate was formed. On further addition of hydrochloric acid to a pH value of 0.5-1.0, the precipitate dissolved again to yield a clear solution. This clear solution was subjected to reverse phase column chromatography using a prepacked column Rp-8 (Merck) which was washed with water and then eluted with a 10% v/v aqueous solution of acetonitrile. The main peaks of the eluate were collected and lyophilized to yield 412 mg of the title compound as a pale yellowish powder.

Ultraviolet Absorption Spectrum (methanol) $\lambda_{max}$ nm ($\epsilon$):
257 (15400).

Nuclear Magnetic Resonance Spectrum (hexadeuterated dimethyl sulfoxide) δppm:
5.13 (1H, doublet, J=3.0 Hz);
5.64 (2H);
6.24 (1H, doublet of doublets, J=3.0 & 6.0 Hz);
6.85 (1H, singlet);
8.23 (1H, singlet);
8.37 (1H, singlet).

EXAMPLE 33

$O^{7'}$-Benzoylgriseolic acid (Compound No. 37)

1.174 g of $O^{2'},O^{7'}$-dibenzoylgriseolic acid (prepared as described in Example 31) was dissolved in a 20% w/v solution of ammonia in methanol, and the solution was left standing for 2 hours, whilst ice-cooling. The solvent was then distilled off under reduced pressure to yield a white precipitate, which was suspended in a mixture of 30 ml of water and 30 ml of diethyl ether. Concentrated hydrochloric acid was added to this suspension until its pH reached a value within the range of 0-1. Initially, a white insoluble material was formed, but this, however, soon dissolved. The aqueous layer was separated, washed with 30 ml of diethyl ether, and then transferred to a beaker, to which solid sodium bicarbonate was added until the pH of the mixture reached a value of 2.0. The resulting white precipitate was collected by filtration and dried to yield a white powdery substance, which was recrystallized from aqueous acetone to yield 700 mg of the title compound as a white powder.

Ultraviolet Absorption Spectrum (methanol) $\lambda_{max}$ nm ($\epsilon$):
216 (31900), 227 (20000), 257 (17500).

Nuclear Magnetic Resonance Spectrum (hexadeuterated dimethyl sulfoxide) δ ppm:
4.71 (1H, doublet, J=6.0 Hz);
5.17 (1H, doublet, J=3.0 Hz);
5.59 (1H, singlet);
5.82 (1H, singlet);
6.11 (1H, doublet of doublets, J=3.0 & 6.0 Hz);
8.26 (1H, singlet);
8.42 (1H, singlet).

EXAMPLE 34

$N^6$-Benzoylgriseolic acid (Compound No. 35)

1.47 g of disodium $N^6,O^{2'},O^{7'}$-tribenzoylgriseolate (prepared as described in Example 21) was dissolved in a 1N aqueous solution of sodium hydroxide, and the solution was left standing for 15 hours at room temperature. 30 ml of ethyl acetate were then added and the pH of the solution was adjusted to a value of 2.0 with 2N hydrochloric acid, whilst ice-cooling. Insoluble material formed. The mixture was stirred for a further 20 minutes. The precipitate was collected by filtration and recrystallized from aqueous acetone to yield 725 mg of the desired compound as pale yellow crystals.

Ultraviolet Absorption Spectrum (methanol) $\lambda_{max}$ nm ($\epsilon$):
278 (25400).

Nuclear Magnetic Resonance Spectrum (hexadeuterated dimethyl sulfoxide) $\delta$ ppm:
4.56 (1H, singlet);
4.72 (1H, doublet, J=6.0 Hz);
5.18 (1H, doublet, J=3.0 Hz);
6.08 (1H, doublet of doublets, J=3.0 & 6.0 Hz);
6.67 (1H, singlet);
8.74 (1H, singlet);
8.87 (1H, singlet).

EXAMPLE 35

$N^6,O^{7'}$-Dibenzoylgriseolic acid (Compound No. 39) 1.7 g of disodium $N^6$, $O^{2'}$, $O^{7'}$-tribenzoylgriseolate (prepared as described in Example 21) was dissolved, with ice-cooling, in 17 ml of a 0.5N aqueous solution of sodium hydroxide, and the mixture was stirred for 1 hour. The pH of the mixture was then adjusted to a value of 2 with 3N hydrochloric acid, and the mixture was purified by reverse phase chromatography through a prepacked column Rp-8 (Merck) to yield 460 mg of the title compound.

Ultraviolet Absorption Spectrum (50% v/v aqueous methanol) $\lambda_{max}$ nm ($\epsilon$):
279 (23200).

Nuclear Magnetic Resonance Spectrum (hexadeuterated dimethyl sulfoxide) $\delta$ ppm:
4.76 (1H, doublet, J=6.0 Hz);
5.20 (1H, doublet, J=3.0 Hz);
5.82 (1H, singlet);
6.08 (1H, doublet of doublets, J=3.0 & 6.0 Hz);
6.69 (1H, singlet);
8.73 (1H, singlet);
8.83 (1H, singlet).

EXAMPLE 36

6-Desamino-6-hydroxygriseolic acid (Compound No. 51)

5.31 g of griseolic acid were dissolved, with heating, in an 80% w/v aqueous solution of acetic acid, which was thereafter cooled down to room temperature. 9.60 g of sodium nitrite were then added. The air in the vessel containing said solution was replaced by nitrogen, and the vessel was tightly stoppered and left standing for 16 hours. The solvent was distilled off under reduced pressure to yield a residue, to which ethanol was added and then distilled off; this process was repeated until the mixture no longer smelled of acetic acid. The residue was dissolved in 50 ml of water, and the pH of the solution was adjusted to a value of 1.0 with concentrated hydrochloric acid, whilst ice-cooling. The solution was left standing for 16 hours in a refrigerator, and then the precipitate was collected by filtration and washed with a small quantity of water. The precipitate was then recrystallized from aqueous acetone to yield 1.66 g of the title compound. On condensing the mother liquor, 2.20 g of crude crystals were obtained. These crude crystals were then recrystallized from aqueous acetone to yield a further 1.2 g of the title compound.

Ultraviolet Absorption Spectrum (H$_2$O) $\lambda_{max}$ nm ($\epsilon$):
247 (11800), 270 shoulder (3700).

Nuclear Magnetic Resonance Spectrum (hexadeuterated dimethyl sulfoxide) $\delta$ ppm:
4.50 (1H, singlet);
4.57 (1H, doublet, J=6.0 Hz);
5.12 (1H, doublet, J=3.0 Hz);
5.88 (1H, doublet of doublets, J=3.0 & 6.0 Hz);
6.50 (1H, singlet);
8.17 (1H, singlet);
8.33 (1H, singlet).

EXAMPLE 37

Dibenzhydryl 6-desamino-6-hydroxygriseolate (Compound No. 68)

(a) The procedure described in Example 1 was repeated, except that 6-desamino-6-hydroxygriseolic acid (prepared as described in Example 36) was used instead of griseolic acid as the starting material, to yield the desired compound.

(b) 28.5 g of dibenzhydryl griseolate (prepared as described in Example 1) were dissolved, with some heating, in 560 ml of acetic acid, and then 140 ml of water were added. The oxygen in the reaction vessel was replaced by nitrogen, whilst ice-cooling, and sodium nitrite was then added bit by bit without stirring. The mixture was left standing overnight, tightly stoppered. Water was then added to the reaction product and the solvent was distilled off. This product was repeated and the precipitate was collected by filtration and thoroughly washed with water to yield 28.5 g of the title compound.

Ultraviolet Absorption Spectrum (methanol) $\lambda_{max}$ nm ($\epsilon$):
241 (12000), 248 shoulder (11300), 270 shoulder (4300).

Nuclear Magnetic Resonance Spectrum (hexadeuterated dimethyl sulfoxide) $\delta$ ppm:
4.60 (1H, doublet, J=6.0 Hz);
4.90 (1H, singlet);
5.31 (1H, doublet, J=3.0 Hz);
6.06 (1H, doublet of doublets, J=3.0 & 6.0 Hz);
6.53 (1H, singlet);
8.06 (1H, singlet);
8.28 (1H, singlet).

The compounds listed in Examples 38 through 42 were obtained in the same manner as described in Example 37(b) except that the compounds listed in Examples 20, 19, 15, 32 and 31, respectively, were used instead of the compound listed in Example 1.

EXAMPLE 38

Dibenzhydryl $O^{2'}$, $O^{7'}$-diacetyl-6-desamino-6-hydroxygriseolate (Compound No. 71)

Ultraviolet Absorption Spectrum (methanol) $\lambda_{max}$ nm ($\epsilon$):
242 (12300), 250(11100), 270 shoulder (4000).

Nuclear Magnetic Resonance Spectrum (hexadeuterated dimethyl sulfoxide) $\delta$ ppm:
5.35 (1H, doublet, J=3.0 Hz);
5.66 (1H, doublet, J=6.0 Hz);
5.97 (1H, singlet);
6.32 (1H, doublet of doublets, J=3.0 & 6.0 Hz);
6.79 (1H, singlet);
8.00 (1H, singlet);
8.29 (1H, singlet).

EXAMPLE 39

Dibenzhydryl
$O^{2'},O^{7'}$-dibenzoyl-6-desamino-6-hydroxygriseolate
(Compound No. 132)

Ultraviolet Absorption Spectrum (50% v/v aqueous methanol) $\lambda_{max}$ nm ($\epsilon$):
221 (59900), 270 shoulder (11400).
Nuclear Magnetic Resonance Spectrum (hexadeuterated dimethyl sulfoxide) δ ppm:
5.65 (1H, doublet, J=3.0 Hz);
5.89 (1H, doublet, J=6.8 Hz);
6.14 (1H, singlet);
6.53 (1H, doublet of doublets, J=3.0 & 6.8 Hz);
7.07 (1H, singlet);
8.02 (1H, singlet);
8.39 (1H, singlet).

EXAMPLE 40

$O^{2'}$-Benzoyl-6-desamino-6-hydroxygriseolic acid
(Compound No. 126)

Ultraviolet Absorption Spectrum (H$_2$O) $\lambda_{max}$ nm ($\epsilon$):
239.5 (20000), 274 shoulder (3500).
Nuclear Magnetic Resonance Spectrum (hexadeuterated dimethyl sulfoxide) δ ppm:
4.40 (1H, singlet);
5.23 (1H, doublet, J=3.0 Hz);
5.51 (1H, doublet, J=6.0 Hz);
6.21 (1H, doublet of doublets, J=3.0 & 6.0 Hz);
7.00 (1H, singlet);
8.22 (1H, singlet);
8.37 (1H, singlet).

EXAMPLE 41

$O^{2'}$, $O^{7'}$-Diacetyl-6-desamino-6-hydroxygriseolic acid
(Compound No. 69)

Ultraviolet Absorption Spectrum (methanol) $\lambda_{max}$ nm ($\epsilon$):
242.5 (12000), 248 shoulder (11000), 270 shoulder (4200).
Nuclear Magnetic Resonance Spectrum (hexadeuterated dimethyl sulfoxide) δ ppm:
5.19 (1H, doublet, J=3.0 Hz);
5.63 (1H, doublet, J=6.0 Hz);
5.68 (1H, singlet);
6.11 (1H, doublet of doublets, J=3.0 & 6.0 Hz);
6.87 (1H, singlet);
8.20 (1H, singlet);
8.36 (1H, singlet).

EXAMPLE 42

$O^{2'}$, $O^{7'}$-Dibenzoyl-6-desamino-6-hydroxygriseolic acid
(Compound No. 70)

Ultraviolet Absorption Spectrum (50% v/v aqueous methanol) $\lambda_{max}$ nm ($\epsilon$):
234.5 (34100) 274 shoulder (5700), 283 shoulder (3400).
Nuclear Magnetic Resonance Spectrum (hexadeuterated dimethyl sulfoxide) δ ppm:
5.40 (1H, doublet, J=3.0 Hz);
5.80 (1H, doublet, J=6.6 Hz);
5.77 (1H, singlet);
6.33 (1H, doublet of doublets, J=3.0 & 6.6 Hz);
7.12 (1H, singlet);
8.20 (1H, singlet);
8.40 (1H, singlet).

EXAMPLE 43

$N^1$-Methylgriseolic acid (Compound No. 42)

758 mg of griseolic acid were suspended in 20 ml of dimethylformamide. 2 ml of methyl iodide were added, with ice-cooling, to the suspension. The mixture, tightly stoppered, was stirred for 2 days at room temperature, and then ethanol was added. The solvent was then distilled off under reduced pressure. This process was repeated 3 times. The resulting residue was dissolved in 10 ml of methanol and 10 ml of concentrated aqueous ammonia, and the mixture was left standing, tightly stoppered, for 4 hours at room temperature. The solvent was distilled off under reduced pressure, and the residue was dissolved in a small quantity of water. The pH of the resulting solution was adjusted to a value of 1 with 1N hydrochloric acid, and the mixture was purified by reverse phase chromatography through a prepacked column Rp-8 (Merck). The main peaks were collected and evaporated to dryness under reduced pressure. The resulting residue was dissolved in the minimum possible quantity of methanol, to which benzene was then added, and the solution was lyophilized to yield 400 mg of the title compound in the form of a pale yellow powder.

Ultraviolet Absorption Spectrum (methanol) $\lambda_{max}$ nm ($\epsilon$):
256.5 (14900).
Nuclear Magnetic Resonance Spectrum (hexadeuterated dimethyl sulfoxide) δ ppm:
4.15 (1H, singlet);
4.50 (1H, doublet, J=6.0 Hz);
4.91 (1H, doublet, J=3.0 Hz);
5.75 (1H, doublet of doublets, J=3.0 & 6.0 Hz);
6.49 (1H, singlet);
8.66 (1H, singlet);
8.71 (1H, singlet).

The compounds listed in Examples 44 and 45 were obtained in the same manner as in Example 43 except that benzyl bromide was used instead of methyl iodide in Example 44 and that 2,4,6-trimethylbenzyl bromide and 6-desamino-6-hydroxygriseolic acid (prepared as described in Example 36) were used as starting materials in Example 45.

EXAMPLE 44

$N^1$-Benzylgriseolic acid (Compound No. 45)

Ultraviolet Absorption Spectrum (50% v/v aqueous methanol) $\lambda_{max}$ nm (δ):
259 (13800).
Nuclear Magnetic Resonance Spectrum (hexadeuterated dimethyl sulfoxide) δ ppm:
4.19 (1H, singlet);
4.50 (1H, doublet, J=6.0 Hz);
4.93 (1H, doublet, J=3.0 Hz);
5.74 (1H, doublet of doublets, J=3.0 & 6.0 Hz);
6.44 (1H, singlet);
8.57 (1H, singlet);
8.77 (1H, singlet).

EXAMPLE 45

6-Desamino-6-hydroxy-$N^1$-(2,4,6-trimethylbenzyl)-griseolic acid (Compound No. 127)

Ultraviolet Absorption Spectrum (methanol) $\lambda_{max}$ nm ($\epsilon$):
246 (9400), 251 (9200), 267 (5500).

Nuclear Magnetic Resonance Spectrum (hexadeuterated dimethyl sulfoxide) δ ppm:
4.52 (1H, doublet, J=6.0 Hz);
4.53 (1H, singlet);
5.12 (1H, doublet, J=3.0 Hz);
5.87 (1H, doublet of doublets, J=3.0 & 6.0 Hz);
6.47 (1H, singlet);
7.73 (1H, singlet);
8.31 (1H, singlet).

EXAMPLE 46

Dibenzhydryl $N^1$-benzylgriseolate (Compound No. 47)

1.42 g of dibenzhydryl griseolate (prepared as described in Example 1) was dissolved in 10 ml of dimethylformamide, and then 4 ml of benzyl bromide were added, whilst ice-cooling. The mixture was allowed to return to room temperature and was then left standing for a full 5 days. The solvent was then distilled off and the residue was dissolved in acetone. The resulting solution was poured slowly into hexane and the precipitate obtained was separated and dissolved in acetone. The solution was evaporated to dryness under reduced pressure, and the residue purified by silica gel column chromatography to yield 850 mg of the title compound.

Ultraviolet Absorption Spectrum (50% v/v aqueous methanol) $\lambda_{max}$ nm (ε):
253 shoulder (13400), 258.5 (14500), 268 shoulder (11100).

Nuclear Magnetic Resonance Spectrum (hexadeuterated dimethyl sulfoxide) δ ppm:
4.60 (1H, doublet, J=6.6 Hz);
4.90 (1H, broad doublet, J=7.0 Hz);
5.20–5.38 (3H, doublet);
6.07 (1H, doublet of doublets);
6.49 (1H, singlet);
8.18 (1H, singlet);
8.21 (1H, singlet).

EXAMPLE 47

Dibenzhydryl $O^{2'},O^{7'}$-diacetyl-6-desamino-6-hydroxy-$N^1$-(2,4,6-trimethylbenzyl)griseolate (Compound No. 129)

The procedure described in Example 46 was repeated, exept that dibenzhydryl $O^{2'},O^{7'}$-diacetyl-6-hydroxygriseolate (prepared as described in Example 38) and 2,4,6-trimethylbenzyl bromide were used as starting materials, to yield the title compound.

Ultraviolet Absorption Spectrum (methanol) $\lambda_{max}$ nm (ε):
244 (16200), 250 (15000), 267 (9600).

Nuclear Magnetic Resonance Spectrum (hexadeuterated dimethyl sulfoxide) δ ppm:
5.28 (1H, doublet, J=2.6 Hz);
5.62 (1H, doublet, J=6.0 Hz);
5.97 (1H, singlet);
6.38 (1H, doublet of doublets, J=2.6 & 6.0 Hz);
6.94 (1H, singlet);
7.58 (1H, singlet);
8.37 (1H, singlet).

EXAMPLE 48

$O^{7'}$-Acetyl-$N^1$-methylgriseolic acid (Compound No. 43)

771 mg of dibenzhydryl $O^{2'},O^{7'}$-diacetylgriseolic acid (prepared as described in Example 20) were dissolved in 10 ml of dimethyl formamide. 1 ml of methyl iodide was added to this solution, and the mixture was left standing for 2 days at room temperature in a tightly stoppered vessel. The solvent was then distilled off under reduced pressure, and the residue was dissolved in toluene. This sequence of distillation and dissolution was repeated 3 times, and the resulting residue was purified by normal phase column chromatography using a Merck prepacked column. The peaks containing the desired compound were lyophilized from benzene to yield 850 mg of a pale yellowish powder.

639 mg of this powder were dissolved in 5 ml of anisole, and then 10 ml of trifluoroacetic acid were added, whilst ice-cooling. The mixture was left standing for 30 minutes at room temperature. The solvent was then distilled off under reduced pressure, and toluene was added to the residue and then distilled off. This process was repeated 3 times. The residue was dissolved in a mixture of chloroform and water. The aqueous layer was separated, washed with chloroform, and then evaporated to dryness under reduced pressure, to yield a clear and colorless caramel-like substance. This substance was dissolved in 20 ml of a 20% w/v solution of ammonia in methanol, and the solution was left standing for 30 minutes at room temperature. The solvent was then distilled off under reduced pressure. The residue was purified by reverse phase chromatography using a Merck prepacked column. The peaks containing the desired compound were collected and lyophilized from water to yield 117 mg of the title compound.

Ultraviolet Absorption Spectrum (methanol) $\lambda_{max}$ nm (ε):
257 (13800).

Nuclear Magnetic Resonance Spectrum (hexadeuterated dimethyl sulfoxide) δ ppm:
4.53 (1H, doublet, J=6.0 Hz);
4.87 (1H, doublet, J=3.0 Hz);
5.17 (1H, singlet);
5.82 (1H, doublet of doublets, J=3.0 & 6.0 Hz);
6.53 (1H, singlet);
8.67 (1H, singlet);
8.73 (1H, singlet).

EXAMPLE 49

$O^{7'}$-Acetyl-$N^1$-benzylgriseolic acid (Compound No. 46)

The procedure described in Example 48 was repeated, except that benzyl bromide was used in lieu of methyl iodide, to yield the title compound.

Ultraviolet Absorption Spectrum (50% v/v aqueous methanol) $\mu_{max}$ nm (ε):
259 (14300).

Nuclear Magnetic Resonance Spectrum (hexadeuterated dimethyl sulfoxide) δ ppm:
4.56 (1H, doublet, J=6.0 Hz);
4.92 (1H, doublet, J=3.0 Hz);
5.22 (1H, singlet);
5.83 (1H, doublet of doublets, J=3.0 & 6.0 Hz);
6.60 (1H, singlet);
8.63 (1H, singlet);
8.83 (1H, singlet).

EXAMPLE 50

Dimethyl $O^{2'},O^{7'}$-diacetyl-6-desamino-6-hydroxygriseolate (Compound No. 129)

1.82 g of dimethyl $O^{2'},O^{7'}$-diacetylgriseolate (prepared as described in Example 11) was dissolved in an 80% w/v aqueous solution of acetic acid. 2.55 g of sodium nitrite were added to the resulting solution, with ice-cooling, and the mixture was left standing for 16 hours in a tightly stoppered vessel. At this stage, some of the starting material was shown to be still present, by thin layer chromatography, and therefore a further 1 g of sodium nitrite was added and the mixture was left standing for 3 hours. The residue obtained by distilling off the solvent under reduced pressure was dissolved in acetone, to which toluene was first added and then distilled off. This process was repeated 3 times.

The residue was dissolved in a mixture of water and chloroform. The organic layer was washed with an aqueous solution of sodium bicarbonate and then with a saturated aqueous solution of sodium chloride and dried over anhydrous magnesium sulfate. The solvent was distilled off to yield a pale brown glass-like substance. This substance was purified by silica gel column chromatography, and then dissolved in a small quantity of acetone, to which benzene was then added, and the mixture was left standing. The resulting white crystals were collected by filtration to yield 1.28 g of the title compound in the form of white crystals.

Ultraviolet Absorption Spectrum (50% v/v aqueous methanol) $\lambda_{max}$ nm ($\epsilon$):
243 (12700), 248 shoulder (12500), 275 shoulder (4300).

Nuclear Magnetic Resonance Spectrum (hexadeuterated dimethyl sulfoxide) $\delta$ ppm:
5.22 (1H, doublet, J=3.0 Hz);
5.62 (1H, doublet, J=6.0 Hz);
5.73 (1H, singlet);
6.13 (1H, doublet of doublets, J=3.0 & 6.0 Hz);
6.88 (1H, singlet);
8.18 (1H, singlet);
8.34 (1H, singlet).

EXAMPLE 51

Dimethyl O$^{2'}$,O$^{7'}$-diacetyl-6-chloro-6-desaminogriseolate (Compound No. 73)

492 mg of dimethyl O$^{2'}$,O$^{7'}$-diacetyl-6-desamino-6-hydroxygriseolate (prepared as described in Example 50) were suspended in 10 ml of ethyl acetate. 10 ml of phosphorus oxychloride were added to the suspension, followed by 0.24 ml of N,N-diethylaniline. The mixture was refluxed, whilst protecting it from moisture. The solvent was distilled off under reduced pressure, and ethyl acetate was added to the residue and then distilled off; this process was repeated 3 times. The residue was dissolved in 20 ml of ethyl acetate, and the solution was washed with a saturated aqueous solution of sodium bicarbonate and then with a saturated aqueous solution of sodium chloride. The organic layer was dried over anhydrous magnesium sulfate and the solvent was distilled off. The resulting residue was purified by silica gel chromatography. The peaks containing the title substance were collected and condensed. The residue was lyophilized from benzene to yield 482 mg of the title compound.

Ultraviolet Absorption Spectrum (methanol) $\lambda_{max}$ nm ($\epsilon$):
247 (7500), 262 (8700).

Nuclear Magnetic Resonance Spectrum (hexadeuterated dimethyl sulfoxide) $\delta$ ppm:
5.28 (1H, doublet, J=3.0 Hz);
5.73 (1H, doublet, J=6.0 Hz);
5.76 (1H, singlet);
6.21 (1H, doublet of doublets, J=3.0 & 6.0 Hz);
7.06 (1H, singlet);
8.92 (2H, singlet).

EXAMPLE 52

Dibenzhydryl O$^{2'}$,O$^{7'}$-diacetyl-6-chloro-6-desaminogriseolate (Compound No. 75)

120 ml of ethyl acetate (dried with a molecular sieve) were added to 12.2 g of dibenzhydryl O$^{2'}$,O$^{7'}$-diacetyl-6-desamino-6-hydroxygriseolate (prepared as described in Example 38), followed by 120 ml of phosphorus oxychloride and 3.66 ml of N,N-diethylaniline, and the mixture was refluxed for 3 hours with heating. The solvent was then distilled off, and the residue was dissolved in a mixture of ethyl acetate and water. The ethyl acetate layer was separated and washed first with dilute hydrochloric acid and then with a saturated aqueous solution of sodium chloride. The solution was then dried over anhydrous magnesium sulfate. The solvent was distilled off and the residue was purified by silica gel column chromatography to yield 10.2 g of the title compound.

Ultraviolet Absorption Spectrum (methanol) $\lambda_{max}$ nm ($\epsilon$):
247 (7700), 258 shoulder (8400), 263 (9000).

Nuclear Magnetic Resonance Spectrum (hexadeuterated dimethyl sulfoxide) $\delta$ ppm:
5.40 (1H, doublet, J=3.0 Hz);
5.76 (1H, doublet, J=6.0 Hz);
6.01 (1H, singlet);
6.41 (1H, doublet of doublets, J=3.0 & 6.0 Hz);
7.07 (1H, singlet);
8.72 (1H, singlet);
8.87 (1H, singlet).

EXAMPLE 53

O$^{2'}$,O$^{7'}$-Diacetyl-6-chloro-6-desaminogriseolic acid (Compound No. 72)

1.8 ml of ethyl acetate, 180 ml of phosphorus oxychloride and 5.4 ml of N,N-diethylaniline were added to 18 g of dibenzhydryl O$^{2'}$,O$^{7'}$-diacetyl-6-desamino-6-hydroxygriseolate (prepared as described in Example 38), and the mixture was refluxed for 20 minutes, with heating. The solvent was then distilled off, and ethyl acetate and water were added to the residue. The ethyl acetate layer was separated, and extracted twice, each time with a 20% w/v aqueous solution of sodium bicarbonate. The pH of the aqueous layer was adjusted to a value of 2, and the resulting precipitate was collected by filtration to yield 6.9 g of the title compound (a yield of 63%). Sodium chloride was added to saturation to the filtrate, which was then extracted twice with ethyl acetate to yield a further 2.4 g of the title compound.

Ultraviolet Absorption Spectrum (50% v/v aqueous methanol) $\lambda_{max}$ nm ($\epsilon$):
246.5 (7400), 262 (8700).

Nuclear Magnetic Resonance Spectrum (hexadeuterated dimethyl sulfoxide) $\delta$ ppm:
5.23 (1H, doublet, J=3.0 Hz);
5.68 (1H, singlet);
5.72 (1H, doublet, J=6.0 Hz);
6.17 (1H, doublet of doublets, J=3.0 & 6.0 Hz);
7.01 (1H, singlet);
8.91 (2H, singlet).

EXAMPLE 54

Dibenzhydryl 6-chloro-6-desaminogriseolate (Compound No. 74)

150 ml of a 20% w/v methanolic solution of ammonia were added to 5 g of dibenzhydryl $O^{2'},O^{7'}$-diacetyl-6-chloro-6-desaminogriseolate (prepared as described in Example 52) and the mixture was stirred for 50 minutes. The solvent was then distilled off at a low temperature and the residue was purified by column chromatography to yield 3.7 g of the title compound.

Ultraviolet Absorption Spectrum (methanol) $\lambda_{max}$ nm ($\epsilon$):
  247 shoulder (9100), 258 shoulder (9300), 263 (9800).

Nuclear Magnetic Resonance Spectrum (hexadeuterated dimethyl sulfoxide) $\delta$ ppm:
  4.72 (1H, broad triplet);
  4.94 (1H, doublet, J=9.9 Hz);
  5.38 (1H, doublet, J=3.0 Hz);
  6.17 (1H, doublet of doublets, J=3.0 & 6.0 Hz);
  6.81 (1H, singlet);
  8.79 (1H, singlet);
  8.91 (1H, singlet).

EXAMPLE 55

6-Chloro-6-desaminogriseolic acid (Compound No. 52)

3.7 g of dibenzhydryl 6-chloro-6-desaminogriseolate (prepared as described in Example 54) were dissolved in 25 ml of anisole, and then 25 ml of trifluoroacetic acid were added, whilst ice-cooling. The mixture was then left standing at room temperature. The solvent was distilled off. A mixture of acetome and toluene was added to the residue, and distilled off; this process was repeated. The residue was dissolved in a small quantity of acetone, and this solution was poured into 300 ml of hexane to yield a powdery substance. This substance was dissolved in a 20% w/v aqueous solution of sodium bicarbonate, and the pH of the resulting solution was adjusted to a value of 2 with 3N hydrochloric acid. The solution was purified by reverse phase chromatography using a Merck Rp-8 prepacked column, to yield 1.46 g of the title compound.

Ultraviolet Absorption Spectrum (H$_2$O) $\lambda_{max}$ nm ($\epsilon$):
  250 shoulder (7200), 263 (9200).

Nuclear Magnetic Resonance Spectrum (hexadeuterated dimethyl sulfoxide) $\delta$ ppm:
  4.21 (1H, singlet);
  4.59 (1H, doublet, J=6.0 Hz);
  4.96 (1H, doublet, J=3.0 Hz);
  5.87 (1H, doublet of doublets, J=3.0 & 6.0 Hz);
  6.58 (1H, singlet);
  8.88 (2H, singlet).

EXAMPLE 56

6-Desamino-6-methoxygriseolic acid (Compound No. 124)

408 mg of dimethyl $O^{2'},O^{7'}$-diacetyl-6-chloro-6-desaminogriseolate (prepared as described in Example 51) were suspended in 16 ml of anhydrous methanol, and the mixture was cooled down to a temperature between $-20°$ and $-10°$ C. A 1N methanolic solution of sodium methoxide was then added and the mixture was stirred, whilst keeping the temperature below 0° C., for 2-2.5 hours. The solvent was then distilled off, and 4 ml of water were added. The mixture was stirred for 3 hours at room temperature, and then its pH was adjusted to a value of 2 with 3N hydrochloric acid. The precipitated crystals were collected by filtration to yield 251 mg (79.7%) of the title compound.

Ultraviolet Absorption Spectrum (H$_2$O) $\lambda_{max}$ nm ($\epsilon$):
  246 (12700).

Nuclear Magnetic Resonance Spectrum (hexadeuterated dimethyl sulfoxide) $\delta$ ppm:
  4.53 (1H, singlet);
  4.63 (1H, doublet, J=6.0 Hz);
  5.13 (1H, doublet, J=3.0 Hz);
  6.03 (1H, doublet of doublets, J=3.0 & 6.0 Hz);
  6.60 (1H, singlet);
  8.61 (1H, singlet);
  8.63 (1H, singlet).

EXAMPLE 57

6-Desamino-6-mercaptogriseolic acid (Compound No. 54)

1.0 g of $O^{2'},O^{7'}$-diacetyl-6-chloro-6-desaminogriseolic acid (prepared as described in Example 53) was dissolved in 30 ml of dimethylformamide. The air in the reaction vessel was replaced by nitrogen, and then 1.5 g of sodium hydrosulfide was added to the solution. The mixture was stirred overnight at room temperature. The mixture, under a stream of nitrogen gas, was acidified with concentrated hydrochloric acid and then the solvent was distilled off. 20 ml of a 1N aqueous solution of sodium hydroxide was added to the residue, and the mixture was kept standing overnight at room temperature. The pH of the solution was then adjusted to a value of 2 with concentrated hydrochloric acid, and then the mixture was purified by reverse phase chromatography through an Rp-8 prepacked column (Merck), to yield 0.44 g of the title compound.

Ultraviolet Absorption Spectrum (H$_2$O) $\lambda_{max}$ nm ($\epsilon$):
  321 (20300).

Nuclear Magnetic Resonance Spectrum (hexadeuterated dimethyl sulfoxide) $\delta$ ppm:
  4.51 (1H, singlet);
  4.58 (1H, doublet, J=6.0 Hz);
  5.14 (1H, doublet, J=3.0 Hz);
  5.81 (1H, doublet of doublets, J=3.0 & 6.0 Hz);
  6.51 (1H, singlet);
  8.30 (1H, singlet);
  8.50 (1H, singlet).

EXAMPLE 58

6-Desamino-6-hydrazinogriseolic acid (Compound No. 60)

1.0 g of 6-chloro-6-desaminogriseolic acid (prepared as described in Example 55) was dissolved in 120 ml of methanol. 1.85 ml of hydrazine hydrate was added to the solution, and the mixture was stirred at room temperature for 16-20 hours. The solvent was then distilled off, and the pH of the residue was adjusted to a value of 2 with 3N hydrochloric acid. The solution was purified by reverse phase chromatography through an Rp-8 prepacked column (Merck), to yield 0.5 g of the title compound (yield 50.7%).

Ultraviolet Absorption Spectrum (H$_2$O) $\lambda_{max}$ nm ($\epsilon$):
  265 (15500).

Nuclear Magnetic Resonance Spectrum (hexadeuterated dimethyl sulfoxide) $\delta$ ppm:
  4.50 (1H, singlet);
  4.59 (1H, doublet, J=6.0 Hz);
  5.09 (1H, doublet, J=3.0 Hz);
  6.05 (1H, doublet of doublets, J=3.0 & 6.0 Hz);
  6.52 (1H, singlet);

8.34 (1H, singlet);
8.37 (1H, singlet).

EXAMPLE 59

$N^6$-Methylgriseolic acid (Compound No. 58)

2.5 g of $O^{2'},O^{7'}$-diacetyl-6-chloro-6-desaminogriseolic acid (prepared as described in Example 53) were dissolved in 20 ml of methanol. 4 ml of a 40% w/v methanolic solution of methylamine were added to the resulting solution, and the mixture was stirred for 5 hours at room temperature. The solvent was then distilled off, and 20 ml of a 1N aqueous solution of sodium hydroxide were added to the residue. The mixture was left standing overnight at room temperature. The pH of the mixture was adjusted to a value of 2 with concentrated hydrochloric acid, and the mixture was left standing overnight in a cool place. The precipitated crystals were collected by filtration, to yield 1.45 g of the title compound.

Ultraviolet Absorption Spectrum (H$_2$O) $\lambda_{max}$ nm ($\epsilon$):
265 (17200).

Nuclear Magnetic Resonance Spectrum (hexadeuterated dimethyl sulfoxide) $\delta$ ppm:
4.52 (1H, singlet);
4.60 (1H, doublet, J=6.0 Hz);
5.10 (1H, doublet, J=3.0 Hz);
6.08 (1H, doublet of doublets, J=3.0 & 6.0 Hz);
6.53 (1H, singlet);
8.31 (1H, singlet);
8.35 (1H, singlet).

The procedure described in Example 59 was repeated, except that methylamine was replaced by the appropriate other amine, to prepare the compounds of Examples 60–68.

EXAMPLE 60

$N^6$-Dimethylgriseolic acid (Compound No. 59)

Ultraviolet Absorption Spectrum (H$_2$O) $\lambda_{max}$ nm ($\epsilon$):
273 (19800).

Nuclear Magnetic Resonance Spectrum (hexadeuterated dimethyl sulfoxide) $\delta$ ppm:
4.52 (1H, singlet);
4.58 (1H, doublet, J=6.0 Hz);
5.11 (1H, doublet, J=3.0 Hz);
6.02 (1H, doublet of doublets, J=3.0 & 6.0 Hz);
6.53 (1H, singlet);
8.30 (1H, singlet);
8.38 (1H, singlet).

EXAMPLE 61

$N^6$-Benzylgriseolic acid (Compound No. 63)

Ultraviolet Absorption Spectrum (50% v/v aqueous methanol) $\lambda_{max}$ nm ($\epsilon$):
267 (22000).

Nuclear Magnetic Resonance Spectrum (hexadeuterated dimethyl sulfoxide) $\delta$ ppm:
4.53 (1H, singlet);
4.61 (1H, doublet, J=6.0 Hz);
5.10 (1H, doublet, J=3.0 Hz);
6.07 (1H, doublet of doublets, J=3.0 & 6.0 Hz);
6.54 (1H, singlet);
8.30 (1H, singlet);
8.40 (1H, singlet).

EXAMPLE 62

$N^6$-Phenethylgriseolic acid (Compound No. 64)

Ultraviolet Absorption Spectrum (50% v/v aqueous methanol) $\lambda_{max}$ nm ($\epsilon$):
268 (18400).

Nuclear Magnetic Resonance Spectrum (hexadeuterated dimethyl sulfoxide) $\delta$ ppm:
4.55 (1H, singlet);
4.59 (1H, doublet, J=6.0 Hz);
5.10 (1H, doublet, J=3.0 Hz);
6.04 (1H, doublet of doublets, J=3.0 & 6.0 Hz);
6.50 (1H, singlet);
8.29 (1H, singlet);
8.33 (1H, singlet).

EXAMPLE 63

$N^6$-$\alpha$-Naphthylmethylgriseolic acid (Compound No. 65)

Ultraviolet Absorption Spectrum (50% v/v aqueous methanol) $\lambda_{max}$ nm ($\epsilon$):
271 (23200), 280 (22600), 293 shoulder (12500).

Nuclear Magnetic Resonance Spectrum (hexadeuterated dimethyl sulfoxide) $\delta$ ppm:
4.44 (1H, singlet);
4.59 (1H, doublet, J=6.0 Hz);
5.05 (1H, doublet, J=3.0 Hz);
6.03 (1H, doublet of doublets, J=3.0 & 6.0 Hz);
6.51 (1H, singlet);
8.30 (1H, singlet);
8.38 (1H, singlet).

EXAMPLE 64

6-Desamino-6-piperidinogriseolic acid (Compound No. 66)

Ultraviolet Absorption Spectrum (H$_2$O) $\lambda_{max}$ nm ($\epsilon$):
280 (21100).

Nuclear Magnetic Resonance Spectrum (hexadeuterated dimethyl sulfoxide) $\delta$ ppm:
4.52 (1H, singlet);
4.58 (1H, doublet, J=6.0 Hz);
5.11 (1H, doublet, J=3.0 Hz);
6.02 (1H, doublet of doublets, J=3.0 & 6.0 Hz);
6.52 (1H, singlet);
8.29 (1H, singlet);
8.36 (1H, singlet).

EXAMPLE 65

6-Desamino-6-morpholinogriseolic acid (Compound No. 67)

Ultraviolet Absorption Spectrum (H$_2$O) $\lambda_{max}$ nm ($\epsilon$):
279 (21900).

Nuclear Magnetic Resonance Spectrum (hexadeuterated dimethyl sulfoxide) $\delta$ ppm:
4.51 (1H, singlet);
4.57 (1H, doublet, J=6.0 Hz);
5.11 (1H, doublet, J=3.0 Hz);
6.01 (1H, doublet of doublets, J=3.0 & 6.0 Hz);
6.53 (1H, singlet);
8.33 (1H, singlet);
8.40 (1H, singlet).

EXAMPLE 66

$N^6$-Phenylgriseolic acid (Compound No. 125)

Ultraviolet Absorption Spectrum (50% v/v aqueous methanol) $\lambda_{max}$ nm ($\epsilon$):

291 (21700).
Nuclear Magnetic Resonance Spectrum (hexadeuterated dimethyl sulfoxide) δ ppm:
4.54 (1H, singlet);
4.66 (1H, doublet, J=6.0 Hz);
5.14 (1H, doublet, J=3.0 Hz);
6.10 (1H, doublet of doublets, J=3.0 & 6.0 Hz);
6.59 (1H, singlet);
8.46 (1H, singlet);
8.56 (1H, singlet).

EXAMPLE 67

$N^6$-(2-Hydroxyethyl)griseolic acid (Compound No. 61)

Ultraviolet Absorption Spectrum ($H_2O$) $\lambda_{max}$ nm ($\epsilon$): 265 (18400).
Nuclear Magnetic Resonance Spectrum (hexadeuterated dimethyl sulfoxide) δ ppm:
4.48 (1H, singlet);
4.57 (1H, doublet, J=6.0 Hz);
5.08 (1H, doublet, J=3.0 Hz);
6.04 (1H, doublet of doublets, J=3.0 & 6.0 Hz);
6.51 (1H, singlet);
8.28 (1H, singlet);
8.36 (1H, singlet).

EXAMPLE 68

$N^6$-(2-Aminoethyl)griseolic acid (Compound No. 62)

Ultraviolet Absorption Spectrum ($H_2O$) $\lambda_{max}$ nm ($\epsilon$): 264 (18700).
Nuclear Magnetic Resonance Spectrum (hexadeuterated dimethyl sulfoxide) δ ppm:
4.15 (1H, singlet);
4.48 (1H, doublet, J=6.0 Hz);
4.86 (1H, doublet, J=3.0 Hz);
5.89 (1H, doublet of doublets, J=3.0 & 6.0 Hz);
6.45 (1H, singlet);
8.32 (1H, singlet);
8.39 (1H, singlet).

EXAMPLE 69

6-Desamino-6-hydrogriseolic acid (Compound No. 53)

1.83 g of dibenzhydryl 6-chloro-6-desaminogriseolate (prepared as described in Example 54) was dissolved in an 80% w/v aqueous solution of acetic acid, and 5 g of zinc powder was added to the solution. The mixture was stirred at room temperature for 3-4 hours. The solvent was then distilled off, and the residue was dissolved in a mixture of ethyl acetate and water. The ethyl acetate layer was separated and washed with a 20% w/v aqueous solution of sodium bicarbonate and then with a saturated aqueous solution of sodium chloride, after which it was dried over anhydrous magnesium sulfate. The solution was collected by filtration and the solvent was distilled off. The residue was dissolved in a mixture of ethyl acetate and water. The ethyl acetate layer was separated and washed with a 20% w/v aqueous solution of sodium bicarbonate and then with a saturated aqueous solution of sodium chloride, after which it was dried over anhydrous magnesium sulfate. The solution was collected by filtration and the solvent was distilled off. The residue was purified by silica gel chromatography, to yield 1.9 g of the dibenzhydryl ester of the title compound.

1.2 g of this dibenzhydryl ester was dissolved in 6 ml of anisole, and 6 ml of trifluoroacetic acid were added, with ice-cooling, to the solution. The mixture was left standing for 15 minutes, and then the solvent was distilled off. A mixture of acetone and toluene was added to the residue and then this solvent was distilled off. This process was repeated, and then a small quantity of benzene was added to the solution, after which it was added, with stirring, to 200 ml of hexane to precipitate a powder. The powder was collected by filtration and dissolved in an aqueous solution of sodium bicarbonate. The pH of the resulting solution was adjusted to a value of 2, after which the solution was purified by reverse phase chromatography through an Rp-8 prepacked column (Merck), to yield 0.5 g of the title compound.

Ultraviolet Absorption Spectrum ($H_2O$) $\lambda_{max}$ nm ($\epsilon$): 262 (7300).
Nuclear Magnetic Resonance Spectrum (hexadeuterated dimethyl sulfoxide) δ ppm:
4.53 (1H, singlet);
4.72 (1H, doublet, J=6.0 Hz);
5.15 (1H, doublet, J=3.0 Hz);
5.89 (1H, doublet of doublets, J=3.0 & 6.0 Hz); 6.45 (1H, singlet);
8.32 (1H, singlet);
8.39 (1H, singlet).

EXAMPLE 70

Dibenzhydryl $O^{2'}$-benzoyl-$O^{7'}$-mesylgriseolate (Compound No. 77)

2.17 g of dibenzhydryl $O^{2'}$-benzoylgriseolate (prepared as described in Example 15) were dissolved in 30 ml of anhydrous pyridine; to the resulting solution was added 0.693 ml of methanesulfonyl chloride, with ice-cooling. The mixture was left standing for 15 hours at room temperature, and then, whilst ice-cooling, 3 ml of water were added to the reaction mixture. The mixture was stirred for 30 minutes. The solvent was then distilled off under reduced pressure, and the residue was dissolved in ethyl acetate. The solution was washed with water and then with a saturated aqueous solution of sodium chloride. The organic layer was separated, dried and promptly treated with activated carbon. The solvent was distilled off to yield a pale yellow residue. The residue was dissolved in a small quantity of methylene chloride, to which ethanol was then added. On slowly condensing the mixture under reduced pressure by an aspirator, a white precipitate formed; this was collected by filtration and dried to yield 1.30 g of the title compound.

Ultraviolet Absorption Spectrum (methanol) $\lambda_{max}$ nm ($\epsilon$):
258 (17400).
Nuclear Magnetic Resonance Spectrum (hexadeuterated dimethyl sulfoxide) δ ppm:
5.23 (1H, doublet, J=3.0 Hz);
5.84 (1H, singlet);
6.02 (1H, doublet, J=6.0 Hz);
8.13 (1H, singlet);
8.35 (1H, singlet).

EXAMPLE 71

Dibenzhydryl $O^{2'}$-benzoyl-$O^{7'}$-trifluoromethanesulfonylgriseolate (Compound No. 79)

7.99 g of dibenzhydryl $O^{2'}$-benzoylgriseolate (prepared as described in Example 15) and 1.46 g of 4-(dimethylamino)pyridine were introduced into a 100 ml three-neck round-bottomed flask, which was then dried under reduced pressure in the presence of phosphorus pentoxide. Also in the presence of phosphorus pentoxide, 50 ml of methylene chloride was separately distilled, and then added to the three-neck flask. 2.02 ml of trifluoromethanesulfonyl chloride were then added whilst ice-cooling and protecting from moisture, and the mixture was stirred for 2 hours under the same conditions. After adding 10 ml of water, the mixture was stirred for a further 15 minutes, whilst ice-cooling. The reaction product was then transferred to a separating funnel, to which 20 ml of 0.1N hydrochloric acid was added to wash the organic layer. This layer was then washed with a saturated aqueous solution of sodium chloride and then with a saturated aqueous solution of sodium bicarbonate, after which it was dried over anhydrous sodium sulfate. The solvent was distilled off under reduced pressure. The resulting residue was purified by silica gel column chromatography, using methylene chloride containing 1% v/v methanol as the eluent. The fractions containing the main product were collected and condensed. The condensate was lyophilized from benzene to yield 7.38 g of the title compound as a pale yellow solid.

Ultraviolet Absorption Spectrum (methanol) $\lambda_{max}$ nm ($\epsilon$):
257 (17100).

Nuclear Magnetic Resonance Spectrum (hexadeuterated dimethyl sulfoxide) $\delta$ ppm:
5.21 (1H, doublet, J=3.0 Hz);
6.00 (1H, doublet, J=6.0 Hz);
6.05 (1H, singlet);
8.08 (1H, singlet);
8.33 (1H, singlet).

EXAMPLE 72

Dibenzhydryl 7'(S)-azido-$O^{2'}$-benzoyl-7'-deoxygriseolate (Compound No. 130)

935 mg of dibenzhydryl $O^{2'}$-benzoyl-$O^{7'}$-trifluoromethanesulfonylgriseolate (prepared as described in Example 71) were dissolved in 5 ml of well-dried hexamethylphosphoric triamide, to which 68.3 mg of well-dried sodium azide (which had been obtained by lyophilization from water) were then added. The mixture was reacted at room temperature for 2 hours, whilst protecting it from moisture. The reaction product was then poured into ice-water, and the resulting insoluble matter was collected by filtration, washed with water and dried. The resulting solid material was purified by silica gel preparative thin layer chromatography. The main bands were extracted and the extract was lyophilized from benzene to yield 455 mg of the title compound in the form of a pale yellow powder. The compound showed an extremely strong infrared absorption spectrum peak due to azide at 2100 cm.$^{-1}$.

Ultraviolet Absorption Spectrum (methanol) $\lambda_{max}$ nm ($\epsilon$):
257 (18900).

Nuclear Magnetic Resonance Spectrum (hexadeuterated dimethyl sulfoxide) $\delta$ ppm:
4.87 (1H, singlet);
5.34 (1H, doublet, J=3.0 Hz);
5.85 (1H, doublet, J=6.0 Hz);
6.93 (1H, singlet);
8.11 (1H, singlet);
8.36 (1H, singlet).

EXAMPLE 73

7'-Azido-7'-deoxygriseolic acid (Compound No. 81)

300 mg of dibenzhydryl 7'-azido-$O^{2'}$-benzoyl-7'-deoxygriseolate (prepared as described in Example 72) were dissolved in 5 ml of anisole. 5 ml of trifluoroacetic acid were added, with ice-cooling, to the resulting solution, and the mixture was left standing for 30 minutes in a tightly stoppered vessel. The solvent was then distilled off under reduced pressure. The residue was dissolved in acetone, to which toluene was then added and the solvent was distilled off. This process was repeated 3 times. The residue was dissolved in 10 ml of acetone, and the solution was poured into 100 ml of hexane. The resulting precipitate was collected by filtration, thoroughly washed with hexane, and then dried. The resulting pale yellow solid was dissolved in 20 ml of a 20% w/v solution of ammonia in methanol, and the mixture was left standing overnight. The solvent was distilled off under reduced pressure and the resulting residue was dissolved in a small guantity of water. The pH of the resulting solution was adjusted to a value of 2.0 and then the solution was washed with a small quantity of diethyl ether, and subjected to column chromatography through an Rp-8 column (Merck). The column was washed with water, and then eluted with water containing 10% v/v acetonitrile. The main peaks were collected and the solvent was distilled off. The resulting residue was lyophilized from water to yield 70 mg of the title compound in the form of a pale yellow granular substance. The infrared absorption spectrum of this compound showed a strong peak at 2110 cm$^{-1}$ which was ascribable to azide.

Ultraviolet Absorption Spectrum (methanol) $\lambda_{max}$ nm ($\epsilon$):
258 (14700).

Nuclear Magnetic Resonance Spectrum (hexadeuterated dimethyl sulfoxide) $\delta$ppm:
4.27 (1H, singlet);
4.61 (1H, doublet, J=6.0 Hz);
5.01 (1H, doublet, J=3.0 Hz);
6.08 (1H, doublet of doublets, J=3.0 & 6.0 Hz);
6.50 (1H, singlet);
8.21 (1H, singlet);
8.36 (1H, singlet).

EXAMPLE 74

6-Desamino-6-methylmercaptogriseolic acid (Compound No. 55)

0.44 g of 6-desamino-6-mercaptogriseolic acid (prepared as described in Example 57) was dissolved in 20 ml of a 1N aqueous solution of sodium hydroxide, and 0.4 ml of methyl iodide was added to the resulting solution. The mixture was left standing overnight at room temperature. The solvent was then distilled off, and the pH of the residue was adjusted to a value of 2.5. The resulting solution was purified by reverse phase chromatography through an Rp-8 prepacked column (Merck), to yield 0.4 g of the title compound.

Ultraviolet Absorption Spectrum (H$_2$O) $\lambda_{max}$ nm ($\epsilon$):
299 (20500).

Nuclear Magnetic Resonance Spectrum (hexadeuterated dimethyl sulfoxide) $\delta$ppm:
4.53 (1H, singlet);
4.64 (1H, doublet, J=6.0 Hz);
5.16 (1H, doublet, J=3.0 Hz);
6.03 (1H, doublet of doublets, J=3.0 & 6.0 Hz);

6.62 (1H, singlet);
8.68 (1H, singlet);
8.83 (1H, singlet).

EXAMPLE 75

6-Azido-6-desaminogriseolic acid (Compound No. 56)

0.26 g of 6-desamino-6-hydrazinogriseolic acid (prepared as described in Example 58) was dissolved in 4 ml of a 5% w/v aqueous solution of acetic acid, to which was then added 0.052 g of sodium nitrite dissolved in 10 ml of water, with ice-cooling and under a stream of nitrogen gas. The mixture was stirred for 2 hours under the same conditions. The pH of the mixture was then adjusted to a value of 2.0 with 3N hydrochloric acid. The mixture was purified by reverse phase chromatography through an Rp-8 prepacked column (Merck), to yield 0.18 g of the title compound.

Ultraviolet Absorption Spectrum (H$_2$O) $\lambda_{max}$ nm ($\epsilon$):
251 (4900), 259 (5100), 287 (8700), 300 shoulder (5100).

Nuclear Magnetic Resonance Spectrum (hexadeuterated dimethyl sulfoxide) $\delta$ppm:
4.53 (1H, singlet);
4.66 (1H, doublet, J=6.0 Hz);
5.21 (1H, doublet, J=3.0 Hz);
5.90 (1H, doublet of doublets, J=3.0 & 6.0 Hz);
6.75 (1H, singlet);
8.89 (1H, singlet);
10.28 (1H, singlet).

EXAMPLE 76

N$^6$-Methoxygriseolic acid (Compound No. 57)

1.0 g of 6-chloro-6-desaminogriseolic acid (prepared as described in Example 55) was suspended in methanol, and then the air in the reaction vessel containing the suspension was replaced by nitrogen. 2.3 g of methoxyamine were added to this suspension, and the mixture was reacted at 60° C. for 7 hours, and then a further 1.8 g of methoxyamine was added to the mixture and the mixture was reacted at 80° C. for a further 15 hours. The solvent was then distilled off and the pH of the solution was adjusted to a value of 3.0. The solution was then purified by reverse phase chromatography through an Rp-8 prepacked column (Merck), to yield 0.28 g of the title compound.

Ultraviolet Absorption Spectrum (H$_2$O) $\lambda_{max}$ nm ($\epsilon$):
267 (13300).

Nuclear Magnetic Resonance Spectrum (hexadeuterated dimethyl sulfoxide) $\delta$ ppm:
4.25 (1H, singlet);
4.46 (1H, doublet, J=6.0 Hz);
4.92 (1H, doublet, J=3.0 Hz);
5.79 (1H, doublet of doublets, J=3.0 & 6.0 Hz);
6.37 (1H, singlet);
7.71 (1H, singlet);
8.13 (1H, singlet).

EXAMPLE 77

N$^1$-Butylgriseolic acid (Compound No. 44)

4.0 g of dibenzhydryl O$^{2'}$,O$^{7'}$-diacetylgriseolate (prepared as described in Example 20) were dissolved in dimethylformamide, 12.8 ml of butyl iodide were added, with ice-cooling, to the resulting solution, and the mixture was reacted at 70° C. for 48 hours. The solvent was then evaporated off under reduced pressure, and the residue was extracted with a mixture of a saturated aqueous solution of sodium bicarbonate and methylene chloride. The organic layer was separated, dried over anhydrous magnesium sulfate and then evaporated to dryness under reduced pressure. The residue was purified by silica gel chromatography using a solution of 5% v/v methanol in methylene chloride as the eluent, to give 3.3 g of the N$^1$-butyl derivative with protected hydroxy and carboxyl groups.

A 20% w/v solution of ammonia in methanol was added, with ice-cooling, to 2.5 g of this compound, and the mixture was left standing for 1 hour, with ice-cooling. The solvent was then distilled off under reduced pressure. A solution of diphenyldiazomethane in acetone was added to the residue, and the mixture was left standing for 30 minutes at room temperature. The resulting solution was evaporated to dryness. The residue was purified by silica gel column chromatography using a 7% v/v solution of methanol in methylene chloride as the eluent, to yield 1.7 g of dibenzhydryl N$^1$-butylgriseolate.

10 ml of trifluoroacetic acid was added, whilst ice-cooling, to a solution of 1.2 g of this compound in anisole, and the mixture was left standing at room temperature for 10 minutes. The solvent was then distilled off under reduced pressure. Toluene was added to the residue, and the solution was evaporated to dryness under reduced pressure. This process was repeated twice. The residue was purified by reverse phase column chromatography through an Rp-8 prepacked column, using a mixture of 3% v/v acetonitrile, 0.02% v/v acetic acid and water as the eluent, to yield 400 mg of the title compound.

Ultraviolet Absorption Spectrum (50% v/v aqueous methanol) $\lambda_{max}$ nm ($\epsilon$):
258 (14700).

Nuclear Magnetic Resonance Spectrum (hexadeuterated dimethyl sulfoxide) $\delta$ ppm:
4.21 (1H, singlet);
4.54 (1H, doublet, J=6.0 Hz);
4.75-5.20 (2H);
5.78 (1H, doublet of doublets, J=3.0 & 6.0 Hz); 6.53 (1H, singlet);
8.65 (1H, singlet);
8.70 (1H, singlet).

EXAMPLE 78

N$^1$-Allylgriseolic acid (Compound No. 48)

4.0 g of dibenzhydryl O$^{2'}$,O$^{7'}$-diacetylgriseolate (prepared as described in Example 20) were dissolved in dimethylformamide. 9.4 ml of allyl iodide were added, with ice-cooling, to the solution. The resulting mixture was reacted at room temperature for 24 hours. The solvent was then distilled off under reduced pressure, and the residue was extracted with a mixture of a saturated aqueous solution of sodium bicarbonate and methylene chloride. The organic layer was separated, dried over anhydrous magnesium sulfate and then evaporated to dryness under reduced pressure. The residue was purified by silica gel column chromatography using a 5:95 by volume mixture of methanol and methylene chloride as the eluent, to yield 3.2 g of the N$^1$-butyl derivative with protected hydroxy and carboxyl groups.

A 20% w/v solution of ammonia in methanol was added, with ice-cooling, to 2.5 g of this compound, and the mixture was left standing for 1 hour, with ice-cooling. The solvent was then distilled off under reduced pressure. A solution of diphenyldiazomethane in acetone was added to the residue and the mixture was left standing for 30 minutes and was then evaporated to dryness. The residue was purified by silica gel column chromatography using a 7:93 by volume mixture of methanol and methylene chloride as the eluent, to yield 2.0 g of dibenzhydryl $N^1$-allylgriseolate.

10 ml of trifluoroacetic acid was added, with ice-cooling, to a solution of 1.5 g of this compound in anisole. The mixture was left standing for 10 minutes at room temperature, and then the solvent was distilled off under reduced pressure. Toluene was added to the residue and the mixture was evaporated to dryness. This process was repeated twice. The residue was purified by reverse column chromatography through an Rp-8 prepacked column, using a 3:0.02:96.98 by volume mixture of acetonitrile, acetic acid and water as the eluent, to yield 370 mg of the title compound.

Ultraviolet Absorption Spectrum (50% v/v aqueous methanol) $\lambda_{max}$ nm ($\epsilon$):
259 (14700).

Nuclear Magnetic Resonance Spectrum (hexadeuterated dimethyl sulfoxide) $\delta$ ppm:
4.17 (1H, singlet);
4.55 (1H, doublet, J=6.0 Hz);
5.02 (1H, doublet, J=3.0 Hz);
5.80 (1H, doublet of doublets, J=3.0 & 6.0 Hz);
6.55 (1H, singlet);
8.63 (1H, singlet);
8.70 (1H, singlet).

EXAMPLE 79

7'-Chloro-7'-deoxygriseolic acid (Compound No. 88)

2.84 g of dibenzhydryl $O^{2'}$-benzoyl-$O^{7'}$-trifluoromethanesulfonylgriseolate (prepared as described in Example 71) were dissolved in 50 ml of dimethylformamide, and then 1.27 g of anhydrous lithium chloride was added, and the mixture was stirred, whilst heating at 100° C., for 1 hour. It was then confirmed that there was no starting material left (using silica gel thin layer chromatography, with methylene chloride containing 5% v/v methanol as the developing solvent), and the solvent was distilled off under reduced pressure. The resulting residue was dissolved in 30 ml of water and 50 ml of ethyl acetate, and the organic layer was separated. This was washed with water and dried over anhydrous magnesium sulfate, and the solvent was evaporated off, to yield a pale brown residue. The residue was separated and purified by silica gel column chromatography, to yield 1.74 g of a pale yellow caramel-like substance, which was the title compound but with its hydroxy group and its carboxy group protected.

1.34 g of this compound was dissolved in 10 ml of anisole, and then trifluoroacetic acid was added, with ice-cooling. The mixture was left standing for 30 minutes at room temperature. The solvent was then distilled off under reduced pressure, and the residue was dissolved in acetone. Toluene was added to the solution and then distilled off. This process was repeated 3 times. The residue was dissolved in a small quantity of acetone, and the resulting solution was slowly poured, with stirring, into 100 ml of hexane. The resulting white precipitate was collected by filtration and dried to yield 860 mg of a white powder. This white powder was dissolved in 20 ml of a 20% w/v solution of ammonia in methanol, and the solution was left standing for 2 hours at room temperature in a tightly stoppered vessel. The solvent was then distilled off under reduced pressure and the residue was dissolved in 30 ml of water. The resulting solution was washed twice, each time with 20 ml of diethyl ether, and then its pH was adjusted to a value of 2.0 using concentrated hydrochloric acid. The solution was purified by chromatography through an Rp-8 prepacked column (Merck). The fractions containing the title compound were collected and lyophilized to yield 525 mg of the title compound in the form of a pale yellowish powder.

Ultraviolet Absorption Spectrum (H$_2$O) $\lambda_{max}$ nm ($\epsilon$):
257 (16500).

Nuclear Magnetic Resonance Spectrum (hexadeuterated dimethyl sulfoxide) $\delta$ ppm:
4.70 (1H, doublet, J=6.0 Hz);
4.97 (1H, singlet);
5.25 (1H, doublet, J=3.0 Hz);
6.10 (1H, doublet of doublets, J=3.0 & 6.0 Hz);
6.58 (1H, singlet);
8.31 (1H, singlet);
8.42 (1H, singlet).

EXAMPLE 80

7'-Deoxygriseolic acid (Compound No. 133)

500 mg of 7'-chloro-7'-deoxygriseolic acid (prepared as described in Example 79) were dissolved in 30 ml of 80% aqueous acetic acid. 600 mg of zinc powder were then added in 3 approximately equal portions at intervals of 1 hour, with violent stirring. The stirring was continued under the same conditions. The insoluble matter was removed by filtration, and the filtrate was evaporated to dryness. The pH of the resulting residue was adjusted to a value of 2.0 using 1N hydrochloric acid. The solution was then purified using an Rp-8 prepacked column (Merck), and then lyophilized from water, to yield 250 mg of the title compound in the form of a white powder.

Ultraviolet Absorption Spectrum (H$_2$O) $\lambda_{max}$ nm ($\epsilon$):
260 (16000).

Nuclear Magnetic Resonance Spectrum (hexadeuterated dimethyl sulfoxide) $\delta$ ppm:
2.92 (1H, quartet);
4.59 (1H, doublet, J=5.0 Hz);
5.08 (1H, doublet, J=2.4 Hz);
5.99 (1H, doublet of doublets, J=2.4 & 5.0 Hz);
6.46 (1H, singlet);
8.23 (1H, singlet);
8.33 (1H, singlet).

EXAMPLE 81

Dibenzhydryl 7'(S)-amino-$O^{2'}$-benzoyl-7'-deoxygriseolate (Compound No. 134)

1.20 g of dibenzhydryl 7'-azido-$O^{2'}$-benzoyl-7'-deoxygriseolate (prepared as described in Example 72) was dissolved in 15 ml of pyridine, to which 5 ml of water was then added. Nitrogen gas was passed through the mixture for approximately 5 minutes, and then hydrogen sulfide gas was passed through it for 30 minutes, whilst ice-cooling. The air in the flask was replaced by nitrogen gas, and the reaction product was left standing at room temperature for 17 hours in a tightly stoppered vessel. Nitrogen gas was then passed through the reaction product for 1 hour at room temperature to remove excess hydrogen sulfide gas. 10 ml of acetic acid were added to the reaction product, and then the solvent was distilled off under reduced pressure. 10 ml of ethanol was added to the residue, and then distilled off. This process was repeated once. The residue was then dissolved in 30 ml of ethyl acetate and 20 ml of water, and then subjected to fractionation of the organic and aqueous layers. The organic layer was washed with 20 ml each of 0.1N hydrochloric acid, a 5% w/v aqueous solution of sodium bicarbonate and a saturated aqueous solution of sodium chloride (in that order) and then dried over anhydrous magnesium sulfate. The solvent was distilled off under reduced pressure to yield a pale yellow residue. This residue was purified by chromatography through an Rp-8 prepacked column of silica gel (Merck), using methylene chloride containing 2% v/v methanol as the eluent. The main peak material was lyophilized with benzene, to yield 494 mg of the title compound in the form of a pale yellow solid.

Ultraviolet Absorption Spectrum (H$_2$O) $\lambda_{max}$ nm ($\epsilon$): 260 (18200).

Nuclear Magnetic Resonance Spectrum (hexadeuterated dimethyl sulfoxide) $\delta$ ppm:
4.07 (1H, singlet);
5.47 (1H, doublet, J=3.0 Hz);
5.90 (1H, doublet, J=3.0 Hz);
6.63 & 6.66 (1H, singlet);
8.15 (1H, singlet);
8.43 (1H, singlet).

EXAMPLE 82

7'(S)-Amino-7'-deoxygriseolic acid (Compound No. 135)

434 mg of dibenzhydryl 7'(S)-amino-O$^{2'}$-benzoyl-7'-deoxygriseolate (prepared as described in Example 81) were dissolved in 5 ml of anisole. 5 ml of trifluoroacetic acid were added, with ice-cooling, to the resulting solution, and the mixture was left standing for 30 minutes at room temperature in a tightly stoppered vessel. The solvent was distilled off under reduced pressure. 5 ml of acetone and 5 ml of toluene were added to the residue and were then distilled off. This process was repeated 3 times. The resulting residue was dissolved in 5 ml of ethanol and 5 ml of acetone, and the solution was slowly poured into 50 ml of a 50% v/v mixture of hexane and acetone, with stirring. The resulting precipitate was collected by filtration, washed with hexane and dried. The resulting ochre-colored powder was dissolved in 20 ml of a 20% v/v solution of ammonia in methanol, and left standing for 17 hours at room temperature in a tightly stoppered vessel. The solvent was distilled off under reduced pressure, and 20 ml of water was added to the residue to dissolve it. The resulting solution was gradually acidified with 1N hydrochloric acid, whereupon insoluble matter first appeared but then dissolved when the pH reached a value of 1. The solution was washed with 20 ml of ethyl acetate. The pH of the aqueous layer was adjusted to a value of about 7 by adding sodium bicarbonate. The aqueous layer was then purified by chromatography through an Rp-8 prepacked column (Merck). The main peaks were collected and lyophilized from water to yield 133 mg of the title compound in the form of a pale yellow solid.

Ultraviolet Absorption Spectrum (methanol) $\lambda_{max}$ nm ($\epsilon$):
206 (25800), 257.5 (15100).

EXAMPLE 83

Dibenzhydryl O$^{2'}$-benzoyl-7'(S)-bromo-7'-deoxygriseolate (Compound No. 136)

14.1 g of dibenzhydrl O$^{2'}$-benzoyl-O$^{7'}$-trifluoromethanesulfonylgriseolate (prepared as described in Example 71) were dissolved in 50 ml of dimethylformamide. 13 g of lithium bromide were added to the resulting solution, and the mixture was heated at 95° C. for 22 minutes. The solvent was then distilled off, and ethyl acetate and water were added to the residue. The organic layer was separated, washed with a saturated aqueous solution of sodium chloride and dried over anhydrous magnesium sulfate. The dried solution was filtered, and the solvent was distilled from the filtrate. The residue was purified by silica gel chromatography, to yield 6.9 g of the title compound.

Ultraviolet Absorption Spectrum (H$_2$O) $\lambda_{max}$ nm ($\epsilon$): 258 (17200).

Nuclear Magnetic Resonance Spectrum (hexadeuterated dimethyl sulfoxide) $\delta$ ppm:
5.13 (1H, singlet);
5.40 (1H, doublet, J=2.4 Hz);
5.97 (1H, doublet, J=6.0 Hz);
6.67 (1H, singlet);
6.75 (1H, quartet, J=2.4 & 6.0 Hz);
8.09 (1H, singlet);
8.40 (1H, singlet).

EXAMPLE 84

7'(S)-Bromo-7'-deoxygriseolic acid (Compound No. 137)

878 mg of dibenzhydryl O$^{2'}$-benzoyl-7'(S)-bromo-7'-deoxygriseolate (prepared as described in Example 83) were dissolved in 10 ml of anisole. 10 ml of trifluoroacetic acid were added, with ice-cooling, to the resulting solution, and the mixture was left standing for 30 minutes at room temperature. The solvent was then distilled off under reduced pressure. 5 ml of acetone and 5 ml of toluene were added to the residue and were then distilled off. This process was repeated 3 times. The residue was dissolved in a small quantity of acetone. The resulting solution was slowly poured into 100 ml of hexane, with stirring. The resulting precipitate was collected by filtration, washed with hexane and dried. The precipitate was then dissolved in 20 ml of a 20% w/v solution of ammonia in methanol, and left standing for 17 hours in a tightly stoppered vessel. The solvent was distilled off under reduced pressure. The resulting residue was dissolved in water and the pH of the solution was adjusted to a value of 2.3. The aqueous solution was then purified by chromatography through an Rp-8 prepacked column (Merck), to yield 250 mg of the title compound.

Ultraviolet Absorption Spectrum (methanol) $\lambda_{max}$ nm ($\epsilon$):
257 (16000).

Nuclear Magnetic Resonance Spectrum (hexadeuterated dimethyl sulfoxide) $\delta$ ppm:
4.83 (1H, doublet, J=5.7 Hz);
5.13 (1H, singlet);
6.31 (1H, doublet, J=2.1 Hz);
6.52 (1H, quartet, J=2.1 & 5.7 Hz);
6.80 (1H, singlet);
8.26 (1H, singlet);
8.47 (1H, singlet).

EXAMPLE 85

6-Desamino-7'-deoxy-6-hydroxygriseolic acid (Compound No. 138)

300 mg of 7'-deoxygriseolic acid (prepared as described in Example 80) were dissolved, with heating, in 100 ml of 80% v/v aqueous acid. Nitrogen gas was then passed through the solution for 15 minutes. The solution was ice-cooled, and then 600 mg of sodium nitrite were added and the mixture was left standing for 24 hours at room temperature in a tightly stoppered vessel. Nitrogen gas was then passed through the mixture for 30 minutes, after which the solvent was distilled off under reduced pressure. 10 ml each of acetone and toluene were added to the resulting residue, and were then distilled off. This process was repeated 3 times. 30 ml of water was added to the residue, and then the pH of the solution was adjusted to a value of 0.5 with concentrated hydrochloric acid, whilst ice-cooling. The mixture was then evaporated to dryness. The residue was dissolved in 50 ml of water, and the aqueous solution was purified by chromatography through an Rp-8 prepacked column, using water containing 10% v/v acetonitrile as the eluent. The main peak material was collected and lyophilized to yield 260 mg of the title compound as a white powder.

Ultraviolet Absorption Spectrum (methanol) $\lambda_{max}$ nm ($\epsilon$):
248 (12500).

Nuclear Magnetic Resonance Spectrum (hexadeuterated dimethyl sulfoxide) $\delta$ ppm:
2.68, 2.87, 3.00, & 3.19 (2H, quartet, J=17.0 Hz);
4.57 (1H, doublet, J=5.1 Hz);
5.13 (1H, doublet, J=2.4 Hz);
5.87 (1H, quartet, J=2.4 & 5.1 Hz);
6.48 (1H, singlet);
8.20 (1H, singlet);
8.30 (1H, singlet).

EXAMPLE 86

Dibenzhydryl 7'(S)-acetoxy-O²'-benzoyl-7'-deoxygriseolate (Compound No. 139)

3.2 g of sodium acetate (which had previously been melted and dried) were dissolved, whilst heating at 95° C., in 50 ml of acetic acid. 3.79 g of dibenzhydryl O²'-benzoyl-O⁷'-trifluoromethanesulfonylgriseolate (prepared as described in Example 71) were added, and the mixture was stirred for 1 hour at 95° C., whilst protecting it from moisture. The solvent was distilled off under reduced pressure, and 10 ml each of acetone and toluene were added to the residue, and were then distilled off. This process was repeated 3 times. The residue was dissolved in acetone containing 10% v/v water. The pH of the solution was adjusted to a value no greater than 1, using 1N hydrochloric acid, and then diphenyldiazomethane was added to the mixture until the reddish color disappeared. The mixture was allowed to react at room temperature for approximately 1 hour, and then excess diphenyldiazomethane was destroyed with acetic acid. The solvent was distilled off under reduced pressure. The residue was dissolved in 50 ml of ethyl acetate and 50 ml of water, and subjected to fractionation. The organic layer was washed with a 5% w/v aqueous solution of sodium bicarbonate and a saturated aqueous solution of sodium chloride and dried over anhydrous magnesium sulfate. The drying agent was removed by filtration, and the solvent was distilled off. The residue was purified by silica gel column chromatography, to yield 2.33 g of the title compound in the form of a pale yellow caramel-like substance.

Ultraviolet Absorption Spectrum (H₂O) $\lambda_{max}$ nm ($\epsilon$):
257 (18100).

Nuclear Magnetic Resonance Spectrum (hexadeuterated dimethyl sulfoxide) $\delta$ ppm:
5.32 (1H, doublet, J=2.4 Hz);
5.91 (1H, doublet, J=5.4 Hz);
6.00 (1H, singlet);
8.14 (1H, singlet);
8.38 (1H, singlet).

EXAMPLE 87

7'-Deoxy-7'(S)-hydroxygriseolic acid (Compound No. 140)

2.23 g of dibenzhydryl 7'(S)-acetoxy-O²'-benzoyl-7'-deoxygriseolate (prepared as described in Example 86) were dissolved in 20 ml of anisole and 20 ml of trifluoroacetic acid, and the mixture was left standing for 1 hour, whilst ice-cooling. The solvent was then distilled off under reduced pressure. 10 ml each of acetone and toluene were added to the residue, and then distilled off. This process was repeated 3 times. The resulting white residue was dissolved in 20 ml of acetone, and the solution as slowly poured into 300 ml of hexane, with stirring. The resulting precipitate was collected by filtration and dried to yield 690 mg of a white powder. The white powder was dissolved in 30 ml of a 20% w/v solution of ammonia in methanol and left standing overnight. The solvent was distilled off under reduced pressure. The resulting residue was dissolved in water, and the pH of the aqueous solution was adjusted to a value of 2.3 with concentrated hydrochloric acid. The solution was further purified by reverse phase chromatography through an Rp-8 column (Merck). The initial peak material was collected and lyophilized from water containing 10% v/v acetonitrile, to yield 300 mg of the title compound in the form of a pale yellow powder.

Ultraviolet Absorption Spectrum (H₂O) $\lambda_{max}$ nm ($\epsilon$):
205 (27200), 256.5 (16200).

Nuclear Magnetic Resonance Spectrum (hexadeuterated dimethyl sulfoxide) $\delta$ ppm:
4.53 (1H, singlet);
4.62 (1H, doublet, J=5.1 Hz);
5.11 (1H, doublet, J=2.4 Hz);
6.06 (1H, quartet, J=2.4 & 5.1 Hz);
6.54 (1H, singlet);
8.27 (1H, singlet);
8.40 (1, singlet).

EXAMPLE 88

7'(S)-Acetoxy-7'-deoxygriseolic acid (Compound No. 141)

In the process of purification with an Rp-8 column described in Example 87, the second peak material eluted with water containing 10% v/v acetonitrile was collected and lyophilized to yield 200 mg of the title compound in the form of a pale yellow powder.

Ultraviolet Absorption Spectrum (H₂O) $\lambda_{max}$ nm ($\epsilon$):
205 (27700), 257 (16100).

Nuclear Magnetic Resonance Spectrum (hexadeuterated dimethyl sulfoxide) $\delta$ ppm:
4.63 (1H, doublet, J=5.1 Hz);
5.13 (1H, doublet, J=2.1 Hz);
5.49 (1H, singlet);

6.07 (1H, quartet, J=2.1 & 5.1 Hz);
6.56 (1H, singlet);
8.23 (1H, singlet);
8.38 (1H, singlet).

EXAMPLE 89

Dimethyl $O^{2'}$-benzoylgriseolate (Compound No. 76)

28.6 g of $O^{2'}$-benzoylgriseolic acid (prepared as described in Example 14) were suspended in 500 ml of methanol, and 41.2 ml of benzoyl chloride were added dropwise over about 15 minutes, with ice-cooling and stirring. The mixture was stirred for 1 hour under the same conditions, and then stirred for another 26 hours at room temperature. The solvent was then distilled off, and the residue was dissolved in a mixture of ethyl acetate with a 20% w/v aqueous solution of sodium bicarbonate. The organic layer was then separated, washed with water and dried over anhydrous magnesium sulfate, and the solvent was distilled off. The residue was dissolved in a ethyl acetate and ethanol, and the solvents were distilled off whereupon crystals were precipitated. These crystals were collected by filtration in a yield of 13.8 g. Further, the mother liquor was condensed to approximately 100 ml, and was poured into 1 liter of hexane, with stirring. The precipitated powder was collected by filtration and purified by silica gel column chromatography to yield 12.5 g of the title compound (total yield 82.5%).

Ultraviolet Absorption Spectrum (H$_2$O) $\lambda_{max}$ nm ($\epsilon$):
229.5 (19300), 256.5 (17400).

Nuclear Magnetic Resonance Spectrum (hexadeuterated dimethyl sulfoxide) $\delta$ ppm:
4.65 (1H, singlet);
5.25 (1H, doublet, J=3.0 Hz);
5.86 (1H, doublet, J=6.0 Hz);
6.40 (1H, doublet of doublets, J=3.0 & 6.0 Hz);
7.02 (1H, singlet);
8.30 (1H, singlet);
8.41 (1H, singlet).

EXAMPLE 90

Dimethyl $O^{2'}$-benzoyl-$O^{7'}$-(tetrahydropyran-2-yl)griseolate (Compound No. 246)

25.6 g of dimethyl $O^{2'}$-benzoylgriseolate (prepared as described in Example 89) were suspended in 250 ml of dioxane, and 10.5 g of p-toluenesulfonic acid were added to the suspension, to yield a clear yellow solution. 137 ml of 2,3-dihydropyran were added to this clear solution, and the mixture was stirred for 2.5 hours at room temperature. 4.2 g of anhydrous potassium carbonate were then added to the reaction mixture, and the solvent was distilled off. The residue was dissolved in a mixture of ethyl acetate with a saturated aqueous solution of sodium bicarbonate. The organic layer was separated, washed with water and dried over anhydrous magnesium sulfate. The drying agent was removed by filtration, after which the solvent was distilled off. Hexane was added to the residue, and the supernatant was removed. The remaining solution was purified by silica gel column chromatography, to yield 26.1 g (87.6%) of the title compound.

Ultraviolet Absorption Spectrum (H$_2$O) $\lambda_{max}$ nm ($\epsilon$):
230 (18100), 257 (17000).

Nuclear Magnetic Resonance Spectrum (hexadeuterated dimethyl sulfoxide) $\delta$ ppm:
4.54 & 4.81 (1H, singlet);
5.19 & 5.36 (1H, doublet, J=3.0 Hz);
5.84 (1H, doublet, J=6.0 Hz);
6.41 (1H, doublet of doublets, J=3.0 & 6.0 Hz);
7.07 (1H, singlet);
8.28 (1H, singlet);
8.40 (1H, singlet).

EXAMPLE 91

Dimethyl $O^{7'}$-(tetrahydropyran-2-yl)griseolate (Compound No. 101)

20 g of dimethyl $O^{2'}$-benzoyl-$O^{7'}$-(tetrahydropyran-2-yl)griseolate (prepared as described in Example 90) were dissolved in 150 ml of anhydrous methanol, and 16.8 ml of 1N sodium methoxide in methanol were added, with ice-cooling. The mixture was stirred for 2 hours. Acetic acid was then added to the reaction mixture and the pH of the mixture was adjusted to a value of about 8. The solvent was then distilled off. Ethyl acetate and water were added to the residue, and the organic layer was separated, washed with water and then dried over anhydrous magnesium sulfate. The drying agent was then removed by filtration and the solvent was distilled from the filtrate, which was then purified by silica gel column chromatography, to yield 16.3 g (98.6%) of the title compound.

Ultraviolet Absorption Spectrum (H$_2$O) $\lambda_{max}$ nm ($\epsilon$):
257 (16000).

Nuclear Magnetic Resonance Spectrum (hexadeuterated dimethyl sulfoxide) $\delta$ ppm:
4.65 (1H, doublet, J=6.0 Hz);
4.81 (1H, singlet);
5.17 (1H, doublet, J=3.0 Hz);
6.17 (1H, doublet of doublets, J=3.0 & 6.0 Hz);
6.59 (1H, singlet);
8.28 (1H, singlet);
8.41 (1H, singlet).

EXAMPLE 92

Dimethyl $O^{7'}$-(tetrahydropyran-2-yl)-$O^{2'}$-trifluoromethanesulfonylgriseolate (Compound No. 105)

16.3 g of dimethyl $O^{7'}$-(tetrahydropyran-2-yl)griseolate (prepared as described in Example 91) and 8.1 g of 4-(dimethylamino)pyridine were dissolved in 300 ml of dry methylene chloride. 7.04 ml of trifluoromethanesulfonyl chloride were then added under a stream of nitrogen gas and with cooling by dry ice/acetone. The mixture was stirred for 3 hours, with ice-cooling. Ice-water was added to the reaction mixture, and the organic layer was separated and washed firstly with ice-water, secondly with a saturated aqueous solution of sodium bicarbonate and finally with a saturated aqueous solution of sodium chloride. It was then dried over anhydrous magnesium sulfate, and then the drying agent was removed by filtration. The solvent was then distilled off and the residue was purified by silica gel column chromatography, to yield 14.8 g (71.6%) of the title compound.

Ultraviolet Absorption Spectrum (H$_2$O) $\lambda_{max}$ nm ($\epsilon$):
257 (16200).

Nuclear Magnetic Resonance Spectrum (hexadeuterated dimethyl sulfoxide) $\delta$ ppm:
4.15 (1H, singlet);
5.29 & 5.50 (1H, doublet, J=3.0 Hz);
6.05 (1H, doublet, J=6.0 Hz);
6.45 (1H, doublet of doublets, J=3.0 & 6.0 Hz);
7.36 (1H, singlet);

8.28 (1H, singlet);
8.40 (1H, singlet).

EXAMPLE 93

Dibenzhydryl $O^{7'}$-(tetrahydropyran-2-yl)griseolate (Compound No. 102)

17.5 ml of methanol and 175 ml of a 1N aqueous solution of sodium hydroxide were added to 26.1 g of dimethyl $O^{2'}$-benzoyl-$O^{7'}$-(tetrahydropyran-2-yl)griseolate (prepared as described in Example 90), and the mixture was reacted for about 20 hours, whilst stirring at room temperature. The solvent was then distilled off at a temperature below 30° C., and the residue was dissolved in 500–700 ml of acetone and 100–150 ml of water. Three equivalents of diphenyldiazomethane were added to this solution, whilst protecting it from light. The pH of the mixture was adjusted to a value of 1.5 with 3N hydrochloric acid and stirring was continued (the pH gradually rose to 3). After 2.5–4 hours, a 20% w/v aqueous solution of sodium bicarbonate was added to the reaction mixture, and its pH was adjusted to a value of 8–9. The solvent was then distilled from the mixture. The residue was dissolved in a mixture of ethyl acetate and water. The organic layer was separated, washed with water and dried over anhydrous magnesium sulfate. The drying agent was removed by filtration and the residue was purified by silica gel chromatography, to yield 16.0 g (46%) of the title compound.

Ultraviolet Absorption Spectrum (H$_2$O) $\lambda_{max}$ nm ($\epsilon$):
257 (17000).

Nuclear Magnetic Resonance Spectrum (hexadeuterated dimethyl sulfoxide) $\delta$ ppm:
4.67 (1H, doublet, J=6.0 Hz);
4.83 & 5.00 (1H, singlet);
5.20 & 5.30 (1H, doublet, J=3.0 Hz);
6.3–6.5 (1H, broad multiplet);
6.55 (1H, singlet);
8.17 (1H, singlet);
8.36 (1H, singlet).

EXAMPLE 94

Dibenzhydryl $O^{7'}$-(tetrahydropyran-2-yl)-$O^{2'}$-trifluoromethanesulfonylgriseolate (Compound No. 106)

12.8 g of dibenzhydryl $O^{7'}$-(tetrahydropyran-2-yl)griseolate (prepared as described in Example 93) and 5.9 g of 4-(dimethylamino)pyridine were dissolved in 300 ml of dry methylene chloride. 5.17 ml of trifluoromethanesulfonyl chloride were added, under a stream of nitrogen gas and whilst cooling with dry ice/acetone, to the solution. The mixture was then stirred at room temperature for 2–2.5 hours, after which ice-water was added to the reaction mixture. The organic layer was separated and washed firstly with a saturated aqueous solution of sodium bicarbonate and then with a saturated aqueous solution of sodium chloride and dried over anhydrous magnesium sulfate. The drying agent was removed by filtration and the solvent was distilled off. The residue was purified by silica gel column chromatography and then lyophilized from benzene, to yield 10.54 g (71.5%) of the title compound.

Ultraviolet Absorption Spectrum (H$_2$O) $\lambda_{max}$ nm ($\epsilon$):
257.5 (17300).

Nuclear Magnetic Resonance Spectrum (hexadeuterated dimethyl sulfoxide) $\delta$ ppm:
4.90 (1H, singlet);
5.29 & 5.53 (1H, doublet, J=3.0 Hz);
6.10 (1H, doublet, J=6.0 Hz);
6.7–6.9 (overlapping with benzhydryl H);
7.1–7.8 (overlapping with benzene);
8.13 (1H, singlet);
8.40 (1H, singlet).

EXAMPLE 95

2'(S)-Chloro-2'-deoxygriseolic acid (Compound No. 142)

2 g of dimethyl $O^{7'}$-(tetrahydropyran-2-yl)-$O^{2'}$-trifluoromethanesulfonylgriseolate (prepared as described in Example 92) were added to 20 ml of dimethylformamide, followed by 1.4 g of anhydrous lithium chloride, and the mixture was stirred at 60° C. (with heating) for 4 hours. The solvent was then distilled off, and the residue was dissolved in a mixture of ethyl acetate and water. The pH of the resulting solution was adjusted to a value of 4.5–6, and then the solution was extracted with ethyl acetate. The extract was dried over anhydrous magnesium sulfate and the drying agent was removed by filtration. The solvent was distilled from the residue, to yield dimethyl 2'(S)-chloro-2'-deoxy-$O^{7'}$-(tetrahydropyran-2-yl)griseolate.

This compound, in the form of a caramel-like substance, was dissolved in an 80% v/v aqueous solution of acetic acid, and the solution was refluxed for 1 hour. The solvent was then distilled from the reaction product, to yield dimethyl 2'(S)-chloro-2'-deoxygriseolate, which was then dissolved in a 1N aqueous solution of sodium hydroxide. The solution was stirred for 4 hours at room temperature. The pH of the reaction product was then adjusted to a value of 2 with concentrated hydrochloric acid, the solution was purified by chromatography through an Rp-8 prepacked column (Merck), eluted with a 5% v/v aqueous solution of acetonitrile containing 0.02% v/v acetic acid, to yield 0.18 g (14.2%) of the title compound.

Ultraviolet Absorption Spectrum (methanol) $\lambda_{max}$ nm ($\epsilon$):
257 (15000).

Nuclear Magnetic Resonance Spectrum (hexadeuterated dimethyl sulfoxide) $\delta$ ppm:
4.54 (1H, singlet);
5.21 (1H, triplet, J=8.3 Hz);
5.22 (1H, doublet, J=3.0 Hz);
6.25 (1H, doublet of doublets, J=3.0 & 9.6 Hz);
7.14 (1H, doublet, J=8.3 Hz);
8.22 (1H, singlet);
8.36 (1H, singlet).

EXAMPLE 96

2'(S)-Bromo-2'-deoxygriseolic acid (Compound No. 143)

The procedures described in Example 95 were repeated, except that anhydrous lithium bromide was used in place of the chloride, and the reagents were heated at 60° C. for only 30–50 minutes, to yield the title compound.

Ultraviolet Absorption Spectrum (methanol) $\lambda_{max}$ nm ($\epsilon$):
257.5 (15400).

Nuclear Magnetic Resonance Spectrum (hexadeuterated dimethyl sulfoxide) $\delta$ ppm:
4.52 (1H, singlet);
5.17 (1H, triplet, J=8.3 Hz);
5.21 (1H, doublet, J=3.0 Hz);

6.30 (1H, doublet of doublets, J=3.0 & 9.6 Hz);
7.39 (1H, doublet, J=8.3 Hz);
8.23 (1H, singlet);
8.36 (1H, singlet).

EXAMPLE 97

2'-Deoxygriseolic acid (Compound No. 144)

2.5 g of dibenzhydryl $O^{7'}$-(tetrahydropyran-2-yl)-$O^{2'}$-trifluoromethanesulfonylgriseolate (prepared as described in Example 94) were dissolved in 12 ml of hexamethylphosphoric triamide, and then anhydrous lithium bromide was added. The mixture was reacted for 4-5 hours on an ultrasonic washer (up to 35° C.). The reaction product was then stirred overnight at room temperature. It was then slowly poured into ice-water containing sodium chloride. The precipitate was collected by filtration and washed with ice-water and then with hexane. It was then dissolved in ethyl acetate and the solution was dried over anhydrous magnesium sulfate. The drying agent was filtered off and the filtrate was lyophilized from benzene to yield dibenzhydryl 2'-bromo-2'-deoxy-$O^{7'}$-(tetrahydropyran-2-yl)griseolate, which was then dissolved in 5 ml of methylene chloride. 15-20 ml of ethanol and 0.73 g of pyridine p-toluenesulfonate were added to this solution, and the mixture was allowed to react at 60° C. for 10-12 hours. The solvent was then filtered off from the mixture, and the residue was dissolved in methylene chloride. The solution was washed with water and dried over anhydrous magnesium sulfate. The drying agent was removed by filtration, and the solvent was distilled off. The residue was purified by silica gel column chromatography, to yield 0.9 g of dibenzhydryl 2'-bromo-2'-deoxygriseolate.

0.83 g of this compound and about 10 mg of azobisisobutyronitrile were dissolved in 20 ml of benzene, and then 0.7 ml of tributyltin hydride was added under a stream of nitrogen gas. The mixture was then refluxed for 45 minutes. The solvent was then distilled from the reaction product, and the residue was purified by silica gel column chromatography to yield 0.72 g of dibenzhydryl 2'-deoxygriseolate.

This compound was dissolved in 5 ml of anisole, and then 5 ml of trifluoroacetic acid were added, with ice-cooling. The mixture was left standing for 15 minutes, after which dry toluene was added and the solvent was distilled off. Acetone and toluene were added to the residue and were then distilled off. This process was repeated again, after which the residue was suspended in a small quantity of acetone. Hexane was added to the suspension to turn the solid matter into powder. This powder was collected by filtration, and dissolved in a saturated aqueous solution of sodium bicarbonate. The pH of the solution was adjusted to a value of 2.3 with 3N hydrochloric acid, and the solution was purified by chromatography through an Rp-8 prepacked column (Merck), to yield 0.237 g of the title compound on elution with a 3% v/v aqueous solution of acetonitrile containing 0.02% v/v acetic acid.

Ultraviolet Absorption Spectrum (methanol) $\lambda_{max}$ nm ($\epsilon$):
257.5 (15800).

Nuclear Magnetic Resonance Spectrum (hexadeuterated dimethyl sulfoxide) δ ppm:
2.76 (1H, broad multiplet);
4.50 (1H, singlet);
4.94 (1H, doublet, J=3.0 Hz);
6.05 (1H, broad multiplet);
6.90 (1H, broad multiplet);
8.24 (1H, singlet);
8.40 (1H, singlet).

EXAMPLE 98

2'(S)-Azido-2'-deoxygriseolic acid (Compound No. 247)

2 g of dibenzhydryl $O^{7'}$-(tetrahydropyran-2-yl)-$O^{2'}$-trifluoromethanesulfonylgriseolate (prepared as described in Example 94) were dissolved in 8 ml of hexamethylphosphoric triamide. 0.28 g of sodium azide was added to the solution, and the mixture was stirred for 3 hours at room temperature. The reaction product was poured into ice-water containing sodium chloride. The precipitate was collected by filtration and washed with water, and then dissolved in ethyl acetate and dried over anhydrous magnesium sulfate. The solvent was distilled off and the residue was purified by silica gel chromatography to yield 0.86 g of dibenzhydryl 2'(S)-azido-2'-deoxy-$O^{7'}$-(tetrahydropyran-2-yl)griseolate.

0.86 g of this compound and 0.13 g of pyridine p-toluenesulfonate were dissolved in 1 ml of methylene chloride and 5 ml of ethanol, and the mixture was heated at 50° C. for 12 hours. A further 0.13 g of pyridine p-toluenesulfonate was then added, and the mixture was reacted for a further 17 hours at 60° C. The solvent was distilled off, and the residue was dissolved in methylene chloride. The resulting solution was washed with water and dried over anhydrous magnesium sulfate. The solvent was distilled from the reaction product, and the residue was purified by silica gel chromatography to yield 0.36 g of dibenzhydryl 2'(S)-azido-2'-deoxygriseolate.

0.36 g of this compound was dissolved in 3ml of anisole, and then 3 ml of trifluoroacetic acid was added, with ice-cooling. The mixture was left standing for 15 minutes, after which dry toluene was added, and the solvent was distilled from the mixture. Acetone-toluene was added and the solvent was distilled off. This process was prepared twice. The residue was dissolved in a small quantity of acetone, to which hexane was added to turn the solid matter into powder. This powder was collected by filtration, and was dissolved in a saturated aqueous solution of sodium bicarbonate. The pH of this solution was adjusted to a value of 2.4, and then the solution was purified by chromatography through an Rp-8 prepacked column (Merck) eluted with a 5% v/v aqueous solution of acetonitrile containing 0.02% v/v acetic acid, to yield 0.14 g of the title compound.

Ultraviolet Absorption Spectrum (methanol) $\lambda_{max}$ nm ($\epsilon$):
257 (15800).

Nuclear Magnetic Resonance Spectrum (hexadeuterated dimethyl sulfoxide) δppm:
4.51 (1H, singlet);
5.01 (1H, triplet, J=8.3 Hz);
5.13 (1H, doublet, J=3.0 Hz);
6.08 (1H, doublet of doublets, J=3.0 & 9.6 Hz);
7.06 (1H, doublet, J=8.3 Hz);
8.20 (1H, singlet);
8.29 (1H, singlet).

EXAMPLE 99

2'(S)-Amino-2'-deoxygriseolic acid (Compound No. 248)

1.5 ml of water and 6 ml of pyridine were added to 0.1 g of 2'(S)-azido-2'-deoxygriseolic acid (prepared as described in Example 98). The air in the flask was replaced by nitrogen gas, and then the solution was saturated with hydrogen sulfide at room temperature. The container was tightly stoppered and left standing at room temperature for 7–8 hours and then left standing at 5° C. overnight. The solvent was distilled off, and water was added to the residue and then distilled off. This process was repeated and the residue was dissolved in 0.1N hydrochloric acid. The insoluble matter was removed by filtration and the pH of the filtrate was adjusted to a value of 2.3 with a saturated aqueous solution of sodium bicarbonate. The solution was then purified by chromatography through an Rp-8 prepacked column (Merck) eluted with a 3% v/v aqueous solution of acetonitrile containing 0.02% v/v acetic acid, to yield 93 mg of the title compound.

Ultraviolet Absorption Spectrum (methanol) $\lambda_{max}$ nm ($\epsilon$):
  256.5 (15600).

Nuclear Magnetic Resonance Spectrum (hexadeuterated dimethyl sulfoxide) $\delta$ppm:
  3.7–4.44 (overlapping with $H_2O$);
  4.44 (1H, singlet);
  4.95 (1H, doublet, J=3.0 Hz);
  5.86 (1H, broad multiplet);
  6.76 (1H, broad doublet);
  8.20 (1H, singlet);
  8.24 (1H, singlet).

EXAMPLE 100

2'-Deoxy-2'(S)-iodogriseolic acid (Compound No. 249)

1.37 g of dibenzhydryl $O^{7'}$-(tetrahydropyran-2-yl)-$O^{2'}$-trifluoromethanesulfonylgriseolate (prepared as described in Example 94) was dissolved in 4 ml of hexamethylphosphoric triamide, and then 0.8 g of anhydrous lithium iodide was added. The mixture was left standing for 5–6 hours at room temperature. A further 1 ml of hexamethylphosphoric triamide was added to the reaction mixture and was allowed to react for 6–7 hours on an ultrasonic washer (up to 40° C.). The reaction product was then poured into ice-water. The precipitate was collected by filtration, washed with water, dissolved in ethyl acetate, and dried over anhydrous magnesium sulfate. The solvent was distilled off and the residue was purified by silica gel chromatography, to yield 0.5 g of dibenzhydryl 2'-deoxy-2'(S)-iodo-$O^{7'}$-(tetrahydropyran-2-yl)griseolate.

A 0.5 g portion of this compound was dissolved in 1 ml of methylene chloride, and 0.14 g of pyridine p-toluenesulfonate and 10 ml of ethanol were added to the solution. The mixture was heated at 60° C. for 8 hours. The solvent was distilled from the reaction mixture, and the residue was dissolved in a mixture of ethyl acetate and water. The organic layer was separated, and dried over anhydrous magnesium sulfate. The solvent was then distilled from the reaction product, and the residue was purified by silica gel chromatography, to yield 0.35 g of dibenzhydryl 2'-deoxy-2'(S)-iodogriseolate.

A 0.32 g portion of this compound was dissolved in 3 ml of anisole, to which 3 ml of trifluoroacetic acid were then added, with ice-cooling. The mixture was left standing for 30 minutes. Dry toluene was then added, and the solvent was distilled from the reaction product. Acetone and toluene were added to the residue and then distilled off. This process was repeated twice. The residue was suspended in a small quantity of acetone, to which hexane was added. The resulting precipitate was collected by filtration. This precipitate was dissolved in a saturated aqueous solution of sodium bicarbonate and the insoluble matter was removed. The pH of the residue was adjusted to a value of 2.4 with 3N hydrochloric acid, and the precipitate was collected by filtration, washed with water and dried, to yield 160 mg of the title compound. The mother liquor was purified by chromatography through an Rp-8 prepacked column, (Merck), eluted with a 5% v/v aqueous solution of acetonitrile containing 0.02% v/v acetic acid, and the fraction containing the title compound was lyophilized to yield a further 0.01 g of the title compound.

Ultraviolet Absorption Spectrum (methanol) $\lambda_{max}$ nm ($\epsilon$):
  258 (15900).

Nuclear Magnetic Resonance Spectrum (hexadeuterated dimethyl sulfoxide) $\delta$ppm:
  4.52 (1H, singlet);
  5.00 (1H, triplet, J=8.3 Hz);
  5.18 (1H, doublet, J=3.0 Hz);
  6.29 (1H, doublet of doublets, J=3.0 & 9.6 Hz);
  6.96 (1H, doublet, J=8.3 Hz);
  8.22 (1H, singlet);
  8.34 (1H, singlet).

EXAMPLE 101

Dimethyl 4'β-acetoxy-$O^{2'}$,$O^{7'}$-diacetyl-5'-hydrogriseolate (Compound No. 170)

2.45 g of dimethyl $O^{2'}$,$O^{7'}$-diacetylgriseolate (prepared as described in Example 11) were suspended in anhydrous acetic acid containing 5% w/v hydrobromic acid. The mixture was heated, with stirring, at 50° C. for 20 minutes, whilst protecting it from moisture. The solvent was then distilled off. Acetone and toluene were added to the residue and then distilled off; this was done three times. The residue was dissolved in a mixture of 50 ml of ethyl acetate and 30 ml of an aqueous solution of sodium bicarbonate.

The organic phase was separated and washed, in turn, with 30 ml of a 5% w/v aqueous solution of sodium bicarbonate, 30 ml of water and 30 ml of a saturated aqueous solution of sodium chloride. It was then dried over anhydrous magnesium sulphate and the solvent was distilled off under reduced pressure. The caramel-like residue was purified by silica gel column chromatography, eluted with a mixture of 3% v/v aqueous methanol and methylene chloride. The ultraviolet absorption spectra of the resulting fractions were monitored and there were obtained, from the first fractions, 210 mg of the title compound.

Ultraviolet Absorption Spectrum (methanol) $\lambda_{max}$ nm ($\epsilon$):
  259 (16600).

Nuclear Magnetic Resonance Spectrum (hexadeuterated dimethyl sulfoxide) $\delta$ppm:
  2.83 (1H, doublet, J=15.0 Hz);
  3.20 (1H, doublet, J=15.0 Hz);
  5.07 (1H, doublet, J=4.2 Hz);
  5.62 (1H, singlet);
  6.18 (1H, quartet, J=4.2 & 6.6 Hz);

5.62 (1H, doublet, J=6.6 Hz);
8.29 (1H, singlet);
8.46 (1H, singlet).

EXAMPLE 102

Dimethyl O$^{2'}$,O$^{7'}$-diacetyl-4'$\beta$-bromo-5'-hydrogriseolate (Compound No. 171)

From the fractions following the ones collected in Example 101, there were obtained 1.06 g of the title compound.

Ultraviolet Absorption Spectrum (methanol) $\lambda_{max}$ nm ($\epsilon$):
258 (15300).

Nuclear Magnetic Resonance Spectrum (hexadeuterated dimethyl sulfoxide) $\delta$ppm:
2.98 (1H, doublet, J=15.0 Hz);
3.45 (1H, doublet, J=15.0 Hz);
5.38 (1H, doublet, J=3.9 Hz);
5.57 (1H, singlet);
6.40 (1H, quartet, J=3.9 & 6.0 Hz);
6.58 (1H, doublet, J=6.0 Hz);
8.27 (1H, singlet);
8.51 (1H, singlet).

EXAMPLE 103

Dimethyl O$^{2'}$,O$^{7'}$-diacetyl-4'$\beta$,5'-dihydrogriseolate (Compound No. 172)

572 mg of dimethyl O$^{2'}$,O$^{7'}$-diacetyl-4'$\beta$-bromo-5'-hydrogriseolate (prepared as described in Example 102) were dissolved in 10 ml of acetone. 10 ml of 80% v/v aqueous acetic acid and 690 mg of zinc powder were added, and the mixture was stirred at room temperature for 4 hours and 20 minutes. At the end of this time, the solvent was distilled off and the residue was dissolved in a mixture of 10 ml of water and 20 ml of ethyl acetate. The solution was adjusted to a pH value of 1 by the addition of 1N hydrochloric acid, and the impurities were filtered off. The organic phase was washed, in turn, with 20 ml of a saturated aqueous solution of sodium chloride and 20 ml of a 5% aqueous solution of sodium bicarbonate, and dried over anhydrous magnesium sulphate. The solvent was distilled off under reduced pressure, and the residue was purified by chromatography through an Rp-8 prepacked silica gel column (Merck), eluted with a mixture of 3% v/v aqueous methanol and methylene chloride, to give 129 mg of the title compound in the form of a colorless caramel-like substance.

Ultraviolet Absorption Spectrum (methanol) $\lambda_{max}$ nm ($\epsilon$):
258 (13700).

Nuclear Magnetic Resonance Spectrum (hexadeuterated dimethyl sulfoxide) $\delta$ppm:
3.4–3.6 (multiplet);
5.00 (1H, multiplet);
5.63 (1H, singlet);
5.97 (1H, quartet, J=3.3 & 6.6 Hz);
6.40 (1H, doublet, J=6.6 Hz);
8.23 (1H, singlet);
8.53 (1H, singlet).

EXAMPLE 104

4'$\beta$,5'-Dihydrogriseolic acid (Compound No. 173)

80 mg of dimethyl O$^{2'}$,O$^{7'}$-diacetyl-4'$\beta$,5'-dihydrogriseolate (prepared as described in Example 103) were added to a 0.2N aqueous solution of sodium hydroxide, and the mixture was made into a solution by ultrasonic vibration for about 10 minutes. The solution was allowed to stand for 2 hours and then its pH was adjusted to a value of 2.3 by the addition of 1N hydrochloric acid. The reaction mixture was then purified by chromatography through an Rp-8 prepacked column (Merck), eluted with 10% v/v aqueous acetonitrile, to give 57 mg of the title compound in the form of a white powder.

Ultraviolet Absorption Spectrum (H$_2$O) $\lambda_{max}$ nm ($\epsilon$):
258 (13600).

Nuclear Magnetic Resonance Spectrum (hexadeuterated dimethyl sulfoxide) $\delta$ppm:
4.40 (1H, singlet);
4.6–5.2 (3H, multiplet);
6.83 (1H, doublet, J=6.9 Hz);
8.22 (1H, singlet);
8.37 (1H, singlet).

EXAMPLE 105

Dimethyl 4'$\beta$-acetoxy-O$^{2'}$,O$^{7'}$-diacetyl-6-desamino-5'-hydro-6-hydroxygriseolate (Compound No. 174)

(i) 4 g of dimethyl O$^{2'}$,O$^{7'}$-diacetyl-6-desamino-6-hydroxygriseolate (prepared as described in Example 50) were placed in a two-necked flask fitted with a cooler, and the flask was then purged with nitrogen gas. 40 ml of 4% w/v hydrogen chloride in ethyl acetate were added and the mixture was heated at 80° C. for 2 hours. At the end of this time, the solvent was distilled off under reduced pressure. The residue was dissolved in a mixture of toluene and methylene chloride and distillation was effected three times, adding toluene and methylene chloride prior to each distillation. The residue was extracted with methylene chloride and then washed three times with a saturated aqueous solution of sodium bicarbonate. The extract was dried over anhydrous magnesium sulphate, and then evaporated to dryness under reduced pressure. The residue was purified by silica gel column chromatography, eluted with 1% v/v methanol in methylene chloride, affording 270 mg of the title compound.

(ii) 600 mg of dimethyl O$^{2'}$,O$^{7'}$-diacetyl-6-desamino-6-hydroxygriseolate (prepared as described in Example 50) were subjected to Parr catalytic reduction at room temperature and at 50 psig (3.4 bars) for 6 hours, using 70 ml of acetic acid and 600 mg of platinum oxide. At the end of this time, the reaction vessel was purged with nitrogen gas and the reaction mixture was filtered. Water was added to the reaction mixture, which was then extracted three times with methylene chloride. The extracts were collected, dried over anhydrous magnesium sulphate and evaporated to dryness under reduced pressure. The residue was purified by silica gel column chromatography, eluted with 3% v/v methanol in methylene chloride, to give 28 mg of the title compound.

(iii) 500 mg of dimethyl O$^{2'}$,O$^{7'}$-diacetyl-6-desamino-6-hydroxygriseolate (prepared as described in Example 50) were placed in a two-necked flask, which was then purged with nitrogen gas. 100 ml of a 4:1 by volume mixture of acetic acid and acetic anhydride were added to prepare a solution, and then 2 ml of trifluoromethanesulfonic acid were added, whilst ice-cooling. The mixture was stirred at room temperature for 2 days and, at the end of this period, 20 g of sodium acetate were added and the mixture was evaporated to dryness. 100 ml of methylene chloride were added to the residue and the solution was washed with a saturated aqueous solution of sodium bicarbonate. The aqueous phase was extracted with 100 ml of methylene chloride and the organic phase was combined with the extract and dried over anhydrous magnesium sulphate. The solvent was then distilled off under reduced pressure. The residue was subjected to silica gel column chromatography. Elution with methylene chloride gave a sugar derivative formed by cleavage of the griseolic acid skeleton. After this, elution was continued using 1% v/v methanol in methylene chloride, and then 5% v/v methanol in methylene chloride, to give 129 mg of the title compound.

Ultraviolet Absorption Spectrum (50% v/v aqueous methanol) $\lambda_{max}$ nm ($\epsilon$):
248.5 (10200).

Nuclear Magnetic Resonance Spectrum (CDCl$_3$) $\delta$ppm:
2.82 (1H, doublet, J=16.5 Hz);
3.34 (1H, doublet, J=16.5 Hz);
5.17 (1H, doublet, J=4.3 Hz);
5.87 (1H, singlet);
6.08 (1H, doublet of doublets, J=4.3 & 7.3 Hz);
6.64 (1H, doublet, J=7.3 Hz);
8.18 (1H, singlet);
8.40 (1H, singlet).

EXAMPLE 106

Dimethyl 4'α-acetoxy-$O^{2'}$,$O^{7'}$-diacetyl-6-desamino-5'-hydro-6-hydroxygriseolate (Compound No. 175)

The procedure described in Example 105 (iii) was repeated. The reaction mixture was purified by silica gel column chromatography, eluted first with 1% v/v methanol in methylene chloride, and then with 5% v/v methanol in methylene chloride, to give 64 mg of the title compound.

Ultraviolet Absorption Spectrum (50% v/v aqueous methanol) $\lambda_{max}$ nm ($\epsilon$):
248.5 (10200).

Nuclear Magnetic Resonance Spectrum (CDCl$_3$) $\delta$ ppm:
3.03 (1H, doublet, J=15.1 Hz);
3.50 (1H, doublet, J=15.1 Hz);
5.13 (1H, doublet of doublets);
5.67 (1H, doublet);
5.71 (1H, singlet);
6.72 (1H, doublet, J=5.4 Hz);
8.02 (1H, singlet);
8.61 (1H, singlet).

EXAMPLE 107

Dimethyl $O^{2'}$,$O^{7'}$-diacetyl-4'β-chloro-6-desamino-5'-hydro-6-hydroxygriseolate (Compound No. 176)

The procedure described in Example 105 (i) was repeated. The reaction mixture was purified by silica gel column chromatography, eluted with 4% v/v methanol in methylene chloride, to give 2.0 g of the title compound.

Ultraviolet Absorption Spectrum (50% v/v aqueous methanol) $\lambda_{max}$ nm ($\epsilon$):
248 (9500).

Nuclear Magnetic Resonance Spectrum (a 1:1 by volume mixture of D$_2$O and hexadeuterated dimethyl sulfoxide) $\delta$ ppm:
3.32 (1H, doublet, J=15.0 Hz);
3.75 (1H, doublet, J=15.0 Hz);
5.28 (1H, doublet, J=4.5 Hz);
6.00 (1H, singlet);
6.28 (1H, doublet of doublets, J=4.5 & 5.9 Hz);
6.55 (1H, doublet, J=5.9 Hz);
8.18 (1H, singlet);
8.47 (1H, singlet).

EXAMPLE 108

Dimethyl $O^{2'}$,$O^{7'}$-diacetyl-4'β-bromo-6-desamino-5'-hydro-6-hydroxygriseolate (Compound No. 177)

500 mg of dimethyl $O^{2'}$,$O^{7'}$-diacetyl-6-desamino-6-hydroxygriseolate (prepared as described in Example 50) were added to 10% w/v hydrobromic acid in acetic acid and the mixture was dissolved by ultrasonic vibration for 30 minutes.

The solution was allowed to stand for 64 hours at room temperature, and then the solvent was distilled off under reduced pressure. Distillation was effected three times, each time first adding to the residue acetone and toluene. 30 ml of ethyl acetate were added to the residue and the mixture was subjected to ultrasonic vibration. Insolubles were separated by filtration and dissolved in 30 ml of ethyl acetate and a 5% w/v aqueous solution of sodium bicarbonate. The organic phase was washed with 20 ml of a saturated aqueous solution of sodium chloride and dried over anhydrous magnesium sulphate. The solvent was distilled off under reduced pressure and the residue was purified by silica gel column chromatography and then lyophilised from benzene to give 60 mg of the title compound in the form of a white powder.

Ultraviolet Absorption Spectrum (methanol) $\lambda_{max}$ nm ($\epsilon$):
244 (14200), 249 shoulder (13800), 270 shoulder (6000).

Nuclear Magnetic Resonance Spectrum (hexadeuterated dimethyl sulfoxide) $\delta$ ppm:
2.98 (1H, doublet, J=15.6 Hz);
3.47 (1H, doublet, J=15.6 Hz);
5.35 (1H, doublet, J=4.2 Hz);
5.57 (1H, singlet);
6.32 (1H, quartet, J=4.2 & 6.6 Hz);
6.53 (1H, doublet, J=6.6 Hz);
8.17 (1H, singlet);
8.47 (1H, singlet).

EXAMPLE 109

Dimethyl $O^{2'}$,$O^{7'}$-diacetyl-6-desamino-4'β,5'-dihydro-6-hydroxygriseolate (Compound No. 178)

(i) 500 mg of dimethyl $O^{2'}$,$O^{7'}$-diacetyl-4'β-chloro-6-desamino-5'-hydro-6-hydroxygriseolate (prepared as described in Example 107), 10 mg of 2,2'-azobisisobutyronitrile, 20 ml of benzene and 3.1 ml of tributyltin hydride were added, in that order, to a reaction vessel, and the mixture was refluxed, with stirring, under a nitrogen atmosphere for 2 hours. The solvent was then distilled off and the residue was purified by silica gel column chromatography, eluted with 3% v/v methanol in methylene chloride, to give 350 mg of the title compound.

(ii) 600 mg of dimethyl $O^{2'}$,$O^{7'}$-diacetyl-6-desamino-6-hydroxygriseolate (prepared as described in Example 50) were subjected to Parr catalytic reduction at room temperature and at 50 psig for 6 hours, using 70 ml of acetic acid and 600 mg of platinum oxide. At the end of this period, the vessel was purged with nitrogen, and then the reaction mixture was filtered. Water was added to the filtrate, which was extracted three times, each time with 50 ml of methylene chloride. The organic phase was collected, dried over anhydrous magnesium sulfate, and the solvent was distilled off under reduced pressure. The residue was purified by silica gel column chromatography, eluted with 70% v/v benzene in acetone, to give 60 mg of the title compound.

Ultraviolet Absorption Spectrum (50% v/v aqueous methanol) $\lambda_{max}$ nm ($\epsilon$):
248.7 (10400).

Nuclear Magnetic Resonance Spectrum (a 1:1 by volume mixture of D$_2$O and CDCl$_3$) $\delta$ ppm:
2.4–2.7 (multiplet);
5.00 (1H, doublet, J=4.5 Hz);
5.62 (1H, singlet);
5.88 (1H, doublet of doublets, J=4.5 & 7.5 Hz);
6.48 (1H, doublet, J=7.5 Hz);
8.13 (1H, singlet);
8.48 (1H, singlet).

EXAMPLE 110

6-Desamino-4'α,5'-dihydro-6-hydroxygriseolic acid (Compound No. 179)

350 g of dimethyl O$^{2'}$,O$^{7'}$-diacetyl-6-desamino-5'-hydro-4'β,5'-hydroxygriseolate (prepared as described in Example 109) were dissolved, whilst ice-cooling, in 20 ml of 1N aqueous sodium hydroxide, and the solution was allowed to stand at room temperature for 2 hours. At the end of this time, the reaction mixture was adjusted to a pH value of 1 with hydrochloric acid, whilst ice-cooling. This mixture was subjected to Rp-18 reverse phase column chromatography, eluted with a mixture of 3% v/v acetonitrile, 0.3% v/v acetic acid and water. The eluate was lyophilized to give 140 mg of the title compound.

Ultraviolet Absorption Spectrum (H$_2$O) $\lambda_{max}$ nm ($\epsilon$): 248.5 (11800).

Nuclear Magnetic Resonance Spectrum (a 1:1 by volume mixture of D$_2$O and hexadeuterated dimethyl sulfoxide) $\delta$ ppm:
2.46 (1H, doublet of doublets, J=7.5 & 14.3 Hz);
2.58 (1H, doublet of doublets, J=2.3 & 14.3 Hz);
4.32 (1H, singlet);
4.63 (1H, doublet of doublets);
4.77 (1H, doublet of doublets);
6.00 (1H, doublet, J=7.8 Hz);
8.06 (1H, singlet);
8.28 (1H, singlet).

EXAMPLE 111

Dimethyl O$^{2'}$,O$^{7'}$-diacetyl-5'α-chloro-6-desamino-6-hydroxy-4'β-methoxygriseolate (Compound No. 180)

500 mg of dimethyl O$^{2'}$,O$^{7'}$-diacetyl-6-desamino-6-hydroxygriseolate (prepared as described in Example 50) were dissolved in anhydrous methanol and the solution was ice-cooled. 1 ml (about 1.56 mmole) of carbon tetrachloride containing 11.05% w/w of chlorine was added and the mixture was reacted, whilst ice-cooling, for 2 hours. At the end of this time, the remaining chlorine was decomposed by sodium hydrogen sulfite and the solvent was distilled off under reduced pressure. The residue was purified by silica gel column chromatography, eluted with a 1% v/v solution of methanol in methylene chloride, to give 412 mg of the title compound.

Ultraviolet Absorption Spectrum (50% v/v aqueous methanol) $\lambda_{max}$ nm ($\epsilon$):
248.5 (9300).

Nuclear Magnetic Resonance Spectrum (a 1:1 by volume mixture of D$_2$O and CDCl$_3$) $\delta$ ppm:
3.41 (1H, singlet);
4.72 (1H, doublet, J=6.3 Hz);
5.64 (1H, doublet of doublets, J=4.5 & 6.3 Hz);
5.88 (1H, singlet);
5.94 (1H, doublet, J=4.5 Hz);
8.05 (1H, singlet);
8.37 (1H, singlet).

EXAMPLE 112

Dimethyl O$^{2'}$,O$^{7'}$-diacetyl-5'α-bromo-6-desamino-6-hydroxy-4'β-methoxygriseolate (Compound No. 181)

300 mg of dimethyl O$^{2'}$,O$^{7'}$-diacetyl-6-desamino-6-hydroxygriseolate (prepared as described in Example 50) were dissolved in 30 ml of methanol and, whilst ice-cooling, 600 mg of N-bromosuccinimide were added. The mixture was stirred at room temperature for 10 minutes. At the end of this time, an aqueous solution of sodium hydrogen sulfite was added until the reaction mixture turned colorless. The solvent was distilled off under reduced pressure and the residue was extracted three times, each time with 30 ml of a saturated aqueous solution of sodium bicarbonate and 30 ml of methylene chloride. The organic phase was collected and dried over anhydrous magnesium sulfate, and the solvent was distilled off under reduced pressure. The residue was purified by silica gel column chromatography, eluted with a 3% v/v solution of methanol in methylene chloride, to give 130 mg of the title compound.

Ultraviolet Absorption Spectrum (50% v/v aqueous methanol) $\lambda_{max}$ nm ($\epsilon$):
248.5 (11600).

Nuclear Magnetic Resonance Spectrum (a 1:1 by volume mixture of D$_2$O and hexadeuterated dimethyl sulfoxide) $\delta$ ppm:
3.50 (1H, singlet);
5.20 (1H, doublet, J=9.9 Hz);
5.81 (1H, doublet of doublets, J=2.4 & 9.9 Hz);
5.90 (1H, singlet);
5.97 (1H, doublet, J=2.4 Hz);
8.01 (1H, singlet);
8.32 (1H, singlet).

EXAMPLE 113

4',7'-Anhydro-5'α-bromo-6-desamino-4'α,6-dihydroxygriseolic acid (Compound No. 182)

1.5 g of 6-desamino-6-hydroxygriseolic acid (prepared as described in Example 36) were dissolved in 2N aqueous sodium hydroxide and, whilst ice-cooling, 258 ml of a saturated aqueous solution of bromine were added.

The mixture was stirred at 0° C. for 40 minutes and, at the end of this time, the remaining bromine was decomposed by the addition of an aqueous solution of sodium hydrogen sulfite. The reaction mixture was adjusted to a neutral pH value with a saturated aqueous solution of sodium bicarbonate and then lyophilized. The residue was dissolved in water and the solution was adjusted to a pH value of 1 with 1N hydrochloric acid. The solution was subjected to reverse phase column chromatography through an Rp-8 column, eluted first with water to remove salts then with 5% v/v aqueous methanol. The eluate was lyophilized to give 2 g of the title compound.

Ultraviolet Absorption Spectrum (H$_2$O) $\lambda_{max}$ nm ($\epsilon$): 248.5 (10100).

Nuclear Magnetic Resonance Spectrum (a 1:1 by volume mixture of D$_2$O and hexadeuterated dimethyl sulfoxide) $\delta$ ppm:
 4.67 (1H, doublet, J=6.9 Hz);
 4.99 (1H, singlet);
 5.31 (1H, singlet);
 5.90 (1H, doublet, J=6.9 Hz);
 6.70 (1H, singlet);
 8.12 (1H, singlet);
 8.33 (1H, singlet).

EXAMPLE 114

4',7'-Anhydro-5'α-chloro-4'α-hydroxygriseolic acid (Compound No. 183)

50 mg of griseolic acid were dissolved in 2N aqueous sodium hydroxide and the solution was ice-cooled. 50 ml of a saturated aqueous solution of chlorine were added, whilst ice-cooling and stirring, over 3 hours. At the end of this time, the solvent was distilled off and the residue was adjusted to a neutral pH value with a saturated aqueous solution of sodium bicarbonate and then lyophylized. The residue was dissolved in water and the solution was adjusted to a pH value of 1 with 1N hydrochloric acid.

This solution was subjected to reverse phase column chromatography through an Rp-8 column, eluted with a mixture of 2% w/v acetonitrile, 0.3% w/v aqueous acetic acid and 97.7% water. The eluate was lyophilized to give 10 mg of the title compound.

Ultraviolet Absorption Spectrum (H$_2$O) $\lambda_{max}$ nm ($\epsilon$): 258 (14600).

Nuclear Magnetic Resonance Spectrum (a 1:1 by volume mixture of D$_2$O and hexadeuterated dimethyl sulfoxide) $\delta$ ppm:
 4.56 (1H, doublet, J=6.9 Hz);
 4.71 (1H, singlet);
 4.98 (1H, singlet);
 5.62 (1H, doublet, J=6.9 Hz);
 6.60 (1H, singlet);
 8.14 (1H, singlet);
 8.30 (1H, singlet).

EXAMPLE 115

4',7'-Anhydro-5'α-bromo-4'α-hydroxygriseolic acid (Compound No. 184)

2.27 g of griseolic acid were dissolved in 60 ml of 2N aqueous sodium hydroxide and, whilst ice-cooling, 112 ml of a saturated aqueous solution of bromine were added dropwise over a period of 5 minutes. The mixture was stirred for 30 minutes and, at the end of this time, the excess bromine was decomposed by the addition of 20 ml of a 5 molar aqueous solution of sodium hydrogen sulfite. The mixture was adjusted to a pH value of 2.3 with concentrated hydrochloric acid and allowed to stand overnight in a refrigerator. The crystals which precipitated were collected by filtration to give 1.6 g of the title compound in the form of yellow needles.

Ultraviolet Absorption Spectrum (H$_2$O) $\lambda_{max}$ nm ($\epsilon$): 257.5 (15500).

Nuclear Magnetic Resonance Spectrum (hexadeuterated dimethyl sulfoxide) $\delta$ ppm:
 4.73 (1H, doublet, J=6.6 Hz);
 4.93 (1H, singlet);
 5.27 (1H, singlet);
 5.98 (1H, doublet, J=6.6 Hz);
 6.72 (1H, singlet);
 8.21 (1H, singlet);
 8.39 (1H, singlet).

EXAMPLE 116

4',7'-Anhydro-4'α-hydroxy-5'α-iodogriseolic acid (Compound No. 185)

10 g of griseolic acid were dissolved in 264 ml of 2N aqueous sodium hydroxide and, whilst ice-cooling, a solution containing 0.5 mole of iodine in methanol was added dropwise. Crystals began to precipitate when about two thirds of the iodine solution had been added. After 3.5 hours, 700 ml of water, and then 27.5 g of sodium hydrogen sulfite, were added and the solution was adjusted to a pH value of 2.3 with a saturated aqueous solution of sodium bicarbonate. The reaction mixture was allowed to stand overnight at 5° C. The crystals which precipitated were collected by filtration, washed with water and then hexane, and then dried to give 13.0 g of the title compound.

Ultraviolet Absorption Spectrum (H$_2$O) $\lambda_{max}$ nm ($\epsilon$): 258 (12300).

Nuclear Magnetic Resonance Spectrum (hexadeuterated dimethyl sulfoxide) $\delta$ ppm:
 4.77 (1H, doublet, J=6.9 Hz);
 4.96 (1H, singlet);
 5.11 (1H, singlet);
 6.07 (1H, doublet, J=6.9 Hz);
 6.73 (1H, singlet);
 8.23 (1H, singlet);
 8.40 (1H, singlet).

EXAMPLE 117

4',7'-Anhydro-5'α,8-dibromo-4'α-hydroxygriseolic acid (Compound No. 187)

2.85 g of 4',7'-anhydro-5'α-bromo-4'α-hydroxygriseolic acid (prepared as described in Example 115) were dissolved, with heating, in 150 ml of 1 molar acetate buffer solution (pH 4.0). The solution was cooled to room temperature and 120 ml of a saturated aqueous solution of bromine were added dropwise. The mixture was allowed to stand for 6 hours. At the end of this time, the disappearance of the starting compound was confirmed by thin layer chromatography. The excess bromine was decomposed by the addition of 2.67 g of sodium hydrogen sulfide, and the mixture was adjusted to a pH value of 2.3 by the addition of concentrated hydrochloric acid.

The solvent was distilled off and the residue was dissolved in the smallest possible amount of water. The solution was again adjusted to a pH value of 2.3 and allowed to stand overnight in a refrigerator. The resulting solid was collected by filtration and recrystallized from water to give 2.2 g of the title compound.

Ultraviolet Absorption Spectrum (H$_2$O) $\lambda_{max}$ nm ($\epsilon$): 264 (15300).

Nuclear Magnetic Resonance Spectrum (hexadeuterated dimethyl sulfoxide) $\delta$ppm:
 4.99 (1H, singlet);
 5.03 (1H, doublet, J=6.9 Hz);
 5.32 (1H, singlet);

6.15 (1H, doublet, J=6.9 Hz); 6.49 (1H, singlet);
8.20 (1H, singlet).

EXAMPLE 118

4',7'-Anhydro-8-bromo-4'α-hydroxy-5'α-iodogriseolic acid (Compound No. 188)

4.04 g of 4',7'-anhydro-4'α-hydroxy-5'α-iodogriseolic acid (prepared as described in Example 116) were suspended in 48.6 ml of a 1 molar acetate buffer solution (pH 4.0) and, whilst ice-cooling, 160 ml of a saturated aqueous solution of bromine were added. The reaction mixture was slowly adjusted to a pH value of 4.0 by the addition of a saturated aqueous solution of sodium bicarbonate and allowed to stand at room temperature for 17 hours. The solvent was distilled off under reduced pressure and distillation was repeated until the acetic odor had dissipated, each time adding ethanol. The resulting residue was dissolved in 50 ml of water, and the solution was adjusted to a pH value of 2.3 with 3N hydrochloric acid, whilst ice-cooling. The mixture was allowed to stand, with ice-cooling, for 3 hours, and the crystals, which separated were collected by filtration and dried to give 1.9 g of the title compound.

Ultraviolet Absorption Spectrum (H$_2$O) $\lambda_{max}$ nm ($\epsilon$): 265 (14100).

Nuclear Magnetic Resonance Spectrum (hexadeuterated dimethyl sulfoxide) δppm:
4.84 (1H, singlet);
4.96 (1H, doublet, J=6.9 Hz);
5.04 (1H, singlet);
6.15 (1H, doublet, J=6.9 Hz);
6.43 (1H, singlet);
8.18 (1H, singlet).

EXAMPLE 119

Dibenzhydryl 4',7'-anhydro-5'α,8-dibromo-4'α-hydroxygriseolate (Compound No. 189)

300 mg of 4',7'-anhydro-5'α,8-dibromo-4'α-hydroxygriseolic acid (prepared as described in Example 117) were dissolved in 6 ml of dimethylformamide, and then a solution of 419 mg of diphenyldiazomethane in 2 ml of ethanol was added.

The mixture was stirred at room temperature for 3 hours and, at the end of this time, the disappearance of the starting compound was confirmed by thin layer chromatography. The excess diphenyldiazomethane was decomposed by the addition of acetic acid. The solvent was distilled off under reduced pressure and the residue triturated with diethyl ether to give a powder.

This was collected by filtration and recrystallized from ethanol to give 380 mg of the title compound in the form of pale yellow crystals.

Ultraviolet Absorption Spectrum (methanol) $\lambda_{max}$ nm ($\epsilon$):
262 (15900).

Nuclear Magnetic Resonance Spectrum (hexadeuterated dimethyl sulfoxide) δppm:
5.05 (1H, doublet of doublets, J=6.9 & 11.4 Hz);
5.63 (1H, singlet);
5.83 (1H, singlet);
6.25 (1H, doublet, J=6.9 Hz);
6.53 (1H, singlet);
8.17 (1H, singlet).

EXAMPLE 120

Dibenzhydryl 4',7'-anhydro-5'α-bromo-4'α-hydroxy-8-mercaptogriseolate (Compound No. 190)

1.97 g of dibenzhydryl 4',7'-anhydro-5'α,8-dibromo-4'α-hydroxygriseolate (prepared as described in Example 119) were placed in a two-necked flask. 20 ml of pyridine were added under a stream of nitrogen. After the nitrogen gas had been charged for 5 minutes, hydrogen sulfide was introduced, whilst ice-cooling, for 30 minutes. The flask was then purged with nitrogen gas, plugged and allowed to stand at room temperature for 30 hours. At the end of this time, more nitrogen gas was introduced to the reaction mixture at room temperature for 1 hour to remove the excess hydrogen sulfide. The solvent was distilled off under reduced pressure, and distillation was repeated, each time adding ethanol to the residue. The residue was dissolved in 30 ml of ethyl acetate and 20 ml of water.

The organic phase was separated and washed, in turn, with 20 ml each of 0.1N hydrochloric acid, a 5% w/v aqueous solution of sodium bicarbonate and a saturated aqueous solution of sodium chloride. The mixture was then dried over anhydrous magnesium sulfate, and the solvent was distilled off under reduced pressure to give 1.69 g of a residue. This was purified through a silica gel prepacked column (Merck), eluted with a 2% v/v solution of methanol in methylene chloride. The eluate was lyophilized from benzene to give 1.20 g of the title compound.

Ultraviolet Absorption Spectrum (methanol) $\lambda_{max}$ nm ($\epsilon$):
301.5 (28100), 308.5 (29000).

Nuclear Magnetic Resonance Spectrum (hexadeuterated dimethyl sulfoxide) δ ppm:
4.80 (1H, doublet of doublets);
5.62 (1H, singlet);
5.80 (1H, singlet);
6.32 (1H, doublet, J=6.9 Hz);
8.15 (1H, singlet).

EXAMPLE 121

Dibenzhydryl 8-mercaptogriseolate (Compound No. 191)

1.69 g of dibenzhydryl 4',7'-anhydro-5'α-bromo-4'α-hydroxy-8-mercaptogriseolate (prepared as described in Example 120) were dissolved in 20 ml of acetone. 20 ml of 80% w/v aqueous acetic acid and 1.3 g of zinc powder were added and the mixture was vigorously shaken at room temperature. After 5 hours, a further 1.3 g of zinc powder was added and stirring was continued for 24 hours. At the end of this time, the solvent was distilled off and the residue was dissolved in 30 ml of ethyl acetate and 20 ml of 0.1N hydrochloric acid. Impurities were removed by filtration and the organic phase was washed, in turn, with 20 ml each of water, a 5% w/v aqueous solution of sodium bicarbonate and a saturated aqueous solution of sodium chloride.

This solution was dried over anhydrous magnesium sulfate and the solvent was distilled off. The residue was purified by silica gel column chromatography through an Rp-8 prepacked column, eluted with a 3% v/v solution of methanol in methylene chloride, to give 173 mg of the title compound.

Ultraviolet Absorption Spectrum (methanol) $\lambda_{max}$ nm ($\epsilon$):

302 (27500), 308.5 (28400).

Nuclear Magnetic Resonance Spectrum (hexadeuterated dimethyl sulfoxide) δ ppm:
 4.62 (1H, triplet, J=4.5 & 6.0 Hz);
 4.90 (1H, doublet, J=9.0 Hz);
 5.26 (1H, doublet, J=2.7 Hz);
 6.46 (1H, quartet, J=2.7 & 6.0 Hz);
 6.89 (1H, singlet);
 8.15 (1H, singlet).

EXAMPLE 122

8-Mercaptogriseolic acid (Compound No. 192)

130 mg of dibenzhydryl 8-mercaptogriseolate (prepared as described in Example 121) were suspended in 1 ml of anisole and, whilst ice-cooling, 1 ml of trifluoroacetic acid was added to form a solution. The solution was allowed to stand for 30 minutes, and then toluene was added and the solvent was distilled off. Distillation was repeated, each time adding acetone and toluene to the residue. The residue was dissolved in a small amount of acetone and the solution was poured, with stirring, into hexane to give a powder. This was dissolved in a saturated aqueous solution of sodium bicarbonate, and the solution was adjusted to a pH value of 2.3 with 1N hydrochloric acid. It was then purified by reverse phase column chromatography through an Rp-8 prepacked column and lyophilized to give 50 mg of the title compound.

Ultraviolet Absorption Spectrum ($H_2O$) $\lambda_{max}$ nm (ε): 298 (18200), 305 shoulder (17400).

Nuclear Magnetic Resonance Spectrum (hexadeuterated dimethyl sulfoxide) δ ppm:
 4.50 (1H, singlet);
 4.58 (1H, doublet, J=5.4 Hz);
 5.10 (1H, doublet, J=2.4 Hz);
 6.24 (1H, doublet of doublets, J=2.4 & 5.4 Hz);
 6.80 (1H, singlet);
 8.20 (1H, singlet).

EXAMPLE 123

Dibenzhydryl 4',7'-anhydro-5'α-bromo-4'α-hydroxy-8-methoxygriseolate (Compound No. 193)

999 mg of 4',7'-anhydro-5'α,8-dibromo-4'α-hydroxygriseolic acid (prepared as described in Example 117) were suspended in 36 ml of pyridine, and then 3.6 ml of a 2N solution of sodium methoxide in methanol were added. The mixture was allowed to react at room temperature for about 4 hours whilst being agitated by ultrasonic vibration.

The solvent was distilled off and the residue was dissolved in 1N hydrochloric acid and sodium bicarbonate was added, to give a solution of pH 1.5. The same volume of acetone was added, followed by diphenyldiazomethane, with stirring, until bubbling ceased. The excess diphenyldiazomethane was decomposed by the addition of acetic acid. The solvent was distilled off under reduced pressure and the residue was dissolved in 30 ml of ethyl acetate and 20 ml of water. The organic phase was washed, in turn, with 20 ml each of 0.1N hydrochloric acid, water, a 5% w/v aqueous solution of sodium bicarbonate and a saturated aqueous solution of sodium chloride. The organic phase was dried over anhydrous magnesium sulfate and the solvent was distilled off. The residue was purified by silica gel column chromatography through a prepacked column (Merck), eluted with a 3% v/v solution of methanol in methylene chloride, to give 750 mg of the title compound.

Ultraviolet Absorption Spectrum (methanol) $\lambda_{max}$ nm (ε):
 257.2

Nuclear Magnetic Resonance Spectrum (hexadeuterated dimethyl sulfoxide) δ ppm:
 4.78 (1H, quartet);
 5.61 (1H, singlet);
 5.81 (1H, singlet);
 5.99 (1H, doublet, J=6.6 Hz);
 6.47 (1H, singlet);
 8.09 (1H, singlet).

EXAMPLE 124

Dibenzhydryl 8-methoxygriseolate (Compound No. 194)

410 mg of dibenzhydryl 4',7'-anhydro-5'α-bromo-4'α-hydroxy-8-methoxygriseolate (prepared as described in Example 123) were dissolved in 80% w/v aqueous acetic acid. 0.6 g of zinc powder was added and the mixture was vigorously stirred at room temperature. After 3 hours, a further 0.6 g of zinc powder was added and the mixture was stirred for a further 3 hours. The solvent was distilled off under reduced pressure and the residue was dissolved in 30 ml of ethyl acetate and 20 ml of 0.1N hydrochloric acid. Impurities were filtered off and the organic phase was washed, in turn, with 20 ml each of water, a 5% w/v aqueous solution of sodium bicarbonate and a saturated aqueous solution of sodium chloride, and then dried over anhydrous magnesium sulfate.

The solvent was removed by evaporation under reduced pressure and the residue was purified by silica gel column chromatography through a prepacked column (Merck), eluted with a 5% v/v solution of methanol in methylene chloride, to give 85 mg of the title compound.

Ultraviolet Absorption Spectrum (methanol) $\lambda_{max}$ nm (ε):
 256.5 (13600).

Nuclear Magnetic Resonance Spectrum (hexadeuterated dimethyl sulfoxide) δ ppm:
 4.73 (1H, doublet, J=5.4 Hz);
 4.91 (1H, singlet);
 5.23 (1H, doublet, J=2.4 Hz);
 6.27 (1H, singlet);
 6.30 (1H, quartet, J=2.4 & 5.4 Hz);
 8.08 (1H, singlet).

EXAMPLE 125

8-Methoxygriseolic acid (Compound No. 195)

32 mg of dibenzhydryl 8-methoxygriseolate (prepared as described in Example 124) were dissolved in 0.3 ml of anisole and, whilst ice-cooling, 0.3 ml of trifluoroacetic acid was added and the mixture was allowed to react at room temperature for 10 minutes. Toluene was added to the reaction mixture and the solvents were distilled off.

Distillation was repeated, each time adding acetone and toluene. The residue was suspended in a small amount of acetone and triturated with hexane to give a powder. This was dissolved in a saturated aqueous solution of sodium bicarbonate and the solution was adjusted to a pH value of 2.3 with 1N hydrochloric acid. It was then purified by reverse phase column chromatography through an Rp-8 prepacked column, eluted with water, and then lyophilized, to give 18 mg of the title compound.

Ultraviolet Absorption Spectrum (methanol) $\lambda_{max}$ nm ($\epsilon$):
259.

Nuclear Magnetic Resonance Spectrum (hexadeuterated dimethyl sulfoxide) $\delta$ ppm:
4.43 (1H, singlet);
4.64 (1H, doublet, J=5.13 Hz);
5.03 (1H, doublet, J=2.44 Hz);
6.02 (1H, doublet of doublets, J=2.44 & 5.13);
6.14 (1H, singlet);
8.07 (1H, singlet).

EXAMPLE 126

8-Bromogriseolic acid (Compound No. 196)

1.75 g of 4',7'-anhydro-8-bromo-4'α-hydroxy-5'α-iodogriseolic acid (prepared as described in Example 118) were suspended in 60 ml of 1N hydrochloric acid. 624 mg of sodium hydrogen sulfite and 2.49 g of potassium iodide were added and the mixture was stirred. After this, the mixture was subjected to ultrasonic vibration, whilst ice-cooling, for 3 hours. The reaction mixture was then adjusted to a pH value of 2.2 with sodium bicarbonate and maintained in a refrigerator overnight.

The solid precipitated was collected by filtration and recrystallized from water, to give 0.63 g of the title compound in the form of yellowish-white crystals.

Ultraviolet Absorption Spectrum (H$_2$O) $\lambda_{max}$ nm ($\epsilon$):
264.

Nuclear Magnetic Resonance Spectrum (hexadeuterated dimethyl sulfoxide) $\delta$ ppm:
4.45 (1H, singlet);
4.86 (1H, doublet, J=5.4 Hz);
5.08 (1H, doublet, J=2.4 Hz);
6.20 (1H, quartet, J=2.4 & 5.4 Hz);
6.25 (1H, singlet);
8.20 (1H, singlet).

EXAMPLE 127

8-Bromo-6-desamino-6-hydroxygriseolic acid (Compound No. 197)

229 mg of 8-bromogriseolic acid (prepared as described in Example 126) were suspended in 13 ml of water and then dissolved by the addition of 2 ml of 1N aqueous sodium hydroxide. 0.3 ml of acetic acid was added and then, under a stream of nitrogen, 345 mg of sodium nitrite were added. The mixture was kept in a refrigerator for 20 hours, insulated from the outside atmosphere. At the end of this time, a further 345 mg of sodium nitrite were added and the mixture was allowed to stand for a further 27 hours. At the end of this period, a still further 345 mg of sodium nitrite were added and the mixture was allowed to stand for 17 hours.

The solvent was removed by evaporation under reduced pressure and the residue was dissolved in water. The solution was adjusted to pH 1.0 and then purified through a prepacked column Rp-8 (Merck), eluted with 10% v/v aqueous acetonitrile. The eluate from the main peak was lyophilized to give 78 mg of the title compound.

Ultraviolet Absorption Spectrum (H$_2$O) $\lambda_{max}$ nm ($\epsilon$):
255 (12900).

Nuclear Magnetic Resonance Spectrum (hexadeuterated dimethyl sulfoxide) $\delta$ ppm:
4.50 (1H, singlet);
4.80 (1H, doublet, J=6.0 Hz);
5.17 (1H, doublet, J=2.4 Hz);
6.04 (1H, quartet, J=2.4 & 6.0 Hz);
6.24 (1H, singlet);
8.17 (1H, singlet).

EXAMPLE 128

Dibenzhydryl 8-bromogriseolate (Compound No. 198)

459 mg of 8-bromogriseolic acid (prepared as described in Example 126) were dissolved in 50 ml of aqueous acetone and the solution was adjusted to a pH value of 1-2 with 3N hydrochloric acid. A solution of diphenyldiazomethane in acetone was added until its color no longer disappeared, and the mixture was stirred. The solvent was distilled off and ethyl acetate and a saturated aqueous solution of sodium bicarbonate were added to the residue. The organic phase was separated, washed with water, and dried over anhydrous magnesium sulfate. The solvent was distilled off. The residue was recrystallized from acetone to give 720 mg of the title compound.

Ultraviolet Absorption Spectrum (methanol) $\lambda_{max}$ nm ($\epsilon$):
263 (16600).

Nuclear Magnetic Resonance Spectrum (a 1:1 by volume mixture of D$_2$O and hexadeuterated dimethyl sulfoxide) $\delta$ ppm:
4.94 (1H, doublet, J=5.4 Hz);
4.94 (1H, singlet);
5.32 (1H, doublet, J=2.4 Hz);
6.36 (1H, singlet);
6.48 (1H, doublet of doublets, J=2.4 & 5.4 Hz);
8.16 (1H, singlet).

EXAMPLE 129

Dibenzhydryl 8-azidogriseolate (Compound No. 199)

720 mg of dibenzhydryl 8-bromogriseolate (prepared as described in Example 128) were dissolved in dimethylformamide, and 142 mg of sodium azide were added to the solution. The mixure was heated at 80° C. for 7 hours. At the end of this time, the solvent was distilled off and the residue was dissolved in ethyl acetate and water.

The organic phase was separated, washed with water, and dried over anhydrous magnesium sulfate. The solvent was distilled off. The residue was purified by silica gel column chromatography and crystallized with methylene chloride, giving 176 mg of the title compound.

Ultraviolet Absorption Spectrum (methanol) $\lambda_{max}$ nm ($\epsilon$):
281 (13300).

Nuclear Magnetic Resonance Spectrum (a 1:1 by volume mixture of D$_2$O and hexadeuterated dimethyl sulfoxide) $\delta$ ppm:
4.71 (1H, doublet, J=5.4 Hz);
4.90 (1H, singlet);
5.25 (1H, doublet, J=2.4 Hz);
6.18 (1H, singlet);
6.37 (1H, doublet of doublets, J=2.4 & 5.4 Hz);
8.09 (1H, singlet).

EXAMPLE 130

Dibenzhydryl 8-aminogriseolate (Compound No. 200)

1 ml of water was added to 150 mg of dibenzhydryl 8-azidogriseolate (prepared as described in Example 129), and then, whilst introducing nitrogen gas, 10 ml of pyridine containing about 1 mole of hydrogen sulfide were added. The mixture was allowed to stand overnight at room temperature, insulated from the outside atmosphere. The solvent was distilled off and the residue was purified by silica gel column chromatography, affording 110 mg of the title compound.

Ultraviolet Absorption Spectrum (methanol) $\lambda_{max}$ nm ($\epsilon$):
268 (16400).

Nuclear Magnetic Resonance Spectrum (hexadeuterated dimethyl sulfoxide) $\delta$ ppm:
4.77–4.81 (1H, multiplet);
4.85–4.87 (1H, multiplet);
5.21 (1H, doublet, J=2.74 Hz);
6.38 (1H, singlet);
6.41 (1H, doublet of doublets, J=2.74 & 5.48 Hz);
7.91 (1H, singlet).

EXAMPLE 131

8-Aminogriseolic acid (Compound No. 201)

1 ml of trifluoroacetic acid was added, whilst ice-cooling, to a solution of 100 mg of dibenzhydryl 8-aminogriseolate (prepared as described in Example 130) in 1 ml of anisole, and the mixture was allowed to stand at room temperature for 10 minutes. Toluene was added and the solvents were distilled off. Distillation was repeated, each time adding acetone and toluene. The residue was suspended in acetone and the suspension was poured into hexane, with stirring, to give a powder. This was dissolved in a saturated aqueous solution of sodium bicarbonate and the solution was adjusted to a pH value of 3 with 1N hydrochloric acid. The solution was then passed through a prepacked reverse phase chromatography column Rp-8, eluted with water. The eluate was lyophilized to give 44 mg of the title compound.

Ultraviolet Absorption Spectrum (H2O) $\lambda_{max}$ nm ($\epsilon$):
272 (16400).

Nuclear Magnetic Resonance Spectrum (hexadeuterated dimethyl sulfoxide) $\delta$ ppm:
4.43 (1H, doublet);
4.79 (1H, doublet, J=4.88 Hz);
4.99 (1H, doublet, J=1.96 Hz);
6.21 (1H, doublet of doublets, J=1.96 & 4.88 Hz);
6.31 (1H, singlet);
7.92 (1H, singlet).

EXAMPLE 132

Dibenzhydryl 4',7'-anhydro-5'α-bromo-4'α-hydroxygriseolate (Compound No. 202)

A suspension of 3.3 g of 4',7'-anhydro-5'α-bromo-4'α-hydroxygriseolic acid (prepared as described in Example 115) in 100 ml of acetone and 20 ml of water was adjusted to a pH value of about 1, and then a solution of diphenyldiazomethane in acetone was added. The mixture was stirred at room temperature. The acetone was distilled off and the residue was dissolved in ethyl acetate and a saturated aqueous solution of sodium bicarbonate. The organic phase was separated, washed with water, and dried over anhydrous magnesium sulfate. The solvent was distilled off. The residue was dissolved in a small amount of acetone and the solution was added to hexane, with stirring, to give a powder. This was collected by filtration and recrystallized from benzene/methanol to give 3.75 g of the title compound.

Ultraviolet Absorption Spectrum (methanol) $\lambda_{max}$ nm ($\epsilon$):
256.8 (16000).

Nuclear Magnetic Resonance Spectrum (a 1:1 by volume mixture of D2O and hexadeuterated dimethyl sulfoxide) $\delta$ ppm:
4.83 (1H, doublet, J=6.6 Hz);
5.66 (1H, singlet);
5.79 (1H, singlet);
6.26 (1H, doublet, J=6.6 Hz);
6.84 (1H, singlet);
8.24 (1H, singlet);
8.41 (1H, singlet).

EXAMPLE 133

Dibenzhydryl 4',7'-anhydro-4'α-hydroxy-5'α-iodogriseolate (Compound No. 204)

Essentially the same procedure as described in Example 132 was repeated, but using 505 mg of 4',7'-anhydro-4'α-hydro-5'α-iodogriseolic acid (prepared as described in Example 116). There were obtained 805 mg of the title compound.

Ultraviolet Absorption Spectrum (methanol) $\lambda_{max}$ nm ($\epsilon$):
257 (16500).

Nuclear Magnetic Resonance Spectrum (a 1:1 by volume mixture of D2O and hexadeuterated dimethyl sulfoxide) $\delta$ ppm:
4.79 (1H, doublet, J=6.6 Hz);
5.50 (1H, singlet);
5.59 (1H, singlet);
6.24 (1H, doublet, J=6.6 Hz);
6.77 (1H, singlet);
8.24 (1H, singlet);
8.34 (1H, singlet).

EXAMPLE 134

Dimethyl 4',7'-anhydro-5'α-bromo-4'α-hydroxygriseolate (Compound No. 250)

3.1 g of 1-methyl-3-p-tolyltriazene, followed by 10 ml of water, were added to a suspension of 1 g of 4',7'-anhydro-5'α-bromo-4'α-hydroxygriseolic acid (prepared as described in Example 115) in 40 ml of tetrahydrofuran. The suspension turned to a solution after about 10 minutes. After 3 hours, 1.1 g of p-toluenesulfonic acid were added and the mixture was allowed to react at room temperature for 4 hours. The reaction mixture was then allowed to stand overnight at 5° C. The solvent was distilled off and the residue was dissolved in ethyl acetate and water. The organic phase was separated, washed with water, and dried over anhydrous magnesium sulfate. The solvent was distilled off to give crystals. These crystals were collected by filtration to give 0.46 g of the title compound.

The mother liquid was concentrated, dissolved in a small amount of acetone and poured into hexane, with stirring, to give a further 0.24 g of the compound in the form of a powder.

Ultraviolet Absorption Spectrum (methanol) $\lambda_{max}$ nm ($\epsilon$):
257 (14200).

Nuclear Magnetic Resonance Spectrum (hexadeuterated dimethyl sulfoxide) $\delta$ ppm:
4.83 (1H, doublet, J=6.6 Hz);
5.28 (1H, singlet);

5.49 (1H, singlet);
6.15 (1H, doublet, J=6.6 Hz);
6.79 (1H, singlet);
8.21 (1H, singlet);
8.39 (1H, singlet).

EXAMPLE 135

Dimethyl 4',7'-anhydro-4'α-hydroxy-5'α-iodogriseolate (Compound No. 203)

Essentially the same procedure as described in Example 134 was repeated, but using 2.0 g of 4',7'-anhydro-4'α-hydroxy-5'α-iodogriseolic acid (prepared as described in Example 116). There were obtained 1.1 g of the title compound.

Ultraviolet Absorption Spectrum (methanol) $\lambda_{max}$ nm ($\epsilon$):
256.2 (15000).

Nuclear Magnetic Resonance Spectrum (hexadeuterated dimethyl sulfoxide) $\delta$ ppm:
4.80 (1H, doublet, J=6.6 Hz);
5.23 (1H, singlet);
5.26 (1H, singlet);
6.20 (1H, doublet, J=6.6 Hz);
6.79 (1H, singlet);
8.24 (1H, singlet);
8.40 (1H, singlet).

EXAMPLE 136

Dibenzhydryl 4',7'-anhydro-5'α-bromo-6-desamino-4'α-dihydroxygriseolate (Compound No. 205)

1 g of 4',7'-anhydro-5'α-bromo-6-desamino-4'α,6-dihydroxygriseolic acid (prepared as described in Example 113) was dissolved in 100 ml of tetrahydrofuran and 25 ml of water and the solution was adjusted to a pH value of 1 with 1N hydrochloric acid. Diphenyldiazomethane was added to the solution, with stirring, until the red color no longer disappeared. Stirring was continued at room temperature for 3 hours and, at the end of this time, the solvent was distilled off under reduced pressure. The residue was purified by silica gel column chromatography, eluted with a 3% v/v solution of methanol in methylene chloride, to give 970 mg of the title compound.

Ultraviolet Absorption Spectrum (methanol) $\lambda_{max}$ nm ($\epsilon$):
243.5 (10600).

Nuclear Magnetic Resonance Spectrum (a 1:1 by volume mixture of D$_2$O and CDCl$_3$) $\delta$ ppm:
4.75 (1H, doublet, J=7.5 Hz);
5.29 (1H, singlet);
5.50 (1H, singlet);
6.03 (1H, doublet, J=7.5 Hz);
6.80 (1H, singlet);
8.15 (1H, singlet);
8.34 (1H, singlet).

EXAMPLE 137

Dimethyl 4',7'-anhydro-5'α-bromo-6-desamino-4'α,6-dihydroxygriseolate (Compound No. 206)

13 g of 4',7'-anhydro-5'α-bromo-6-desamino-4'α,6-dihydroxygriseolic acid (prepared as described in Example 113) were dissolved in 800 ml of tetrahydrofuran and 200 ml of water and the solution was adjusted to a pH value of 1 with 1N hydrochloric acid. 1-Methyl-3-p-tolyltriazene was added to the solution. little by little, whereupon the solution bubbled vigorously. Addition was continued until a total of 75 g had been added. The reaction mixture was then slowly adjusted to a pH value of 1 with 1N-hydrochloric acid.

The solvent was distilled off under reduced pressure and the residue was dissolved in 500 ml of methylene chloride. The resulting solution was washed twice, each time with 300 ml of 1N hydrochloric acid. The aqueous phase was counterextracted with 300 ml of methylene chloride and the organic layer was dried over anhydrous magnesium sulfate. The solvent was then distilled off. The residue was purified by silica gel column chromatography, eluted with a 3% v/v solution of methanol in methylene chloride, to give 6.3 g of the title compound.

Ultraviolet Absorption Spectrum (methanol) $\lambda_{max}$ nm ($\epsilon$):
252.5 (9700).

Nuclear Magnetic Resonance Spectrum (a 1:1 by volume mixture of D$_2$O and hexadeuterated dimethyl sulfoxide) $\delta$ ppm:
4.66 (1H, doublet, J=7.5 Hz);
4.78 (1H, singlet);
5.17 (1H, singlet);
6.01 (1H, doublet, J=7.5 Hz);
6.53 (1H, singlet);
7.77 (1H, singlet);
7.87 (1H, singlet).

EXAMPLE 138

Dimethyl 4',7'-anhydro-N$^6$,N$^6$, O$^{2'}$-tribenzoyl-5'α-bromo-4'α-hydroxygriseolate (Compound No. 207)

0.6 g of dimethyl 4',7'-anhydro-5'α-bromo-4'α-hydroxygriseolate (prepared as described in Example 134) was suspended in 20 ml of pyridine. The suspension turned clear upon the addition, whilst ice-cooling, of 1.48 ml of benzoyl chloride. The solution was stirred at room temperature overnight. The solvent was distilled off, water was added and distillation was again effected. The residue was dissolved in ethyl acetate and a saturated aqueous solution of sodium bicarbonate. The organic phase was washed with water and dried over anhydrous magnesium sulfate, and the solvent was distilled off. The residue was recrystallized from a small amount of ethyl acetate and ethanol, giving 0.58 g of the title compound.

Ultraviolet Absorption Spectrum (methanol) $\lambda_{max}$ nm ($\epsilon$):
233 (30100), 250 shoulder (26600), 273 (20800).

Nuclear Magnetic Resonance Spectrum (hexadeuterated dimethyl sulfoxide) $\delta$ ppm:
5.25 (1H, singlet);
5.50 (1H, singlet);
5.91 (1H, doublet, J=6.6 Hz);
6.40 (1H, doublet, J=6.6 Hz);
7.32 (1H, singlet);
8.80 (1H, singlet);
8.87 (1H, singlet).

EXAMPLE 139

Dimethyl 4',7'-anhydro-N$^6$, N$^6$, O$^{2'}$-tribenzoyl-4'α-hydroxy-5'α-iodogriseolate (Compound No. 208)

3.2 g of dimethyl 4',7'-anhydro-4'α-hydroxy-5'α-iodogriseolate (prepared as described in Example 135) were suspended in 150 ml of pyridine and then, whilst ice-cooling, 6.98 ml of benzoyl chloride were added. The mixture was stirred at room temperature overnight. The solvent was distilled off, and then water was added and distillation was again carried out.

The residue was dissolved in ethyl acetate and a saturated aqueous solution of sodium bicarbonate. The organic phase was washed with water, dried over anhydrous magnesium sulfate, and the solvent was distilled off. The residue was dissolved in a small amount of ethyl acetate and, on adding ethanol, there were obtained 3.24 g of the title compound in the form of crystals.

Ultraviolet Absorption Spectrum (methanol) $\lambda_{max}$ nm ($\epsilon$):

235 (30700), 250 shoulder (27400), 271 (20900).

Nuclear Magnetic Resonance Spectrum (hexadeuterated dimethyl sulfoxide) $\delta$ ppm:
5.23 (1H, singlet);
5.33 (1H, singlet);
5.96 (1H, doublet, J=6.6 Hz);
6.50 (1H, doublet, J=6.6 Hz);
7.36 (1H, singlet);
8.84 (1H, singlet);
8.92 (1H, singlet).

We claim:

1. A griseolic acid compound of the formula:

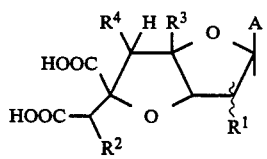

wherein:

A represents a group of formula:

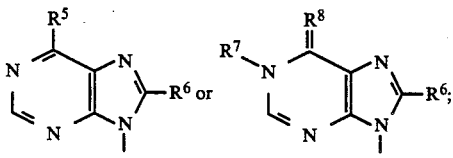

$R^1$, $R^2$, $R^5$ and $R^6$ are the same or different and each represents a hydrogen or halogen atom, the azido group, or a group of formula —$OR^9$, —$NR^{10}R^{11}$ or —$SR^9$;

$R^3$ represents a hydrogen or halogen atom or a $C_1$–$C_{20}$ aliphatic acyloxy or a ($C_6$–$C_{20}$ aromatic)acyloxy or $C_1$–$C_6$ alkoxy group;

$R^4$ represents a hydrogen or halogen atom; or $R^3$ and $R^4$ together represent an extra carbon-carbon bond between the carbon atoms to which they are attached; or $R^3$ and $R^2$ together represent an oxygen atom bridging the carbon atoms to which they are attached;

$R^7$ represents an optionally substituted $C_1$–$C_6$ alkyl, $C_3$–$C_6$ alkenyl or aralkyl group (wherein the alkyl moiety has from 1 to 6 carbon atoms), the substituents being selected from halogen atoms, $C_1$–$C_4$ alkoxy groups, ($C_1$–$C_4$ alkoxy)carbonyl groups and (where $R^7$ is substituted aralkyl) $C_1$–$C_4$ alkyl groups;

$R^8$ represents an oxygen or sulfur atom or the imino group;

$R^9$ represents hydrogen, a $C_1$–$C_6$ alkyl group, a heterocyclic group (having 5 or 6 ring atoms, of which from 1 to 3 are oxygen, nitrogen or sulfur, and being unsubstituted or having from 1 to 3 $C_1$–$C_4$ alkyl or alkoxy substituents), a tri($C_1$–$C_4$ alkyl)silyl group, an alkylsulfonyl group, a haloalkylsulfonyl group, a benzenesulphonyl optionally substituted with a $C_1$–$C_3$ alkyl group, a $C_1$–$C_{20}$ aliphatic acyl group or a $C_6$–$C_{20}$ aromatic acyl group;

$R^{10}$ and $R^{11}$ are the same or different and each represents hydrogen, hydroxy, a $C_1$–$C_6$ alkyl group, a $C_1$–$C_6$ hydroxyalkyl group, a $C_1$–$C_6$ aminoalkyl group, an aralkyl group, an aryl group, a $C_1$–$C_6$ alkoxy group, the amino group, a $C_1$–$C_{20}$ aliphatic acyl group or a $C_6$–$C_{20}$ aromatic acyl group; or $R^{10}$ and $R^{11}$, together with the nitrogen atom to which they are attached, represent a 5- or 6-membered heterocyclic group having at least one other hetero-atom selected from oxygen, and nitrogen atoms and optionally having one $C_1$–$C_4$ alkyl substituent;

and pharmaceutically acceptable salts and esters thereof;

but excluding 7'(R)-griseolic acid itself and salts thereof.

2. The compound of claim 1, wherein:
$R^1$ represents a hydrogen or halogen atom, the azido group or said group of formula —$OR^9$;
$R^2$ represents hydrogen or said group of formula —$OR^9$;
$R^3$ and $R^4$ together represent said extra bond;
$R^5$ represents a hydroxy, amino, $C_1$–$C_6$ alkylamino, acylamino or mercapto group; and
$R^6$ represents the hydrogen atom.

3. The compound of claim 1, wherein:
$R^1$ represents a hydrogen or halogen atom or said group of formula —$OR^9$;
$R^2$ represents the hydrogen atom or said group of formula —$OR^9$;
$R^3$ and $R^4$ together represent said extra bond;
$R^5$ represents the amino group; and
$R^6$ represents a halogen atom, a mercapto or $C_1$–$C_6$ alkoxy group or said group of formula —$NR^{10}R^{11}$.

4. The compound of claim 1, wherein:
$R^1$ represents the hydroxy group;
$R^4$ represents a halogen atom;
$R^3$ and $R^2$ together represent said oxygen atom;
$R^5$ represents the amino group; and
$R^6$ represents the hydrogen atom.

5. The compound of claim 1, wherein:
$R^7$ represents said optionally substituted aralkyl group; and
$R^8$ represents the imino group.

6. A compound selected from the group consisting of:
dibenzhydryl $N^6,O^{2'},O^{7'}$-tripropionylgriseolate;
disodium $N^6,O^{2'},O^{7'}$-tribenzoylgriseolate;
$N^6$-benzoylgriseolic acid;
$O^{2'}$-benzoylgriseolic acid;
$O^{7'}$-benzoylgriseolic acid;
6-desamino-6-hydroxygriseolic acid;
6-desamino-6-mercaptogriseolic acid;
$N^6,O^{2'},O^{7'}$-tribenzoylgriseolic acid;
7'-deoxygriseolic acid;
6-desamino-7'-deoxy-6-hydroxygriseolic acid;
2'(S)-chloro-2'-deoxygriseolic acid;
2'(S)-bromo-2'-deoxygriseolic acid;
2'-deoxygriseolic acid;
bis(1-pivaloyloxyethyl)griseolate;

bis(5-methyl-2-oxo-1,3-dioxolen-4-ylmethyl)griseolate;
bis(1-pivaloyloxyethyl) 6-desamino-6-hydroxygriseolate;
bis(5-methyl-2-oxo-1,3-dioxolen-4-ylmethyl) 6-desamino-6-hydroxygriseolate;
7'(S)-griseolic acid;
8-mercaptogriseolic acid;
8-methoxygriseolic acid;
8-bromogriseolic acid;
8-aminogriseolic acid;
7'(S)-acetoxy-7'-deoxygriseolic acid;
dibenzhydryl 4',7'-anhydro-5'α-bromo-4'α-hydroxygriseolate;
2'(S)-azido-2'-deoxygriseolic acid; and
$N^6$-methylgriseolic acid.

7. A pharmaceutical composition comprising an effective amount of at least one active compound in admixture with a pharmaceutically acceptable carrier or diluent, wherein the active compound is selected from griseolic acid compounds of the formula:

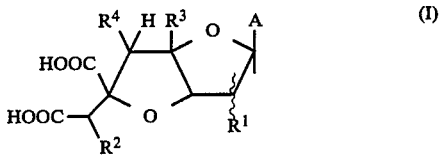

wherein:

A represents a group of formula:

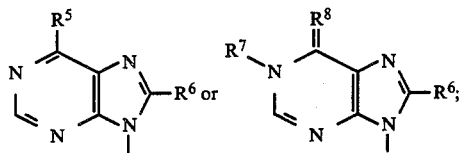

$R^1$, $R^2$, $R^5$ and $R^6$ are the same or different and each represents a hydrogen or halogen atom, the azido group, or a group of formula —$OR^9$, —$NR^{10}R^{11}$ or —$SR^9$;

$R^3$ represents a hydrogen or halogen atom or a $C_1$–$C_{20}$ aliphatic acyloxy or a ($C_6$–$C_{20}$ aromatic) acyloxy or $C_1$–$C_6$ alkoxy group;

$R^4$ represents a hydrogen or halogen atom; or $R^3$ and $R^4$ together represent an extra carbon-carbon bond between the carbon atoms to which they are attached; or $R^3$ and $R^2$ together represent an oxygen atom bridging the carbon atoms to which they are attached;

$R^7$ represents an optionally substituted $C_1$–$C_6$ alkyl, $C_3$–$C_6$ alkenyl or aralkyl group (wherein the alkyl moiety has from 1 to 6 carbon atoms), the substituents being selected from halogen atoms, $C_1$–$C_4$ alkoxy groups, ($C_1$–$C_4$ alkoxy)carbonyl groups and (where $R^7$ is substituted aralkyl) $C_1$–$C_4$ alkyl groups;

$R^8$ represents an oxygen or sulfur atom or the imino group;

$R^9$ represents hydrogen, a $C_1$–$C_6$ alkyl group, a heterocyclic group (having 5 or 6 ring atoms, of which from 1 to 3 are oxygen, nitrogen or sulfur, and being unsubstituted or having from 1 to 3 $C_1$–$C_4$ alkyl or alkoxy substituents), a tri($C_1$–$C_4$ alkyl)silyl group, an alkylsulfonyl group, a haloalkylsulfonyl group, a benzenesulphonyl optionally substituted with a $C_1$–$C_3$ alkyl group, a $C_1$–$C_{20}$ aliphatic acyl group or a $C_6$–$C_{20}$ aromatic acyl group;

$R^{10}$ and $R^{11}$ are the same or different and each represents hydrogen, hydroxy, a $C_1$–$C_6$ alkyl group, a $C_1$–$C_6$ hydroxyalkyl group, a $C_1$–$C_6$ aminoalkyl group, an aralkyl group, an aryl group, a $C_1$–$C_6$ alkoxy group, the amino group, a $C_1$–$C_{20}$ aliphatic acyl group or a $C_6$–$C_{20}$ aromatic acyl group; or $R^{10}$ and $R^{11}$, together with the nitrogen atom to which they are attached, represent a 5- or 6-membered heterocyclic group having at least one other hetero-atom selected from oxygen, and nitrogen atoms and optionally having one $C_1$–$C_4$ alkyl substituent;

and pharmaceutically acceptable salts and esters thereof;

but excluding 7'(R)-griseolic acid itself and salts thereof.

8. The composition of claim 7, wherein in said active compound:

$R^1$ represents a hydrogen or halogen atom, the azido group or said group of formula —$OR^9$;

$R^2$ represents hydrogen or said group of formula —$OR^9$;

$R^3$ and $R^4$ together represent said extra bond;

$R^5$ represents a hydroxy, amino, $C_1$–$C_6$ alkylamino, acylamino or mercapto group; and $R^6$ represents the hydrogen atom.

9. The composition of claim 7, wherein in said active compound:

$R^1$ represents a hydrogen or halogen atom or said group of formula —$OR^9$;

$R^2$ represents the hydrogen atom or said group of formula —$OR^9$;

$R^3$ and $R^4$ together represent said extra bond;

$R^5$ represents the amino group; and $R^6$ represents a halogen atom, a mercapto or $C_1$–$C_6$ alkoxy group or said group of formula —$NR^{10}R^{11}$.

10. The composition of claim 7, wherein in said active compound:

$R^1$ represents the hydroxy group;

$R^4$ represents a halogen atom;

$R^3$ and $R^2$ together represent said oxygen atom;

$R^5$ represents the amino group; and $R^6$ represents the hydrogen atom.

11. The composition of claim 7, wherein in said active compound:

$R^7$ represents said optionally substituted aralkyl group; and $R^8$ represents the imino group.

12. The composition of claim 7, wherein said active compound is selected from the group consisting of:
dibenzhydryl $N^6,O^{2'},O^{7'}$-tripropionylgriseolate;
disodium $N^6,O^{2'},O^{7'}$-tribenzoylgriseolate;
$N^6$-benzoylgriseolic acid;
$O^{2'}$-benzoylgriseolic acid;
$O^{7'}$-benzoylgriseolic acid;
6-desamino-6-hydroxygriseolic acid;
6-desamino-6-mercaptogriseolic acid;
$N^6,O^{2'},O^{7'}$-tribenzoylgriseolic acid;
7'-deoxygriseolic acid;
6-desamino-7'-deoxy-6-hydroxygriseolic acid;
2'(S)-chloro-2'-deoxygriseolic acid;
2'(S)-bromo-2'-deoxygriseolic acid;
2'-deoxygriseolic acid;
bis(1-pivaloyloxyethyl)griseolate;

bis(5-methyl-2-oxo-1,3-dioxolen-4-ylmethyl)griseolate;
bis(1-pivaloyloxyethyl) 6-desamino-6-hydroxygriseolate;
bis(5-methyl-2-oxo-1,3-dioxolen-4-ylmethyl) 6-desamino-6-hydroxygriseolate;
7'(S)-griseolic acid;
8-mercaptogriseolic acid;
8-methoxygriseolic acid;
8-bromogriseolic acid;
8-aminogriseolic acid;
7'(S)-acetoxy-7'-deoxygriseolic acid;
dibenzhydryl 4',7'-anhydro-5'α-bromo-4'α-hydroxygriseolate;
2'(S)-azido-2'-deoxygriseolic acid; and
$N^6$-methylgriseolic acid.

13. The compound of claim 1 which is dibenzhydryl $N^6,O^{2'},O^{7'}$-tripropionylgriseolate.

14. The compound of claim 1 which is disodium $N^6,O^{2'},O^{7'}$-tribenzoylgriseolate.

15. The compound of claim 1 which is $N^6$-benzoylgriseolic acid.

16. The compound of claim 1 which is $O^{2'}$-benzoylgriseolic acid.

17. The compound of claim 1 which is $O^{7'}$-benzoylgriseolic acid.

18. The compound of claim 1 which is 6-desamino-6-hydroxygriseolic acid.

19. The compound of claim 1 which is 6-desamino-6-mercaptogriseolic acid.

20. The compound of claim 1 which is $N^6,O^{2'},O^{7'}$-tribenzoylgriseolic acid.

21. The compound of claim 1 which is 7'-deoxygriseolic acid.

22. The compound of claim 1 which is 6-desamino-7'-deoxy-6-hydroxygriseolic acid.

23. The compound of claim 1 which is 2'(S)-chloro-2'-deoxygriseolic acid.

24. The compound of claim 1 which is 2'(S)-bromo-2'-deoxygriseolic acid.

25. The compound of claim 1 which is 2'-deoxygriseolic acid.

26. The compound of claim 1 which is bis(1-pivaloyloxyethyl)griseolate.

27. The compound of claim 1 which is bis(5-methyl-2-oxo-1,3-dioxolen-4-ylmethyl)griseolate.

28. The compound of claim 1 which is bis(1-pivaloyloxyethyl) 6-desamino-6-hydroxygriseolate.

29. The compound of claim 1 which is bis(5-methyl-2-oxo-1,3-dioxolen-4-ylmethyl) 6-desamino-6-hydroxygriseolate.

30. The compound of claim 1 which is 7'(S)-griseolic acid.

31. The compound of claim 1 which is 8-mercaptogriseolic acid.

32. The compound of claim 1 which is 8-methoxygriseolic acid.

33. The compound of claim 1 which is 8-bromogriseolic acid.

34. The compound of claim 1 which is 8-aminogriseolic acid.

35. The compound of claim 1 which is 7'(S)-acetoxy-7'-deoxygriseolic acid.

36. The compound of claim 1 which is dibenzhydryl 4',7'-anhydro-5'α-bromo-4'α-hydroxygriseolate.

37. The compound of claim 1 which is 2'(S)-azido-2'-deoxygriseolic acid.

38. The compound of claim 1 which is $N^6$-methylgriseolic acid.

* * * * *